(12) United States Patent
Gupta et al.

(10) Patent No.: US 8,735,542 B2
(45) Date of Patent: May 27, 2014

(54) HIV-1 CLADE A CONSENSUS SEQUENCES, ANTIGENS, AND TRANSGENES

(75) Inventors: Kalpana Gupta, New York, NY (US); Nicholas Jackson, London (GB)

(73) Assignee: International AIDS Vaccine Initiative, New York, NY (US)

(*) Notice: Subject to any disclaimer, the term of this patent is extended or adjusted under 35 U.S.C. 154(b) by 0 days.

(21) Appl. No.: 13/398,897

(22) Filed: Feb. 17, 2012

(65) Prior Publication Data

US 2012/0219577 A1 Aug. 30, 2012

Related U.S. Application Data

(63) Continuation of application No. 11/757,550, filed on Jun. 4, 2007, now Pat. No. 8,119,144.

(60) Provisional application No. 60/810,816, filed on Jun. 2, 2006.

(51) Int. Cl.
| | | |
|---|---|---|
| C07K 1/00 | (2006.01) |
| A61K 38/00 | (2006.01) |
| A61K 38/16 | (2006.01) |
| A61K 39/00 | (2006.01) |
| A61K 39/12 | (2006.01) |
| A61K 39/21 | (2006.01) |

(52) U.S. Cl.
USPC ........... 530/350; 530/395; 514/1.1; 514/21.2; 424/184.1; 424/185.1; 424/186.1; 424/187.1; 424/188.1

(58) Field of Classification Search
None
See application file for complete search history.

(56) References Cited

FOREIGN PATENT DOCUMENTS

| WO | WO 01/47955 | 7/2001 |
| WO | WO 2005/047483 | 5/2005 |

OTHER PUBLICATIONS

Los Alamos National Laboratory HIV sequence database, Consensus and Ancestral Sequence Alignments Current (Aug. 2004—subtype A Env amino acid consensus sequence).*
Los Alamos National Laboratory HIV sequence database, Consensus and Ancestral Sequence Alignments Current (Aug. 2004—subtype A Env nucleic acid consensus sequence).*
Robertson, et al. www.hiv.lanl.gov/content/sequence/HIV/.../1999/6/nomenclature.pdf (downloaded May 28, 2013).*

(Continued)

*Primary Examiner* — Zachariah Lucas
*Assistant Examiner* — Stuart W Snyder
(74) *Attorney, Agent, or Firm* — Vedder Price P.C.; Thomas J. Kowalski; Deborah L. Lu

(57) ABSTRACT

The present invention relates to consensus nucleotide and protein sequences for HIV-1 Clade A antigens, and to nucleotide and protein sequences for Clade A antigens from circulating HIV-1 field isolates wherein the antigen sequences are closely related to the these consensus sequences. Advantageously, the present invention relates to HIV-1 Clade A transgenes that are derived from such sequences, and that encode either HIV-1 Clade A Gag, Pol (RT and Int), and Nef (collectively "GRIN"), HIV-1 Clade A Gag, RT, and Nef (collectively "GRN"), or HIV-1 Clade A Env. The invention also relates to vectors containing such transgenes, including adenovirus vectors containing such transgenes. The invention also relates to immunogenic compositions comprising the HIV-1 Clade A antigens, nucleotide sequences, vectors, or transgenes of the invention, and to methods of generating an immune response against HIV in a subject by administering an effective amount of such immunogenic compositions.

2 Claims, 39 Drawing Sheets

(56) References Cited

OTHER PUBLICATIONS

Howard, et al., Genomic Structure and Nucleotide Sequence Analysis . . . ; AIDS Research and Human Retroviruses (1996) vol. 12, No. 15, p. 1413-1425.

Maim, et al., Cross-Clade Protection Induced by Human Immunodeficiency . . . , Viral Immunology (2005) vol. 18, No. 4, p. 678-688.

Grant Application No. IP0IAI056354-010001 by Johnson, Phillip, "Optimization of rAAV Vector Strategies for HIV" National Institute of Allergy and Infectious Diseases, Jul. 1, 2003.

Gao, et al., Molecular cloning and analysis of functional envelope genes from human immunodeficiency virus type I sequence subtypes A through G. The WHO and NIAID Networks for HIV Isolation and Characterization. J Virol. (1996) 70(3): 1651-67.

HIV-1 Sequence Alignment of Clade A env gene, Los Alamos National Laboratory Web Site, 1997, pp. 1,2.

Nkolola, et al. Engineering RENTA, a DNA prime-MVA boost HIV vaccine tailored for Eastern and Central Africa. Gene Therapy (2004) 11, 1068-1080.

* cited by examiner

Consensus Gag

MGARASVLSGGKLDAWEKIRLRPGGKKKYRLKLHLVWASRELERFALNPSLLETAEGCQQIM
EQLQPALKTGTEELRSLFNTVATLYCVHQRIDVKDTKEALDKIEEIQNKSKQK--TQQ--
AAADTGXSSKVS----
QNYPIVQNAQGQMIHQXLSPRTLNAWVKVIEEKAFSPEVIPMFSALSEGATPQDLNMMLNIVG
GHQAAMQMLKDTINEEAAEWDRLHPVHAGPIPPGQMREPRGSDIAGTTSTPQEQGAWMTG
NPPIPVGDIYKRWIILGLNKIVRMYSPVSILDIKQGPKEPFRDYVDRFFKTLRAEQATQEVKGW
MTETLLVQNANPDCKSILRALGXGATLEEMMTACQGVGGPGHKARVLAEAMSQVQQTN--
IMM-QRGNFRGQKR-
IKCFNCGKEGHLARNCRAPRKKGCWKCGKEGHQMKDCTERQANFLGKIWPSSKGRPGNFP
QSRPEPTAPPAEI-FGMGEEIASPPKQEQK--DREQXXPPLVSLKSLFGNDPLSQ

FIG. 1

Consensus Pol
PQITLWQRPLVTVKIGGQLKEALLDTGADDTVLEDINLPGKWKPKMIGGIGGFIKVKQYD
QILIEICGKKAIGTVLVGPTPVNIIGRNMLTQIGCTLNFPISPIETVPVKLPGMDGPKV
KQWPLTEEKIKALTEICTEMEKEGKISKIGPENPYNTPIFAIKKKDSTKWRKLVDFRELN
KRTQDFWEVQLGIPHPAGLKKKSVTVLDVGDAYFSVPLDESFRKYTAFTIPSTNNETPG
IRYQYNVLPQGWKGSPAIFQSSMTKILEPFRSKNPEIIIYQYMDDLYVGSDLEIGQHRIK
IEELRAHLLSWGFTTPDKKHQKEPPFLWMGYELHPDKWTVQPIXLPEKESWTVNDIQKLV
GKLNWASQIYAGIKVKQLCKLLRGAKALTDIVTLTEEAELELAENREILKDPVHGVYYDP
SKDLIAEIQKQGQDQWTYQIYQEPFKNLKTGKYARKRSAHTNDVKQLAEVVQKVVMESIV
IWGKTPNFKLPIQKETWETWWMDYWQATWIPEWEFVNTPPLVKLWYQLENDPIXGAEIFY
VDGAANRETKLGKAGYVIDRGRQKVVSLTETTNQKTELHAIXLALQDSGSEVNIVDSQY
ALGIIQAQPDRSESELVNQIEKLIGKDKVYLSWVPAHKGIGGNEQVDKLVSSGIRKVLF
LDGIDKAQEEHERYHSNWRXMASDFNLPPIVAKEIVASCDKCQLKGEAMHGQVDCSPGIW
QLDCTHLEGKVILVAVHVASGYIEAEVIPAETGQETAYFLLKLAGRWPVKVVHTDNGSNF
TSAAFKAACWWANIQQEFGIPYNPQSQGVVESMNKELKKIIGQVREQAEHLKTAVQMAVF
IHNFKRKGGIGGYSAGERIIDIIATDIQTKELQKQITIKIQNFRVYYRDSRDPIWKGPAKL
LWKGEGAVVIQDNSDIKVVPRRKAKIIRDYGKQMAGDDCVAGRQDED

FIG. 3

Consensus Env

MRVMGIQRNCQHLLRWG-TMILGMIIICS--XAENLWVTVYYGVPVWKDAETTLFCASDA
KAYXTEXHNVWATHACVPTDPNPQEIXLXNVTEEFNMWKNDMVEQMHTDIISLWDQSLKP
CVKLTPLCVTLXCXXXXXXXXXXXXXXXXXXXXXXXXXXXXXX--IKNCSFNMTTELRDKKQ
KVYSLFYRLDVVQI--------XXXXXXXXXSXYRLINCNTSAITQACPKVSFEPIPIHY
CAPAGFALIKCXDXEFNGTGPCKNVSTVQCTHGIKPVVSTQLLLNGSLAEXXVX-IRSEN
ITNNAKXIIVQLXXPVXINCTRPNNNTRK---SIRIGPGQAKYATGDIIGDIRQAHCNVS
RxXWNXTLQXVAXQLRXXXFXNKTIIFXXSSGGDLEITTHSFNCGGEFFYCNTSGLFNST
W-------XXXXXXXXXXXSXXSNDTITLXCRIKQIVNMWQRXGQAMYAPPIQGVIRCES
NITGLILTRDGGXXXXXXXXNETFRPGGGDMRDNWRSELYKYKVVKIEPLGVAPTRAKRR
VVEREKRAV-GIGAVFLGFLGAAGSTMGAASITLTVQARQLLSGIVQQQSNLLRAIEAQQ
HLLKLTVWGIKQLQARVLAVERYLRDQQLLGIWGCSGKLICTTNVPWNSSWSNKSXXEIW
DNMTWLQWDKEISNYTQIIYXLIEESQNQQEKNEQDLLALDKWANLWNWFDISNWLYWIK
IFIMIVGGLIGLRIVFAVLSIINRVRQGYSPLSFQTHTPNPRGLDRPGRIEEEGGEQGRD
RSIRLVSGFLALAWDDLRSLCLFSYHRLRDFILIAARTVELLGHSSLKGLRLGWEGLKYL
WNLLXYWGRELKISAINLXDTIAIAVAGWTDRVIEIGQRIGRAILHIPRRIRQGLERALL

Consensus Nef

MGGKWSKSSIVGWPEVRERMRRTPXAAX-------
GVGAVSQDLDKHGAITSSNIN
H--PSCVWLEAQEEE--
VGFPVRPQVPLRPMTYKGANDLSHFLKEKGGLDGLIYSRK
RQ
EILDLWVYHTQGYFPDWQNYTPGPGXRYPLTFGWCFKLV
PVDPDEVEKATEGENNSLLHP
ICQHGMDDEEREVLXWKFDSRLALKHRAXELHPEFYKD

The 50% consensus sequence is shown. There were 6 positions where a 50% consensus could not be reached. The mean protein distance in nef was 9.3%, range 3.2%-16.1%.

FIG. 7

GAG

AY253305    8766 bp    DNA    linear    VRL 26-AUG-2004
HIV-1 isolate 01TZA173 from Tanzania gag protein (gag) and pol protein (pol) genes, partial cds; and vif protein (vif), vpr protein (vpr), tat protein (tat), rev protein (rev), vpu protein (vpu), envelope glycoprotein (env), and nef protein (nef) genes, complete cds.

\*MGARASILSGGKLDAWEKIRLRPGGNKKYRLKHLVWASRELDRFAL
NPSLLETTEGCQQIMNQLQPAVKTGTEEIKSLFNTVATLYCVHQRIDVKDTKEALDKI
EEIQNKSKQKTQQAAADTGDSSKVSQNYPIVQNAQGQMIHQNLSPRTLNAWVKVIEEK
AFSPEVIPMFSALSEGATPQDLNVMLNIVGGHQAAMQMLKDTINEEAAEWDRLHPVQA
GPIPPGQIREPRGSDIAGTTSTPQEQLQWMTGNPPIPVGNIYKRWIILGLNKIVRMYS
PVSILDIKQGPKEPFRDYVDRFFKALRAEQATQDVKGWMTETLLVQNANPDCKSILKA
LGSGATLEEMMTACQGVGGPGHKARVLAEAMSQAQQTNIMMQRGNFRGQKRIKCFNCG
KEGHLARNCRAPRKKGCWKCGKEGHQMKDCTERQANFLGKIWPSSKGRPGNFPQSRPE
PTAPPAELFGMGEEIASLPKQEQKDREQVPPLVSLKSLFGNDPLSQ

\*MG missing in the genbank- entry, artifact of amplicon primer.

FIG. 10

POL

AF457081 3827 bp DNA linear VRL 11-OCT-2002
HIV-1 isolate 00KE_MSA4070 from Kenya, partial genome PQITLWQRPLVTKIGGQLKEALLDTGADDTVLEDINLPGKWKPRM
IGGIGGFIKVKQYDQILIEICGKKAIGTVLVGPTPVNIIGRNMLTQIGCTLNFPISPI
ETVPVTLKPGMDGPRVKQWPLTEEKIKALTEICTEMEKEGKISNIGPENPYNTPIFAI
KKKDSTKWRKLVDFRELNKRTQDFWEVQLGIPHPAGLKKKKSVTVLDVGDAYFSVPLD
ENFRKYTAFTIPSTNNETPGVRYQYNVLPQGWKGSPAIFQSSMTKILEPFRSKNPEII
IYQYMDDLYVGSDLEIGQHRTKIEELRAHLLSWGFTTPDKNHQKEPPFLWMGYELHPD
KWTVQPIMLPDKESWTVNDIQKLVGKLNWASQIYAGIKVKQLCRLLRGAKALTDIVTL
TEEAELELAENREILKDPVHGVYYDPSKDLVAEIQKQGQDQWTYQIYQEPFKNLKTGK
YARKRSAHTNDVRQLAEVVQKVAMESIVIWGKTPKFKLPIQKETWETWWMDYWQATWI
PEWEFVNTPPLVKLWYQLEKDPILGAETFYVDGAANRETKLGKAGYVTDRGRQKVVSL
TETTNQKTELHAILLALQDSGSEVNIVTDSQYALGIIQAQPDRSESELVNQIIEKLIG
KDKIYLSWVPAHKGIGGNEQVDNLVSSGIRKVLFLDGIDKAQEDHERYHSNWRTMASD
FNLPPTVAKEIVASCDKCQLKGEAMHGQVDCSPGIWQLDCTHLEGKVILVAVHVASGY
IEAEVIPAETGQETAYFLLKLAGRWPVKVVHTDNGSNFTSAAVKAACWWANIQQEFGI
PYNPQSQGVVESMNKELKKIIGQVRDQAEHLKTAVQMAVFIHNFKRKGGIGGYSAGER
IIDIIATDIQTKELQKQITKIQNFRVYYRDSRDPIWKGPAKLLWKGEGAVVIQDNSDI
KVVPRRKAKIILRDYGKQMAGDDCVAGRQDED

FIG. 11

NEF

AF457081     8827 bp    DNA    linear   VRL 11-OCT-3002
HIV-1 isolate 00KE_MSA4070 from Kenya, partial genome.

MGGKWSKGSIVGWPEIRERMRRAPAAAPGVGAVSQDLDKHGAIT
SSNNNPSCVWLEAQEEEVGFPVRPQVPLRPMTYKGAFDLSHFLKEKGGLDGLIYSR
KRQEILDLWVYHTQGYFPDWQNYTPGPGVRYPLTFGWCFKLVPMEPDEVEKATEGENN
SLLHPICQHGMDDEEREVLIWKFDSRLALKHRAQELHPEFYKDC

ENV

AY253314    8758 BP    DNA    LINEAR    VRL 26-AUG-2004

HIV-1 isolate 01TZA341 from Tanzania gag protein (gag) and pol protein (pol) genes, partial cds; and vif protein (vif), vpr protein (vpr), tat protein (tat), rev protein (rev), vpu protein (vpu), envelope glycoprotein (env), and nef protein (nef) genes, complete cds The Env gp140 sequence below does NOT include the trans-membrane region MRVMEIQRNCQHLLRWGMILGMIICSTADNLWVTVYYGVPVW
RDAETTLFCASDAKAYSTEKHNVWATHACVPTDPNPQEIPLDNVTEEFNMWKNNMVDQ
MHEDIISLWDQSLKPCVQLTPLCVTLNCSNARVNATFNSTEDREGMKNCSFNITTELR
DKKQQVYSLFYRLDIEKINSSNNFSEYRLINCNTSAITQACPKVTFEPIPIHYCAPAG
FAILKCNDTEFNGTGPCKNVSTVQCTHGIKPVVSTQLLLNGSLAEREVRIRSENIANN
AKNIIVQFASPVKINCIRPNNNTRKSYRIGPGQTFYATDIVGDIRQAHCNVSRTDWNN
TLRLVANQLRKYFSNKTIIFTNSSGGDLEITTHSFNCGGEFFYCNTSGLFNSTWTINN
MQESNDTSNGTITLPCRIKQIIRMWQRVGQAMYAPPIEGVIRCESNITGLILTRDGGN
NNSANETFRPGGGDIRDNWRSELYKYKVVKIEPLGVAPTRAKRRVVEREKRAVGIGAV
FLGFLGAAGSTMGAASITLTVQARQLLSGIVQQQSNLRAIEAQQQLLKLTVWGIKQL
QARVLAVERYLRDQQLLGIWGCSGKLICTTNVPWNSSWSNKSYDDIWQNMTWLQWDKE
ISNYTDIIYSLIEESQNQQEKNEQDLLALDKWANLWNWFDISKWLWYI Assembled sequence GRIN insert (DZU36984)

AGTCTTCTGTTTTTACGTAGGTGTCAGCCTAGGTGGTCAATATTGGCCATTAGCC
ATATTATTCATTGGTTATATAGCATAAATCAATATTGGCTATTGGCCATTGCATAC
GTTGTATCCATATCATAATATGTACATTTATATTGGCTCATGTCCAACATTACCGC
CATGTTGACATTGATTATTGACTAGTTATTAATAGTAATCAATTACGGGGTCATTA
GTTCATAGCCCATATATGGAGTTCCGCGTTACATAACTTACGGTAAATGGCCCGC
CTGGCTGACCGCCCAACGACCCCGCCCATTGACGTCAATAATGACGTATGTTC
CCATAGTAACGCCAATAGGGACTTTCCATTGACGTCAATGGGTGGAGTATTTAC
GGTAAACTGCCCACTTGGCAGTACATCAAGTGTATCATATGCCAAGTACGCCCC
CTATTGACGTCAATGACGGTAAATGGCCCGCCTGGCATTATGCCCAGTACATGA
CCTTATGGGACTTTCCTACTTGGCAGTACATCTACGTATTAGTCATCGCTATTAC
CATGGTGATGCGGTTTTGGCAGTACATCAATGGGCGTGGATAGCGGTTTGACTC
ACGGGGATTTCCAAGTCTCCACCCCATTGACGTCAATGGGAGTTTGTTTTGGCA
CCAAAATCAACGGGACTTTCCAAAATGTCGTAACAACTCCGCCCCATTGACGCA
AATGGGCGGTAGGCGTGTACGGTGGGAGGTCTATATAAGCAGAGCTCGTTTAGT
GAACCGTCAGATCGCCTGGAGACGCCATCCACGCTGTTTTGACCTCCATAGAAG
ACACCGGGACCGATCCAGCCTCCGCGGCCGGGAACGGTGCATTGGAAGCTTG
CCGCCACCATGGCCGCCAGAGCCAGCATCCTGAGCGGGGGCAAGCTGGACGC
CTGGGAGAAGATCAGACTGAGGCCTGGCGGCAAGAAGAAGTACCGGCTGAAGC
ACCTGGTGTGGGCCAGCAGAGAGCTGGATCGCTTCGCCCTGAATCCTAGCCTG
CTGGAGACCACCGAGGGCTGCCAGCAGATCATGAACCAGCTGCAGCCCGCCGT
GAAAACCGGCACCGAGGAGATCAAGAGCCTGTTCAACACCGTGGCCACCCTGT
ACTGCGTGCACCAGCGGATCGACGTGAAGGATACCAAGGAGGCCCTGGACAAG
ATCGAGGAGATCCAGAACAAGAGCAAGCAGAAAACCCAGCAGGCCGCTGCCGA
CACCGGCGACAGCAGCAAAGTGAGCCAGAACTACCCCATCATCCAGAATGCCC
AGGGCCAGATGATCCACCAGAACCTGAGCCCCAGAACCCTGAATGCCTGGGTG
AAAGTGATCGAGGAAAAGGCCTTCAGCCCCGAAGTGATCCCTATGTTCAGCGCC
CTGAGCGAGGGCGCCACCCCCCAGGACCTGAACGTGATGCTGAACATTGTGGG
CGGACACCAGGCCGCCATGCAGATGCTGAAGGACACCATCAATGAGGAGGCCG
CCGAGTGGGACAGACTGCACCCCGTGCAGGCCGGACCCATCCCCCCTGGCCA
GATCAGAGAGCCCAGAGGCAGCGACATCGCCGGCACCACCTCCACCCCTCAAG
AACAGCTGCAGTGGATGACCGGCAACCCTCCCATCCCTGTGGGCAACATCTACA
AGCGGTGGATCATCCTGGGCCTGAACAAGATTGTGCGGATGTACAGCCCCGTG
TCCATCCTGGATATCAAGCAGGGCCCCAAGGAGCCCTTCAGAGACTACGTGGA
CCGGTTCTTCAAGGCCCTGAGAGCCGAGCAGGCCACCCAGGACGTGAAGGGCT
GGATGACCGAGACCCTGCTGGTGCAGAACGCCAACCCCGACTGCAAGAGCATC
CTGAAGGCCCTGGGCAGCGGCGCCACACTGGAGGAGATGATGACCGCCTGCC
AGGGAGTGGGCGGACCCGGCCACAAGGCCAGAGTGCTGGCCGAGGCCATGAG
CCAGGCCCAGCAGACCAACATCATGATGCAGCGGGGCAACTTCAGAGGCCAGA
AGCGGATCAAGTGCTTCAACTGCGGCAAGGAGGGCCACCTGGCCAGAAACTGC
AGAGCCCCCAGGAAGAAGGGCTGCTGGAAGTGTGGCAAGGAAGGGCACCAGA
TGAAGGACTGCACCGAGAGGCAGGCCAATTTCCTGGGCAAGATTTGGCCTAGC

FIG. 14A

```
AGCAAGGGCAGACCCGGCAATTTCCCCCAGAGCAGACCCGAGCCCACCGCCCC
TCCCGCCGAGCTGTTCGGCATGGGCGAGGGCATCGCCAGCCTGCCCAAGCAG
GAGCAGAAGGACAGAGAGCAGGTGCCCCCCCTGGTGTCCCTGAAGTCCCTGTT
CGGCAACGATCCTCTGAGCCAGGGATCCCCCATCAGCCCCATCGAGACCGTGC
CCGTGACCCTGAAGCCCGGCATGGATGGCCCCAAAGTGAAACAGTGGCCCCTG
ACCGAGGAGAAGATTAAGGCCCTGACCGAAATCTGTACCGAGATGGAGAAGGA
GGGCAAGATCAGCAAGATCGGCCCCGAGAACCCCTACAACACCCCATCTTCG
CCATCAAGAAGAAGGACAGCACCAAGTGGCGGAAACTGGTGGACTTCCGGGAG
CTGAACAAGAGGACCCAGGACTTCTGGGAAGTGCAGCTGGGCATCCCCCACCC
TGCCGGCCTGAAGAAGAAGAAGTCCGTGACAGTGCTGGATGTGGGCGACGCCT
ACTTCAGCGTGCCCCTGGACGAGAACTTCAGGAAGTACACCGCCTTCACCATCC
CCAGCACCAACAACGAGACCCCCGGAGTGAGATACCAGTACAACGTGCTGCCT
CAGGGCTGGAAGGGCAGCCCCGCCATCTTCCAGAGCAGCATGACCAAGATCCT
GGAGCCCTTCCGGAGCAAGAACCCCGAGATCATCATCTACCAGTACATGGCCG
CCCTGTATGTGGGCAGCGATCTGGAGATCGGCCAGCACAGGACCAAGATCGAA
GAGCTGAGGGCCCACCTGCTGAGCTGGGGCTTCACCACCCCCGATAAGAAGCA
CCAGAAGGAGCCCCCTTTCCTGTGGATGGGCTACGAGCTGCACCCCGATAAGT
GGACCGTGCAGCCCATCATGCTGCCCGATAAGGAGAGCTGGACCGTGAACGAC
ATCCAGAAACTGGTGGGCAAGCTGAATTGGGCCAGCCAAATCTACGCCGGCATT
AAAGTGAAGCAGCTGTGCAGGCTGCTGAGAGGCGCCAAAGCCCTGACAGACAT
CGTGACACTGACAGAGGAGGCCGAGCTGGAGCTGGCCGAGAACAGGGAGATC
CTGAAGGACCCCGTGCACGGCGTGTACTACGACCCCAGCAAGGACCTGGTGGC
CGAGATTCAGAAGCAGGGCCAGGACCAGTGGACCTACCAAATCTACCAGGAGC
CTTTCAAGAACCTGAAAACCGGGAAGTACGCCAGGAAGAGAAGCGCCCACACC
AACGATGTGAGGCAGCTGGCCGAAGTGGTGCAGAAAGTGGCTATGGAGAGCAT
CGTGATCTGGGGCAAGACCCCAAGTTCAAGCTGCCCATCCAGAAGGAGACCT
GGGAAACCTGGTGGATGGACTACTGGCAGGCCACCTGGATTCCTGAGTGGGAG
TTCGTGAACACCCCCCTCTGGTGAAGCTGTGGTATCAGCTGGAGAAGGACCC
CATCCTGGGCGCCGAGACCTTCTACGTGGACGGAGCCGCCAATAGAGAGACCA
AGCTGGGCAAGGCCGGCTACGTGACCGACAGAGGCAGACAGAAAGTGGTGTCT
CTGACCGAGACAACCAACCAGAAAACCGAGCTGCACGCCATCCTGCTGGCCCT
GCAGGACAGCGGCAGCGAAGTGAACATCGTGACCGACTCCCAGTACGCCCTGG
GCATCATTCAGGCCCAGCCCGATAGAAGCGAGAGCGAGCTGGTGAACCAGATC
ATCGAGAAGCTGATCGGCAAGGACAAAATCTACCTGAGCTGGGTGCCCGCCCA
CAAGGGCATCGGCGGCAACGAGCAGGTGGACAAGCTGGTGTCCAGCGGCATC
CGGAAAGTGCTGTTTCTGGACGGCATCGACAAGGCCCAGGAGGACCACGAGAG
ATACCACAGCAACTGGCGGACAATGGCCAGCGACTTCAACCTGCCTCCCATCGT
GGCCAAGGAGATCGTGGCCAGCTGCGATAAGTGTCAGCTGAAGGGCGAGGCCA
TGCACGGCCAGGTGGACTGCAGCCCTGGCATCTGGCAGCTGGCCTGCACCCAC
CTGGAGGGCAAAGTGATTCTGGTGGCCGTGCACGTGGCCAGCGGCTACATCGA
GGCCGAAGTGATTCCCGCCGAGACCGGCCAGGAGACCGCCTACTTCCTGCTGA
AGCTGGCCGGCAGATGGCCCGTGAAAGTGGTGCACACCGCCAACGGCAGCAA
CTTCACCTCTGCCGCCGTGAAGGCCGCCTGTTGGTGGGCCAATATCCAGCAGG
```

FIG. 14B

```
AGTTCGGCATCCCCTACAACCCTCAGAGCCAGGGCGTGGTGGCCAGCATGAAC
AAGGAGCTGAAGAAGATCATCGGCCAGGTGAGGGACCAGGCCGAGCACCTGAA
AACAGCCGTGCAGATGGCCGTGTTCATCCACAACTTCAAGCGGAAGGGCGGCA
TTGGCGGCTACAGCGCCGGAGAGCGGATCATCGACATCATCGCCACCGATATC
CAGACCAAGGAACTGCAGAAGCAGATCACCAAGATTCAGAACTTCAGAGTGTAC
TACCGGGACAGCAGGGACCCCATCTGGAAGGGCCCTGCCAAGCTGCTGTGGAA
GGGCGAAGGCGCCGTGGTGATCCAGGACAACAGCGACATCAAAGTGGTGCCCC
GGAGGAAGGCCAAGATTCTGCGGGACTACGGCAAACAGATGGCCGGCGATGAC
TGCGTGGCCGGCAGGCAGGATGAGGACAGATCTATGGGCGGCAAGTGGTCCAA
GGGCAGCATTGTGGGCTGGCCCGAGATCCGGGAGAGAATGAGAAGAGCCCCT
GCCGCCGCTCCTGGAGTGGGCGCCGTGTCTCAGGATCTGGATAAGCACGGCG
CCATCACCAGCAGCAACATCAACAACCCCAGCTGTGTGTGGCTGGAGGCCCAG
GAAGAGGAGGAAGTGGGCTTCCCTGTGAGACCCCAGGTGCCCCTGAGACCCAT
GACCTACAAGGGCGCCTTCGACCTGAGCCACTTCCTGAAGGAGAAGGGCGGCC
TGGACGGCCTGATCTACAGCCGGAAGCGGCAGGAGATCCTGGATCTGTGGGTG
TACCACACCCAGGGCTACTTCCCCGACTGGCAGAATTACACCCCTGGCCCTGGA
GTGCGGTATCCCCTGACCTTCGGCTGGTGCTTCAAGCTGGTGCCTATGGAGCC
CGACGAAGTGGAGAAGGCCACAGAGGGCGAGAACAACAGCCTGCTGCACCCTA
TCTGCCAGCACGGCATGGACGATGAGGAGCGGGAAGTGCTGATCTGGAAGTTC
GACAGCAGGCTGGCCCTGAAGCACAGAGCCCAGGAACTGCACCCAGAGTTCTA
CAAGGACTGCTGATGATCATAATAATCTAGACGAGATCCGAACTTGTTTATTGCA
GCTTATAATGGTTACAAATAAAGCAATAGCATCACAAATTTCACAAATAAAGCATT
TTTTTCACTGCATTCTAGTTGTGGTTTGTCCAAACTCATCAATGTATCTTATCATG
TCTAGATCTGAGGTATGATGATACGAGATCGAGGGTGCGCGCATGCGAATGCG
GAGGCAAGCATGCCAGGTTCCAGC
```

Note: cloning sites are underlined and bold

FIG. 14C

Appendix 2: Assembled sequence Env insert (DSP33447_01)

ATTATTGAAGCATTTATCAGGGTTATTGTCTCATGAGCGGATACATATTTGAATG
TATTTAgAAAAATAAACAAATAGGGGTTCCGCGCACATTTCCCCGAAAAGTGCCA
CCTGACGTCTAAGAAACCATtATTATCATgACATTAACCTATAAAAATAGGCGtAT
CACGAGGCCCtTTCGTCTTCAAGAATTGGTCGATGGCAAACAGCTATtATGGGTA
TTATGGGTTCGAATTAATTAATCGACATCATCAATAATATACCTTATAGATGGAAT
GGTGCCAATATGTAAATGAGGTGATTTTAAAAAGTGTGGGCCGTGTGGTGATTG
GCTGTGGGGTTAACGGTTAAAAGGGGCGGCGCGGCCGTGGGAAAATGACGTT
TTATGGGGGTGGAGTTTTTTTGCAAGTTGTCGCGGGAAATGTTACGCATAAAAA
GGCTTCTTTTCTCACGGAACTACTTAGTTTTCCCACGGTATTTAACAGGAAATGA
GGTAGTTTTGACCGGATGCAAGTGAAAATTGCTGATTTTCGCGCGAAAACTGAA
TGAGGAAGTGTTTTTCTGAATAATGTGGTATTTATGGCAGGGTGGAGTATTTGTT
CAGGGCCAGGTAGACTTTGACCCATTACGTGGAGGTTTCGATTACCGTGTTTTT
TACCTGAATTTCCGCGTACCGTGTCAAAGTCTTCTGTTTTTACGTAGGTGTCAGC
CTAGGTGGTCAATATTGGCCATTAGCCATATTATTCATTGGTTATATAGCATAAA
TCAATATTGGCTATTGGCCATTGCATACGTTGTATCCATATCATAATATGTACATT
TATATTGGCTCATGTCCAACATTACCGCCATGTTGACATTGATTATTGACTAGTT
ATTAATAGTAATCAATTACGGGGTCATTAGTTCATAGCCCATATATGGAGTTCCG
CGTTACATAACTTACGGTAAATGGCCCGCCTGGCTGACCGCCCAACGACCCCC
GCCCATTGACGTCAATAATGACGTATGTTCCCATAGTAACGCCAATAGGGACTT
TCCATTGACGTCAATGGGTGGAGTATTTACGGTAAACTGCCCACTTGGCAGTAC
ATCAAGTGTATCATATGCCAAGTACGCCCCCTATTGACGTCAATGACGGTAAAT
GGCCCGCCTGGCATTATGCCCAGTACATGACCTTATGGGACTTTCCTACTTGGC
AGTACATCTACGTATTAGTCATCGCTATTACCATGGTGATGCGGTTTTGGCAGTA
CATCAATGGGCGTGGATAGCGGTTTGACTCACGGGGATTTCCAAGTCTCCACC
CCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGG
TGGGAGGTCTATATAAGCAGAGCTCGTTTAGTGAACCGTCAGATCGCCTGGAG
ACGCCATCCACGCTGTTTTGACCTCCATAGAAGACACCGGGACCGATCCAGCC
TCCGCGGCCGGGAACGGTGCATTGGAAGCTTGCCGCCACCATGAGGGTGATG
GAGATCCAGCGGAACTGCCAGCACCTGCTGAGATGGGGCATCATGATCCTGGG
CATGATTATCATCTGCAGCACCGCCGACAACCTGTGGGTGACCGTGTACTACG
GCGTGCCTGTGTGGAGAGATGCCGAGACCACCCTGTTCTGCGCCAGCGACGC
CAAGGCCTACAGCACCGAGAAGCACAATGTGTGGGCCACCCACGCCTGCGTG
CCTACCGATCCCAACCCTCAGGAGATCCCCCTGGACAACGTGACCGAGGAGTT
CAACATGTGGAAGAACAACATGGTGGACCAGATGCACGAGGACATCATCAGCC
TGTGGGACCAGAGCCTGAAGCCCTGCGTGCAGCTGACCCCCCTGTGCGTGAC
CCTGAACTGCAGCAACGCCAGAGTGAACGCCACCTTCAACTCCACCGAGGACA
GGGAGGGCATGAAGAACTGCAGCTTCAACATGACCACCGAGCTGCGGGATAAG
AAGCAGCAGGTGTACAGCCTGTTCTACCGGCTGGACATCGAGAAGATCAACAG
CAGCAACAACAACAGCGAGTACCGGCTGGTGAACTGCAATACCAGCGCCATCA
CCCAGGCCTGCCCTAAGGTGACCTTCGAGCCCATCCCCATCCACTACTGCGCC

FIG. 15A

CCTGCCGGCTTCGCCATCCTGAAGTGCAACGACACCGAGTTCAATGGCACCGG
CCCCTGCAAGAATGTGAGCACCGTGCAGTGCACCCACGGCATCAAGCCCGTG
GTGTCCACCCAGCTGCTGCTGAACGGCAGCCTGGCCGAGAGAGAAGTGCGGA
TCAGGAGCGAGAACATCGCCAACAACGCCAAGAACATCATCGTGCAGTTCGCC
AGCCCCGTGAAGATCAACTGCATCCGGCCCAACAACAATACCCGGAAGAGCTA
CAGAATCGGCCCTGGCCAGACCTTCTACGCCACCGACATTGTGGGCGACATCA
GACAGGCCCACTGCAACGTGTCCAGGACCGACTGGAACAACACCCTGAGACTG
GTGGCCAACCAGCTGCGGAAGTACTTCAGCAACAAGACCATCATCTTCACCAAC
AGCAGCGGCGGAGACCTGGAGATCACCACCCACAGCTTCAATTGTGGCGGCG
AGTTCTTCTACTGCAACACCTCCGGCCTGTTCAATAGCACCTGGACCACCAACA
ACATGCAGGAGTCCAACGACACCAGCAACGGCACCATCACCCTGCCCTGCCGG
ATCAAGCAGATCATCCGGATGTGGCAGCGCGTGGGCCAGGCCATGTACGCCC
CTCCCATCGAGGGCGTGATTCGCTGCGAGAGCAACATCACCGGCCTGATCCTG
ACCAGAGATGGCGGCAACAACAATTCCGCCAACGAGACCTTCAGACCTGGCGG
CGGAGATATCCGGGACAACTGGCGGAGCGAGCTGTACAAGTACAAGGTGGTG
AAGATCGAGCCCCTGGGCGTGGCCCCCACCAGAGCCAAGAGAAGAGTGGTGG
AGCGGGAGAAGAGAGCCGTGGGCATCGGCGCCGTGTTTCTGGGCTTCCTGGG
AGCCGCCGGATCTACAATGGGAGCCGCCAGCATCACCCTGACCGTGCAGGCC
AGACAGCTGCTGAGCGGCATCGTGCAGCAGCAGAGCAATCTGCTGAGAGCCAT
CGAGGCCCAGCAGCAGCTGCTGAAGCTGACAGTGTGGGGCATCAAGCAGCTG
CAGGCCAGGGTGCTGGCCGTGGAGAGATACCTGAGGGACCAGCAGCTCCTGG
GCATCTGGGGCTGCAGCGGCAAGCTGATCTGCACCACCAACGTGCCCTGGAAT
AGCAGCTGGAGCAACAAGAGCTACGACGACATCTGGCAGAACATGACCTGGCT
GCAGTGGGACAAGGAGATCAGCAACTACACCGACATCATCTACAGCCTGATCG
AGGAGAGCCAGAACCAGCAGGAGAAGAACGAGCAGGATCTGCTGGCCCTGGA
CAAGTGGGCCAACCTGTGGAACTGGTTCGACATCAGCAAGTGGCTGTGGTACA
TCAGATCTTGATAATCTAGACGAGATCCGAACTTGTTTATTGCAGCTTATAATGG
TTACAAATAAAGCAATAGCATCACAAATTTCACAAATAAAGCATTTTTTTCACTGC
ATTCTAGTTGTGGTTTGTCCAAACTCATCAATGTATCTTATCATGTCTAGATCTGA
GGTATGATGATACGAGATCGAGGGTGCGCGCATGCGAATGCGGAGGCAAGCA
TGCCAGGTTCCAGCCGGTGTGTAGATGTGACCGAAGATCTCAGACCGGATC
ATTTGGTTATTGCCCGCACTGGAGCAGAGTTCGGATCCAGTGGAGAAGAAACT
GACTAAGGTGAGTATTGGGAAAACTTTGGGGTGGGATTTTCAGATGGACAGATT
GAGTAAAAATTTGTTTTTTCTGTCTTGCAGCTGACATGACTGGAAATGCTTCTTT
TAAGGGGGGGAGTCTTCAGCCCTTATCTGACAGGGCGTCTCCCATCCTGGGCA
GGAGTTCGT

Note: cloning sites are underlined and bold

FIG. 15B

```
HindIII      NcoI                                                    BstNI
        AAGCTTGCCGCCACCATGGCCGCCAGAGCCAGCATCCTGAGCGGGGGCAAGCTGGACGCC
  1     ---------+---------+---------+---------+---------+---------+
        TTCGAACGGCGGTGGTACCGGCGGTCTCGGTCGTAGGACTCGCCCCCGTTCGACCTGCGG
                     M  A  A  R  A  S  I  L  S  G  G  K  L  D  A StuI
                        BstNI                                        BstNI
        TGGGAGAAGATCAGACTGAGGCCTGGCGGCAAGAAGAAGTACCGGCTGAAGCACCTGGTG
 61     ---------+---------+---------+---------+---------+---------+
        ACCCTCTTCTAGTCTGACTCCGGACCGCCGTTCTTCTTCATGGCCGACTTCGTGGACCAC
        W  E  K  I  R  L  R  P  G  G  K  K  K  Y  R  L  K  H  L  V HinfI        BsaI
        TGGGCCAGCAGAGAGCTGGATCGCTTCGCCCTGAATCCTAGCCTGCTGGAGACCACCGAG
121     ---------+---------+---------+---------+---------+---------+
        ACCCGGTCGTCTCTCGACCTAGCGAAGCGGGACTTAGGATCGGACGACCTCTGGTGGCTC
        W  A  S  R  E  L  D  R  F  A  L  N  P  S  L  L  E  T  T  E PvuII
                        PstI
        GGCTGCCAGCAGATCATGAACCAGCTGCAGCCCGCCGTGAAAACCGGCACCGAGGAGATC
181     ---------+---------+---------+---------+---------+---------+
        CCGACGGTCGTCTAGTACTTGGTCGACGTCGGGCGGCACTTTTGGCCGTGGCTCCTCTAG
        G  C  Q  Q  I  M  N  Q  L  Q  P  A  V  K  T  G  T  E  E  I AAGAGCCTGTTCAACACCGTGGCCACCCTGTACTGCGTGCACCAGCGGATCGACGTGAAG
241     ....|....|....|....|....|....|....|....|....|....|....|....|
        TTCTCGGACAAGTTGTGGCACCGGTGGGACATGACGCACGTGGTCGCCTAGCTGCACTTC
        K  S  L  F  N  T  V  A  T  L  Y  C  V  H  Q  R  I  D  V  K BstNI
        GATACCAAGGAGGCCCTGGACAAGATCGAGGAGATCCAGAACAAGAGCAAGCAGAAAACC
301     ---------+---------+---------+---------+---------+---------+
        CTATGGTTCCTCCGGGACCTGTTCTAGCTCCTCTAGGTCTTGTTCTCGTTCGTCTTTTGG
        D  T  K  E  A  L  D  K  I  E  E  I  Q  N  K  S  K  Q  K  T CAGCAGGCCGCTGCCGACACCGGCGACAGCAGCAAAGTGAGCCAGAACTACCCCATCATC
361     ---------+---------+---------+---------+---------+---------+
        GTCGTCCGGCGACGGCTGTGGCCGCTGTCGTCGTTTCACTCGGTCTTGATGGGGTAGTAG
        Q  Q  A  A  A  D  T  G  D  S  S  K  V  S  Q  N  Y  P  I  I BstNI                                              BstNI
        CAGAATGCCCAGGGCCAGATGATCCACCAGAACCTGAGCCCCAGAACCCTGAATGCCTGG
421     ---------+---------+---------+---------+---------+---------+
        GTCTTACGGGTCCCGGTCTACTAGGTGGTCTTGGACTCGGGGTCTTGGGACTTACGGACC
        Q  N  A  Q  G  Q  M  I  H  Q  N  L  S  P  R  T  L  N  A  W
```

FIG. 16A

```
                      StuI                                  HaeII
             GTGAAAGTGATCGAGGAAAAGGCCTTCAGCCCCGAAGTGATCCCTATGTTCAGCGCCCTG
    481      ---------+---------+---------+---------+---------+---------+
             CACTTTCACTAGCTCCTTTTCCGGAAGTCGGGGCTTCACTAGGGATACAAGTCGCGGGAC
              V   K   V   I   E   E   K   A   F   S   P   E   V   I   P   M   F   S   A   L

NarI
                  KasI
                  HaeII         BstNI                                           BstNI
             ACCGAGGGCGCCACCCCCCAGGACCTGAACGTCATGCTGAACATTCTGGGCGGACACCAG
    541      ---------+---------+---------+---------+---------+---------+
             TGGCTCCCGCGGTGGGGGGTCCTGGACTTGCAGTACGACTTGTAACACCCGCCTGTGGTC
              S   E   G   A   T   P   Q   D   L   N   V   M   L   N   I   V   G   G   H   Q

GCCGCCATGCAGATGCTGAAGGACACCATCAATGAGGAGGCCGCCGAGTGGGACAGACTG
    601      ---------+---------+---------+---------+---------+---------+
             CGGCGGTACGTCTACGACTTCCTGTGGTAGTTACTCCTCCGGCGGCTCACCCTGTCTGAC
              A   A   M   Q   M   L   K   D   T   I   N   E   E   A   A   E   W   D   R   L

BstNI
             CACCCCGTGCAGGCCGGACCCATCCCCCCTGGCCAGATCAGAGAGCCCAGAGGCAGCGAC
    661      ---------+---------+---------+---------+---------+---------+
             GTGGGGCACGTCCGGCCTGGGTAGGGGGGACCGGTCTAGTCTCTCGGGTCTCCGTCGCTG
              H   P   V   Q   A   G   P   I   P   P   G   Q   I   R   E   P   R   G   S   D

PvuII
                                          PstI                                  BstXI
             ATCGCCGGCACCACCTCCACCCCTCAAGAACAGCTGCAGTGGATGACCGGCAACCCTCCC
    721      ---------+---------+---------+---------+---------+---------+
             TAGCGGCCGTGGTGGAGGTGGGGAGTTCTTGTCGACGTCACCTACTGGCCGTTGGGAGGG
              I   A   G   T   T   S   T   P   Q   E   Q   L   Q   W   M   T   G   N   P   P

BstNI
             ATCCCTGTGGGCAACATCTACAAGCGGTGGATCATCCTGGGCCTGAACAAGATTGTGCGG
    781      ---------+---------+---------+---------+---------+---------+
             TAGGGACACCCGTTGTAGATGTTCGCCACCTAGTAGGACCCGGACTTGTTCTAACACGCC
              I   P   V   G   N   I   Y   K   R   W   I   I   L   G   L   N   K   I   V   R

EcoRV
                     BstNI           ApaI
             ATGTACAGCCCCGTGTCCATCCTGGATATCAAGCAGGGCCCCAAGGAGCCCTTCAGAGAC
    841      ---------+---------+---------+---------+---------+---------+
             TACATGTCGGGGCACAGGTAGGACCTATAGTTCGTCCCGGGGTTCCTCGGGAAGTCTCTG
              M   Y   S   P   V   S   I   L   D   I   K   Q   G   P   K   E   P   F   R   D

AgeI                                              BstNI
             TACGTGGACCGGTTCTTCAAGGCCCTGAGAGCCGAGCAGGCCACCCAGGACGTGAAGGGC
    901      ---------+---------+---------+---------+---------+---------+
             ATGCACCTGGCCAAGAAGTTCCGGGACTCTCGGCTCGTCCGGTGGGTCCTGCACTTCCCG
              Y   V   D   R   F   F   K   A   L   R   A   E   Q   A   T   Q   D   V   K   G
```

FIG. 16B

```
              BsaI
       TGGATGACCGAGACCCTGCTGGTGCAGAACGCCAACCCCGACTGCAAGAGCATCCTGAAG
 961   ---------+---------+---------+---------+---------+---------+
       ACCTACTGGCTCTGGGACGACCACGTCTTGCGGTTGGGGCTGACGTTCTCGTAGGACTTC
       W__M__T__E__T__L__L__V__Q__N__A__N__P__D__C__K__S__I__L__K__

NarI
                KasI                             PflMI
        BstNI   HaeII                            BstNI
       GCCCTGGGCAGCGGCGCCACACTGGAGGAGATGATGACCGCCTGCCAGGGAGTGGGCGGA
1021   ---------+---------+---------+---------+---------+---------+
       CGGGACCCGTCGCCGCGGTGTGACCTCCTCTACTACTGGCGGACGGTCCCTCACCCGCCT
       A__L__G__S__G__A__T__L__E__E__M__M__T__A__C__Q__G__V__G__G__

BstXI                     BstNI
       CCCGGCCACAAGGCCAGAGTGCTGGCCGAGGCCATGAGCCAGGCCCAGCAGACCAACATC
1081   ---------+---------+---------+---------+---------+---------+
       GGGCCGGTGTTCCGGTCTCACGACCGGCTCCGGTACTCGGTCCGGGTCGTCTGGTTGTAG
       P__G__H__K__A__R__V__L__A__E__A__M__S__Q__A__Q__Q__T__N__I__

ATGATGCAGCGGGGCAACTTCAGAGGCCAGAAGCGGATCAAGTGCTTCAACTGCGGCAAG
1141   ---------+---------+---------+---------+---------+---------+
       TACTACGTCGCCCCGTTGAAGTCTCCGGTCTTCGCCTAGTTCACGAAGTTGACGCCGTTC
       M__M__Q__R__G__N__F__R__G__Q__K__R__I__K__C__F__N__C__G__K__

BstNI        PstI      BstNI
       GAGGGCCACCTGGCCAGAAACTGCAGAGCCCCCAGGAAGAAGGGCTGCTGGAAGTGTGGC
1201   ---------+---------+---------+---------+---------+---------+
       CTCCCGGTGGACCGGTCTTTGACGTCTCGGGGGTCCTTCTTCCCGACGACCTTCACACCG
       E__G__H__L__A__R__N__C__R__A__P__R__K__K__G__C__W__K__C__G__

BstXI  BstNI
       AAGGAAGGGCACCAGATGAAGGACTGCACCGAGAGGCAGGCCAATTTCCTGGGCAAGATT
1261   ---------+---------+---------+---------+---------+---------+
       TTCCTTCCCGTGGTCTACTTCCTGACGTGGCTCTCCGTCCGGTTAAAGGACCCGTTCTAA
       K__E__G__H__Q__M__K__D__C__T__E__R__Q__A__N__F__L__G__K__I__

TGGCCTAGCAGCAAGGGCAGACCCGGCAATTTCCCCCAGAGCAGACCCGAGCCCACCGCC
1321   ---------+---------+---------+---------+---------+---------+
       ACCGGATCGTCGTTCCCGTCTGGGCCGTTAAAGGGGGTCTCGTCTGGGCTCGGGTGGCGG
       W__P__S__S__K__G__R__P__G__N__F__P__Q__S__R__P__E__P__T__A__

CCTCCCGCCGAGCTGTTCGGCATGGGCGAGGGCATCGCCAGCCTGCCCAAGCAGGAGCAG
1381   ---------+---------+---------+---------+---------+---------+
       GGAGGGCGGCTCGACAAGCCGTACCCGCTCCCGTAGCGGTCGGACGGGTTCGTCCTCGTC
       P__P__A__E__L__F__G__M__G__E__G__I__A__S__L__P__K__Q__E__Q__

BspMI       BstNI
       AAGGACAGAGAGCAGGTGCCCCCCCTGGTGTCCCTGAAGTCCCTGTTCGGCAACGATCCT
1441   ---------+---------+---------+---------+---------+---------+
       TTCCTGTCTCTCGTCCACGGGGGGGACCACAGGGACTTCAGGGACAAGCCGTTGCTAGGA
       K__D__R__E__Q__V__P__P__L__V__S__L__K__S__L__F__G__N__D__P__
```

FIG. 16C

```
                BstNI    NcoI                                              BstNI
                   BamHI                           BsaI         BstEII
           CTGAGCCAGGGATCCATGGCCCCCCAGATCACCCTGTGGCAGAGACCCCTGGTGACCGTG
      1501 ---------+---------+---------+---------+---------+---------+
           GACTCGGTCCCTAGGTACCGGGGGGTCTAGTGGGACACCGTCTCTGGGGACCACTGGCAC
           L  S  Q  G  S  M  A  P  Q  I  T  L  W  Q  R  P  L  V  T  V

NarI
                                                          KasI
                         PvuII                            HaeII
           AAGATCGGCGGCCAGCTGAAGGAAGCCCTGCTGGATACAGGCGCCGATGATACCGTGCTG
      1561 ---------+---------+---------+---------+---------+---------+
           TTCTAGCCGCCGGTCGACTTCCTTCGGGACGACCTATGTCCGCGGCTACTATGGCACGAC
           K  I  G  G  Q  L  K  E  A  L  L  D  T  G  A  D  D  T  V  L

BspMI
           GAGGACATCAACCTGCCCGGCAAGTGGAAGCCTAGAATGATCGGCGGCATCGGGGGCTTC
      1621 ---------+---------+---------+---------+---------+---------+
           CTCCTGTAGTTGGACGGGCCGTTCACCTTCGGATCTTACTAGCCGCCGTAGCCCCCGAAG
           E  D  I  N  L  P  G  K  W  K  P  R  M  I  G  G  I  G  G  F

ATCAAAGTGAAGCAGTACGACCAGATCCTGATCGAGATTTGCGGGAAGAAGGCCATCGGC
      1681 ---------+---------+---------+---------+---------+---------+
           TAGTTTCACTTCGTCATGCTGGTCTAGGACTAGCTCTAAACGCCCTTCTTCCGGTAGCCG
           I  K  V  K  Q  Y  D  Q  I  L  I  E  I  C  G  K  K  A  I  G

ApaI                         EagI
           ACCGTGCTGGTGGGCCCCACCCCTGTGAATATCATCGGCCGGAACATGCTGACCCAGATC
      1741 ---------+---------+---------+---------+---------+---------+
           TGGCACGACCACCCGGGGTGGGGACACTTATAGTAGCCGGCCTTGTACGACTGGGTCTAG
           T  V  L  V  G  P  T  P  V  N  I  I  G  R  N  M  L  T  Q  I

BsaI
           GGCTGCACCCTGAACTTCCCCATCAGCCCCATCGAGACCGTGCCCGTGACCCTGAAGCCC
      1801 ---------+---------+---------+---------+---------+---------+
           CCGACGTGGGACTTGAAGGGGTAGTCGGGGTAGCTCTGGCACGGGCACTGGGACTTCGGG
           G  C  T  L  N  F  P  I  S  P  I  E  T  V  P  V  T  L  K  P

GGCATGGATGGCCCCAAAGTGAAACAGTGGCCCCTGACCGAGGAGAAGATTAAGGCCCTG
      1861 ---------+---------+---------+---------+---------+---------+
           CCGTACCTACCGGGGTTTCACTTTGTCACCGGGGACTGGCTCCTCTTCTAATTCCGGGAC
           G  M  D  G  P  K  V  K  Q  W  P  L  T  E  E  K  I  K  A  L

ACCGAAATCTGTACCGAGATGGAGAAGGAGGGCAAGATCAGCAAGATCGGCCCCGAGAAC
      1921 ---------+---------+---------+---------+---------+---------+
           TGGCTTTAGACATGGCTCTACCTCTTCCTCCCGTTCTAGTCGTTCTAGCCGGGGCTCTTG
           T  E  I  C  T  E  M  E  K  E  G  K  I  S  K  I  G  P  E  N

CCCTACAACACCCCCATCTTCGCCATCAAGAAGAAGGACAGCACCAAGTGGCGGAAACTG
      1981 ---------+---------+---------+---------+---------+---------+
           GGGATGTTGTGGGGGTAGAAGCGGTAGTTCTTCTTCCTGTCGTGGTTCACCGCCTTTGAC
           P  Y  N  T  P  I  F  A  I  K  K  K  D  S  T  K  W  R  K  L
```

FIG. 16D

```
                              BstNI                         PvuII
       GTGGACTTCCGGGAGCTGAACAAGAGGACCCAGGACTTCTGGGAAGTGCAGCTGGGCATC
2041   ---------+---------+---------+---------+---------+---------+
       CACCTGAAGGCCCTCGACTTGTTCTCCTGGGTCCTGAAGACCCTTCACGTCGACCCGTAG
       V__D__F__R__E__L__N__K__R__T__Q__D__F__W__E__V__Q__L__G__I__

CCCCACCCTGCCGGCCTGAAGAAGAAGAAGTCCGTGACAGTGCTGGATGTGGGCGACGCC
2101   ---------+---------+---------+---------+---------+---------+
       GGGGTGGGACGGCCGGACTTCTTCTTCTTCAGGCACTGTCACGACCTACACCCGCTGCGG
       P__H__P__A__G__L__K__K__K__K__S__V__T__V__L__D__V__G__D__A__

BstNI
       TACTTCAGCGTGCCCCTGGACGAGAACTTCAGGAAGTACACCGCCTTCACCATCCCCAGC
2161   ---------+---------+---------+---------+---------+---------+
       ATGAAGTCGCACGGGGACCTGCTCTTGAAGTCCTTCATGTGGCGGAAGTGGTAGGGGTCG
       Y__F__S__V__P__L__D__E__N__F__R__K__Y__T__A__F__T__I__P__S__

BsaI
       ACCAACAACGAGACCCCCGGAGTGAGATACCAGTACAACGTGCTGCCTCAGGGCTGGAAG
2221   ---------+---------+---------+---------+---------+---------+
       TGGTTGTTGCTCTGGGGGCCTCACTCTATGGTCATGTTGCACGACGGAGTCCCGACCTTC
       T__N__N__E__T__P__G__V__R__Y__Q__Y__N__V__L__P__Q__G__W__K__

BstXI   BstNI
       GGCAGCCCCGCCATCTTCCAGAGCAGCATGACCAAGATCCTGGAGCCCTTCCGGAGCAAG
2281   ---------+---------+---------+---------+---------+---------+
       CCGTCGGGGCGGTAGAAGGTCTCGTCGTACTGGTTCTAGGACCTCGGGAAGGCCTCGTTC
       G__S__P__A__I__F__Q__S__S__M__T__K__I__L__E__P__F__R__S__K__

PflMI
       AACCCCGAGATCATCATCTACCAGTACATGGCCGCCCTGTATGTGGGCAGCGATCTGGAG
2341   ---------+---------+---------+---------+---------+---------+
       TTGGGGCTCTAGTAGTAGATGGTCATGTACCGGCGGGACATACACCCGTCGCTAGACCTC
       N__P__E__I__I__I__Y__Q__Y__M__A__A__L__Y__V__G__S__D__L__E__

ApaI  BspMI
       ATCGGCCAGCACAGGACCAAGATCGAAGAGCTGAGGGCCCACCTGCTGAGCTGGGGCTTC
2401   ---------+---------+---------+---------+---------+---------+
       TAGCCGGTCGTGTCCTGGTTCTAGCTTCTCGACTCCCGGGTGGACGACTCGACCCCGAAG
       I__G__Q__H__R__T__K__I__E__E__L__R__A__H__L__L__S__W__G__F__

ACCACCCCCGATAAGAAGCACCAGAAGGAGCCCCCTTTCCTGTGGATGGGCTACGAGCTG
2461   ---------+---------+---------+---------+---------+---------+
       TGGTGGGGGCTATTCTTCGTGGTCTTCCTCGGGGGAAAGGACACCTACCCGATGCTCGAC
       T__T__P__D__K__K__H__Q__K__E__P__P__F__L__W__M__G__Y__E__L__

CACCCCGATAAGTGGACCGTGCAGCCCATCATGCTGCCCGATAAGGAGAGCTGGACCGTG
2521   ---------+---------+---------+---------+---------+---------+
       GTGGGGCTATTCACCTGGCACGTCGGGTAGTACGACGGGCTATTCCTCTCGACCTGGCAC
       H__P__D__K__W__T__V__Q__P__I__M__L__P__D__K__E__S__W__T__V__
```

FIG. 16E

```
              PflMI
       AACGACATCCAGAAACTGGTGGGCAAGCTGAATTGGGCCAGCCAAATCTACGCCGGCATT
2581   ---------+---------+---------+---------+---------+---------+
       TTGCTGTAGGTCTTTGACCACCCGTTCGACTTAACCCGGTCGGTTTAGATGCGGCCGTAA
        N   D   I   Q   K   L   V   G   K   L   N   W   A   S   Q   I   Y   A   G   I

NarI
                                          KasI
           PvuII                           HaeII
       AAAGTGAAGCAGCTGTGCAGGCTGCTGAGAGGCGCCAAAGCCCTGACAGACATCGTGACA
2641   ---------+---------+---------+---------+---------+---------+
       TTTCACTTCGTCGACACGTCCGACGACTCTCCGCGGTTTCGGGACTGTCTGTAGCACTGT
        K   V   K   Q   L   C   R   L   L   R   G   A   K   A   L   T   D   I   V   T

CTGACAGAGGAGGCCGAGCTGGAGCTGGCCGAGAACAGGGAGATCCTGAAGGACCCCGTG
2701   ---------+---------+---------+---------+---------+---------+
       GACTGTCTCCTCCGGCTCGACCTCGACCGGCTCTTGTCCCTCTAGGACTTCCTGGGGCAC
        L   T   E   E   A   E   L   E   L   A   E   N   R   E   I   L   K   D   P   V

BstNI         HinfI         BstNI
       CACGGCGTGTACTACGACCCCAGCAAGGACCTGGTGGCCGAGATTCAGAAGCAGGGCCAG
2761   ---------+---------+---------+---------+---------+---------+
       GTGCCGCACATGATGCTGGGGTCGTTCCTGGACCACCGGCTCTAAGTCTTCGTCCCGGTC
        H   G   V   Y   Y   D   P   S   K   D   L   V   A   E   I   Q   K   Q   G   Q BstNI
       GACCAGTGGACCTACCAAATCTACCAGGAGCCTTTCAAGAACCTGAAAACCGGGAAGTAC
2821   ---------+---------+---------+---------+---------+---------+
       CTGGTCACCTGGATGGTTTAGATGGTCCTCGGAAAGTTCTTGGACTTTTGGCCCTTCATG
        D   Q   W   T   Y   Q   I   Y   Q   E   P   F   K   N   L   K   T   G   K   Y BstNI        HaeII                    PvuII
       GCCAGGAAGAGAAGCGCCCACACCAACGATGTGAGGCAGCTGGCCGAAGTGGTGCAGAAA
2881   ---------+---------+---------+---------+---------+---------+
       CGGTCCTTCTCTTCGCGGGTGTGGTTGCTACACTCCGTCGACCGGCTTCACCACGTCTTT
        A   R   K   R   S   A   H   T   N   D   V   R   Q   L   A   E   V   V   Q   K GTGGCTATGGAGAGCATCGTGATCTGGGGCAAGACCCCCAAGTTCAAGCTGCCCATCCAG
2941   ---------+---------+---------+---------+---------+---------+
       CACCGATACCTCTCGTAGCACTAGACCCCGTTCTGGGGGTTCAAGTTCGACGGGTAGGTC
        V   A   M   E   S   I   V   I   W   G   K   T   P   K   F   K   L   P   I   Q BstNI                                      HinfI
        BsaI        BstNI                         BstNI
       AAGGAGACCTGGGAAACCTGGTGGATGGACTACTGGCAGGCCACCTGGATTCCTGAGTGG
3001   ---------+---------+---------+---------+---------+---------+
       TTCCTCTGGACCCTTTGGACCACCTACCTGATGACCGTCCGGTGGACCTAAGGACTCACC
        K   E   T   W   E   T   W   W   M   D   Y   W   Q   A   T   W   I   P   E   W
```

FIG. 16F

```
                                            PvuII                   BstNI
         GAGTTCGTGAACACCCCCCCTCTGGTGAAGCTGTGGTATCAGCTGGAGAAGGACCCCATC
3061     ---------+---------+---------+---------+---------+---------+
         CTCAAGCACTTGTGGGGGGGAGACCACTTCGACACCATAGTCGACCTCTTCCTGGGGTAG
          E  F  V  N  T  P  P  L  V  K  L  W  Y  Q  L  E  K  D  P  I

NarI
            KasI
            HaeII BsaI                                    BsaI
         CTGGGCGCCGAGACCTTCTACGTGGACGGAGCCGCCAATAGAGAGACCAAGCTGGGCAAG
3121     ---------+---------+---------+---------+---------+---------+
         GACCCGCGGCTCTGGAAGATGCACCTGCCTCGGCGGTTATCTCTCTGGTTCGACCCGTTC
          L  G  A  E  T  F  Y  V  D  G  A  A  N  R  E  T  K  L  G  K

GCCGGCTACGTGACCGACAGAGGCAGACAGAAAGTGGTGTCTCTGACCGAGACAACCAAC
3181     ---------+---------+---------+---------+---------+---------+
         CGGCCGATGCACTGGCTGTCTCCGTCTGTCTTTCACCACAGAGACTGGCTCTGTTGGTTG
          A  G  Y  V  T  D  R  G  R  Q  K  V  V  S  L  T  E  T  T  N

BstXI           PstI
         CAGAAAACCGAGCTGCACGCCATCCTGCTGGCCCTGCAGGACAGCGGCAGCGAAGTGAAC
3241     ---------+---------+---------+---------+---------+---------+
         GTCTTTTGGCTCGACGTGCGGTAGGACGACCGGGACGTCCTGTCGCCGTCGCTTCACTTG
          Q  K  T  E  L  H  A  I  L  L  A  L  Q  D  S  G  S  E  V  N

HinfI         BstNI
         ATCGTGACCGACTCCCAGTACGCCCTGGGCATCATTCAGGCCCAGCCCGATAGAAGCGAG
3301     ---------+---------+---------+---------+---------+---------+
         TAGCACTGGCTGAGGGTCATGCGGGACCCGTAGTAAGTCCGGGTCGGGCTATCTTCGCTC
          I  V  T  D  S  Q  Y  A  L  G  I  I  Q  A  Q  P  D  R  S  E AGCGAGCTGGTGAACCAGATCATCGAGAAGCTGATCGGCAAGGACAAAATCTACCTGAGC
3361     ---------+---------+---------+---------+---------+---------+
         TCGCTCGACCACTTGGTCTAGTAGCTCTTCGACTAGCCGTTCCTGTTTTAGATGGACTCG
          S  E  L  V  N  Q  I  I  E  K  L  I  G  K  D  K  I  Y  L  S BspMI
         TGGGTGCCCGCCCACAAGGGCATCGGCGGCAACGAGCAGGTGGACAAGCTGGTGTCCAGC
3421     ---------+---------+---------+---------+---------+---------+
         ACCCACGGGCGGGTGTTCCCGTAGCCGCCGTTGCTCGTCCACCTGTTCGACCACAGGTCG
          W  V  P  A  H  K  G  I  G  G  N  E  Q  V  D  K  L  V  S  S BstNI
         GGCATCCGGAAAGTGCTGTTTCTGGACGGCATCGACAAGGCCCAGGAGGACCACGAGAGA
3481     ---------+---------+---------+---------+---------+---------+
         CCGTAGGCCTTTCACGACAAAGACCTGCCGTAGCTGTTCCGGGTCCTCCTGGTGCTCTCT
          G  I  R  K  V  L  F  L  D  G  I  D  K  A  Q  E  D  H  E  R
```

FIG. 16G

```
                                        BspMI
              TACCACAGCAACTGGCGGACAATGGCCAGCGACTTCAACCTGCCTCCCATCGTGGCCAAG
       3541   ---------+---------+---------+---------+---------+---------+
              ATGGTGTCGTTGACCGCCTGTTACCGGTCGCTGAAGTTGGACGGAGGGTAGCACCGGTTC
               Y  H  S  N  W  R  T  M  A  S  D  F  N  L  P  P  I  V  A  K

PvuII           PvuII                       BstNI
              GAGATCGTGGCCAGCTGCGATAAGTGTCAGCTGAAGGGCGAGGCCATGCACGGCCAGGTG
       3601   ---------+---------+---------+---------+---------+---------+
              CTCTAGCACCGGTCGACGCTATTCACAGTCGACTTCCCGCTCCGGTACGTGCCGGTCCAC
               E  I  V  A  S  C  D  K  C  Q  L  K  G  E  A  M  H  G  Q  V

PstI BstNI       PvuII               BstNI          HinfI
              GACTGCAGCCCTGGCATCTGGCAGCTGGCCTGCACCCACCTGGAGGGCAAAGTGATTCTG
       3661   ---------+---------+---------+---------+---------+---------+
              CTGACGTCGGGACCGTAGACCGTCGACCGGACGTGGGTGGACCTCCCGTTTCACTAAGAC
               D  C  S  P  G  I  W  Q  L  A  C  T  H  L  E  G  K  V  I  L HinfI     BsaI        BstNI
              GTGGCCGTGCACGTGGCCAGCGGCTACATCGAGGCCGAAGTGATTCCCGCCGAGACCGGC
       3721   ---------+---------+---------+---------+---------+---------+
              CACCGGCACGTGCACCGGTCGCCGATGTAGCTCCGGCTTCACTAAGGGCGGCTCTGGCCG
               V  A  V  H  V  A  S  G  Y  I  E  A  E  V  I  P  A  E  T  G BsaI
              CAGGAGACCGCCTACTTCCTGCTGAAGCTGGCCGGCAGATGGCCCGTGAAAGTGGTGCAC
       3781   ---------+---------+---------+---------+---------+---------+
              GTCCTCTGGCGGATGAAGGACGACTTCGACCGGCCGTCTACCGGGCACTTTCACCACGTG
               Q  E  T  A  Y  F  L  L  K  L  A  G  R  W  P  V  K  V  V  H ACCGCCAACGGCAGCAACTTCACCTCTGCCGCCGTGAAGGCCGCCTGTTGGTGGGCCAAT
       3841   ---------+---------+---------+---------+---------+---------+
              TGGCGGTTGCCGTCGTTGAAGTGGAGACGGCGGCACTTCCGGCGGACAACCACCCGGTTA
               T  A  N  G  S  N  F  T  S  A  A  V  K  A  A  C  W  W  A  N PflMI
                                                       BstNI
              ATCCAGCAGGAGTTCGGCATCCCCTACAACCCTCAGAGCCAGGGCGTGGTGGCCAGCATG
       3901   ---------+---------+---------+---------+---------+---------+
              TAGGTCGTCCTCAAGCCGTAGGGGATGTTGGGAGTCTCGGTCCCGCACCACCGGTCGTAC
               I  Q  Q  E  F  G  I  P  Y  N  P  Q  S  Q  G  V  V  A  S  M BstNI           BstNI
              AACAAGGAGCTGAAGAAGATCATCGGCCAGGTGAGGGACCAGGCCGAGCACCTGAAAACA
       3961   ---------+---------+---------+---------+---------+---------+
              TTGTTCCTCGACTTCTTCTAGTAGCCGGTCCACTCCCTGGTCCGGCTCGTGGACTTTTGT
               N  K  E  L  K  K  I  I  G  Q  V  R  D  Q  A  E  H  L  K  T GCCGTGCAGATGGCCGTGTTCATCCACAACTTCAAGCGGAAGGGCGGCATTGGCGGCTAC
       4021   ---------+---------+---------+---------+---------+---------+
              CGGCACGTCTACCGGCACAAGTAGGTGTTGAAGTTCGCCTTCCCGCCGTAACCGCCGATG
               A  V  Q  M  A  V  F  I  H  N  F  K  R  K  G  G  I  G  G  Y
```

FIG. 16H

```
         HaeII                                  EcoRV           PstI
         AGCGCCGGAGAGCGGATCATCGACATCATCGCCACCGATATCCAGACCAAGGAACTGCAG
    4081 ---------+---------+---------+---------+---------+---------+
         TCGCGGCCTCTCGCCTAGTAGCTGTAGTAGCGGTGGCTATAGGTCTGGTTCCTTGACGTC
          S   A   G   E   R   I   I   D   I   I   A   T   D   I   Q   T   K   E   L   Q

HinfI
         AAGCAGATCACCAAGATTCAGAACTTCAGAGTGTACTACCGGGACAGCAGGGACCCCATC
    4141 ---------+---------+---------+---------+---------+---------+
         TTCGTCTAGTGGTTCTAAGTCTTGAAGTCTCACATGATGGCCCTGTCGTCCCTGGGGTAG
          K   Q   I   T   K   I   Q   N   F   R   V   Y   Y   R   D   S   R   D   P   I NarI
                                              KasI
              ApaI                            HaeII              BstNI
         TGGAAGGGCCCTGCCAAGCTGCTGTGGAAGGGCGAAGGCGCCGTGGTGATCCAGGACAAC
    4201 ---------+---------+---------+---------+---------+---------+
         ACCTTCCCGGGACGGTTCGACGACACCTTCCCGCTTCCGCGGCACCACTAGGTCCTGTTG
          W   K   G   P   A   K   L   L   W   K   G   E   G   A   V   V   I   Q   D   N HinfI
         AGCGACATCAAAGTGGTGCCCCGGAGGAAGGCCAAGATTCTGCGGGACTACGGCAAACAG
    4261 ---------+---------+---------+---------+---------+---------+
         TCGCTGTAGTTTCACCACGGGGCCTCCTTCCGGTTCTAAGACGCCCTGATGCCGTTTGTC
          S   D   I   K   V   V   P   R   R   K   A   K   I   L   R   D   Y   G   K   Q BglII
         ATGGCCGGCGATGACTGCGTGGCCGGCAGGCAGGATGAGGACAGATCTATGGGCGGCAAG
    4321 ---------+---------+---------+---------+---------+---------+
         TACCGGCCGCTACTGACGCACCGGCCGTCCGTCCTACTCCTGTCTAGATACCCGCCGTTC
          M   A   G   D   D   C   V   A   G   R   Q   D   E   D   R   S   M   G   G   K TGGTCCAAGGGCAGCATTGTGGGCTGGCCCGAGATCCGGGAGAGAATGAGAAGAGCCCCT
    4381 ---------+---------+---------+---------+---------+---------+
         ACCAGGTTCCCGTCGTAACACCCGACCGGGCTCTAGGCCCTCTCTTACTCTTCTCGGGGA
          W   S   K   G   S   I   V   G   W   P   E   I   R   E   R   M   R   R   A   P NarI                              NarI
                          KasI                              KasI
              BstNI       HaeII                             HaeII
         GCCGCCGCTCCTGGAGTGGGCGCCGTGTCTCAGGATCTGGATAAGCACGGCGCCATCACC
    4441 ---------+---------+---------+---------+---------+---------+
         CGGCGGCGAGGACCTCACCCGCGGCACAGAGTCCTAGACCTATTCGTGCCGCGGTAGTGG
          A   A   A   P   G   V   G   A   V   S   Q   D   L   D   K   H   G   A   I   T PvuII                BstNI
         AGCAGCAACATCAACAACCCCAGCTGTGTGTGGCTGGAGGCCCAGGAAGAGGAGGAAGTG
    4501 ---------+---------+---------+---------+---------+---------+
         TCGTCGTTGTAGTTGTTGGGGTCGACACACACCGACCTCCGGGTCCTTCTCCTCCTTCAC
          S   S   N   I   N   N   P   S   C   V   W   L   E   A   Q   E   E   E   E   V
```

FIG. 16I

```
                                                      NarI
                                                      KasI
            BsaI   BstNI           BsaI               HaeII
         GGCTTCCCTGTGAGACCCCAGGTGCCCCTGAGACCCATGACCTACAAGGGCGCCTTCGAC
   4561  ---------+---------+---------+---------+---------+---------+
         CCGAAGGGACACTCTGGGGTCCACGGGGACTCTGGGTACTGGATGTTCCCGCGGAAGCTG
          G__F__P__V__R__P__Q__V__P__L__R__P__M__T__Y__K__G__A__F__D__

BstNI
         CTGAGCCACTTCCTGAAGGAGAAGGGCGGCCTGGACGGCCTGATCTACAGCCGGAAGCGG
   4621  ---------+---------+---------+---------+---------+---------+
         GACTCGGTGAAGGACTTCCTCTTCCCGCCGGACCTGCCGGACTAGATGTCGGCCTTCGCC
          L__S__H__F__L__K__E__K__G__G__L__D__G__L__I__Y__S__R__K__R__

BstNI                     BstNI
         CAGGAGATCCTGGATCTGTGGGTGTACCACACCCAGGGCTACTTCCCCGACTGGCAGAAT
   4681  ---------+---------+---------+---------+---------+---------+
         GTCCTCTAGGACCTAGACACCCACATGGTGTGGGTCCCGATGAAGGGGCTGACCGTCTTA
          Q__E__I__L__D__L__W__V__Y__H__T__Q__G__Y__F__P__D__W__Q__N__

BstNI BstNI
         TACACCCCTGGCCCTGGAGTGCGGTATCCCCTGACCTTCGGCTGGTGCTTCAAGCTGGTG
   4741  ---------+---------+---------+---------+---------+---------+
         ATGTGGGGACCGGGACCTCACGCCATAGGGGACTGGAAGCCGACCACGAAGTTCGACCAC
          Y__T__P__G__P__G__V__R__Y__P__L__T__F__G__W__C__F__K__L__V__

CCTATGGAGCCCGACGAAGTGGAGAAGGCCACAGAGGGCGAGAACAACAGCCTGCTGCAC
   4801  ---------+---------+---------+---------+---------+---------+
         GGATACCTCGGGCTGCTTCACCTCTTCCGGTGTCTCCCGCTCTTGTTGTCGGACGACGTG
          P__M__E__P__D__E__V__E__K__A__T__E__G__E__N__N__S__L__L__H__

CCTATCTGCCAGCACGGCATGGACGATGAGGAGCGGGAAGTGCTGATCTGGAAGTTCGAC
   4861  ---------+---------+---------+---------+---------+---------+
         GGATAGACGGTCGTGCCGTACCTGCTACTCCTCGCCCTTCACGACTAGACCTTCAAGCTG
          P__I__C__Q__H__G__M__D__D__E__E__R__E__V__L__I__W__K__F__D__

BstNI
         AGCAGGCTGGCCCTGAAGCACAGAGCCCAGGAACTGCACCCAGAGTTCTACAAGGACTGC
   4921  ---------+---------+---------+---------+---------+---------+
         TCGTCCGACCGGGACTTCGTGTCTCGGGTCCTTGACGTGGGTCTCAAGATGTTCCTGACG
          S__R__L__A__L__K__H__R__A__Q__E__L__H__P__E__F__Y__K__D__C__

BclI        XbaI
         TGATGATCATAATAATCTAGAA
   4981  ---------+---------+--
         ACTACTAGTATTATTAGATCTT
          *__
```

FIG. 16J

```
         HindIII                                                    BspMI
         AAGCTTGCCGCCACCATGAGGGTGATGGAGATCCAGCGGAACTGCCAGCACCTGCTGAGA
    1    ---------+---------+---------+---------+---------+---------+
         TTCGAACGGCGGTGGTACTCCCACTACCTCTAGGTCGCCTTGACGGTCGTGGACGACTCT
                       M   R   V   M   E   I   Q   R   N   C   Q   H   L   L   R BstNI                 PstI                         BstEII
         TGGGGCATCATGATCCTGGGCATGATTATCATCTGCAGCACCGCCGACAACCTGTGGGTG
    61   ---------+---------+---------+---------+---------+---------+
         ACCCCGTAGTACTAGGACCCGTACTAATAGTAGACGTCGTGGCGGCTGTTGGACACCCAC
          W   G   I   M   I   L   G   M   I   I   I   C   S   T   A   D   N   L   W   V BsaI
         ACCGTGTACTACGGCGTGCCTGTGTGGAGAGATGCCGAGACCACCCTGTTCTGCGCCAGC
    121  ---------+---------+---------+---------+---------+---------+
         TGGCACATGATGCCGCACGGACACACCTCTCTACGGCTCTGGTGGGACAAGACGCGGTCG
           T   V   Y   Y   G   V   P   V   W   R   D   A   E   T   T   L   F   C   A   S StuI
         GACGCCAAGGCCTACAGCACCGAGAAGCACAATGTGTGGGCCACCCACGCCTGCGTGCCT
    181  ---------+---------+---------+---------+---------+---------+
         CTGCGGTTCCGGATGTCGTGGCTCTTCGTGTTACACACCCGGTGGGTGCGGACGCACGGA
           D   A   K   A   Y   S   T   E   K   H   N   V   W   A   T   H   A   C   V   P BstNI
         ACCGATCCCAACCCTCAGGAGATCCCCCTGGACAACGTGACCGAGGAGTTCAACATGTGG
    241  ---------+---------+---------+---------+---------+---------+
         TGGCTAGGGTTGGGAGTCCTCTAGGGGGACCTGTTGCACTGGCTCCTCAAGTTGTACACC
           T   D   P   N   P   Q   E   I   P   L   D   N   V   T   E   E   F   N   M   W AAGAACAACATGGTGGACCAGATGCACGAGGACATCATCAGCCTGTGGGACCAGAGCCTG
    301  ---------+---------+---------+---------+---------+---------+
         TTCTTGTTGTACCACCTGGTCTACGTGCTCCTGTAGTAGTCGGACACCCTGGTCTCGGAC
           K   N   N   M   V   D   Q   M   H   E   D   I   I   S   L   W   D   Q   S   L PvuII                              PstI
         AAGCCCTGCGTGCAGCTGACCCCCCTGTGCGTGACCCTGAACTGCAGCAACGCCAGAGTG
    361  ---------+---------+---------+---------+---------+---------+
         TTCGGGACGCACGTCGACTGGGGGGACACGCACTGGGACTTGACGTCGTTGCGGTCTCAC
           K   P   C   V   Q   L   T   P   L   C   V   T   L   N   C   S   N   A   R   V PstI
         AACGCCACCTTCAACTCCACCGAGGACAGGGAGGGCATGAAGAACTGCAGCTTCAACATG
    421  ---------+---------+---------+---------+---------+---------+
         TTGCGGTGGAAGTTGAGGTGGCTCCTGTCCCTCCCGTACTTCTTGACGTCGAAGTTGTAC
           N   A   T   F   N   S   T   E   D   R   E   G   M   K   N   C   S   F   N   M BspMI
         ACCACCGAGCTGCGGGATAAGAAGCAGCAGGTGTACAGCCTGTTCTACCGGCTGGACATC
    481  ---------+---------+---------+---------+---------+---------+
         TGGTGGCTCGACGCCCTATTCTTCGTCGTCCACATGTCGGACAAGATGGCCGACCTGTAG
           T   T   E   L   R   D   K   K   Q   Q   V   Y   S   L   F   Y   R   L   D   I
```

FIG. 17A

```
                                                                      HaeII
      GAGAAGATCAACAGCAGCAACAACAACAGCGAGTACCGGCTGGTGAACTGCAATACCAGC
 541  ---------+---------+---------+---------+---------+---------+
      CTCTTCTAGTTGTCGTCGTTGTTGTTGTCGCTCATGGCCGACCACTTGACGTTATGGTCG
       E  K  I  N  S  S  N  N  N  S  E  Y  R  L  V  N  C  N  T  S

StuI
           BstNI         BstEII
      GCCATCACCCAGGCCTGCCCTAAGGTGACCTTCGAGCCCATCCCCATCCACTACTGCGCC
 601  ---------+---------+---------+---------+---------+---------+
      CGGTAGTGGGTCCGGACGGGATTCCACTGGAAGCTCGGGTAGGGGTAGGTGATGACGCGG
       A  I  T  Q  A  C  P  K  V  T  F  E  P  I  P  I  H  Y  C  A

CCTGCCGGCTTCGCCATCCTGAAGTGCAACGACACCGAGTTCAATGGCACCGGCCCCTGC
 661  ---------+---------+---------+---------+---------+---------+
      GGACGGCCGAAGCGGTAGGACTTCACGTTGCTGTGGCTCAAGTTACCGTGGCCGGGGACG
       P  A  G  F  A  I  L  K  C  N  D  T  E  F  N  G  T  G  P  C

PvuII
      AAGAATGTGAGCACCGTGCAGTGCACCCACGGCATCAAGCCCGTGGTGTCCACCCAGCTG
 721  ---------+---------+---------+---------+---------+---------+
      TTCTTACACTCGTGGCACGTCACGTGGGTGCCGTAGTTCGGGCACCACAGGTGGGTCGAC
       K  N  V  S  T  V  Q  C  T  H  G  I  K  P  V  V  S  T  Q  L

BstNI
      CTGCTGAACGGCAGCCTGGCCGAGAGAGAAGTGCGGATCAGGAGCGAGAACATCGCCAAC
 781  ---------+---------+---------+---------+---------+---------+
      GACGACTTGCCGTCGGACCGGCTCTCTCTTCACGCCTAGTCCTCGCTCTTGTAGCGGTTG
       L  L  N  G  S  L  A  E  R  E  V  R  I  R  S  E  N  I  A  N

AACGCCAAGAACATCATCGTGCAGTTCGCCAGCCCCGTGAAGATCAACTGCATCCGGCCC
 841  ---------+---------+---------+---------+---------+---------+
      TTGCGGTTCTTGTAGTAGCACGTCAAGCGGTCGGGGCACTTCTAGTTGACGTAGGCCGGG
       N  A  K  N  I  I  V  Q  F  A  S  P  V  K  I  N  C  I  R  P

HinfI    BstNI
      AACAACAATACCCGGAAGAGCTACAGAATCGGCCCTGGCCAGACCTTCTACGCCACCGAC
 901  ---------+---------+---------+---------+---------+---------+
      TTGTTGTTATGGGCCTTCTCGATGTCTTAGCCGGGACCGGTCTGGAAGATGCGGTGGCTG
       N  N  N  T  R  K  S  Y  R  I  G  P  G  Q  T  F  Y  A  T  D BstNI
      ATTGTGGGCGACATCAGACAGGCCCACTGCAACGTGTCCAGGACCGACTGGAACAACACC
 961  ---------+---------+---------+---------+---------+---------+
      TAACACCCGCTGTAGTCTGTCCGGGTGACGTTGCACAGGTCCTGGCTGACCTTGTTGTGG
       I  V  G  D  I  R  Q  A  H  C  N  V  S  R  T  D  W  N  N  T PvuII      ScaI
      CTGAGACTGGTGGCCAACCAGCTGCGGAAGTACTTCAGCAACAAGACCATCATCTTCACC
1021  ---------+---------+---------+---------+---------+---------+
      GACTCTGACCACCGGTTGGTCGACGCCTTCATGAAGTCGTTGTTCTGGTAGTAGAAGTGG
       L  R  L  V  A  N  Q  L  R  K  Y  F  S  N  K  T  I  I  F  T
```

FIG. 17B

```
                       BstNI
            BsaI
       AACAGCAGCGGCGGAGACCTGGAGATCACCACCCACAGCTTCAATTGTGGCGGCGAGTTC
 1081  ---------+---------+---------+---------+---------+---------+
       TTGTCGTCGCCGCCTCTGGACCTCTAGTGGTGGGTGTCGAAGTTAACACCGCCGCTCAAG
        N  S  S  G  G  D  L  E  I  T  T  H  S  F  N  C  G  G  E  F

BstNI                HinfI
       TTCTACTGCAACACCTCCGGCCTGTTCAATAGCACCTGGACCACCAACAACATGCAGGAG
 1141  ---------+---------+---------+---------+---------+---------+
       AAGATGACGTTGTGGAGGCCGGACAAGTTATCGTGGACCTGGTGGTTGTTGTACGTCCTC
        F  Y  C  N  T  S  G  L  F  N  S  T  W  T  T  N  N  M  Q  E TCCAACGACACCAGCAACGGCACCATCACCCTGCCCTGCCGGATCAAGCAGATCATCCGG
 1201  ---------+---------+---------+---------+---------+---------+
       AGGTTGCTGTGGTCGTTGCCGTGGTAGTGGGACGGGACGGCCTAGTTCGTCTAGTAGGCC
        S  N  D  T  S  N  G  T  I  T  L  P  C  R  I  K  Q  I  I  R BstNI                              HinfI
       ATGTGGCAGCGCGTGGGCCAGGCCATGTACGCCCCTCCCATCGAGGGCGTGATTCGCTGC
 1261  ---------+---------+---------+---------+---------+---------+
       TACACCGTCGCGCACCCGGTCCGGTACATGCGGGGAGGGTAGCTCCCGCACTAAGCGACG
        M  W  Q  R  V  G  Q  A  M  Y  A  P  P  I  E  G  V  I  R  C GAGAGCAACATCACCGGCCTGATCCTGACCAGAGATGGCGGCAACAACAATTCCGCCAAC
 1321  ---------+---------+---------+---------+---------+---------+
       CTCTCGTTGTAGTGGCCGGACTAGGACTGGTCTCTACCGCCGTTGTTGTTAAGGCGGTTG
        E  S  N  I  T  G  L  I  L  T  R  D  G  G  N  N  N  S  A  N BsaI        BstNI       EcoRV
       GAGACCTTCAGACCTGGCGGCGGAGATATATCCGGGACAACTGGCGGAGCGAGCTGTACAAG
 1381  ---------+---------+---------+---------+---------+---------+
       CTCTGGAAGTCTGGACCGCCGCCTCTATAGGCCCTGTTGACCGCCTCGCTCGACATGTTC
        E  T  F  R  P  G  G  G  D  I  R  D  N  W  R  S  E  L  Y  K BstNI
       TACAAGGTGGTGAAGATCGAGCCCCTGGGCGTGGCCCCCACCAGAGCCAAGAGAAGAGTG
 1441  ---------+---------+---------+---------+---------+---------+
       ATGTTCCACCACTTCTAGCTCGGGGACCCGCACCGGGGGTGGTCTCGGTTCTCTTCTCAC
        Y  K  V  V  K  I  E  P  L  G  V  A  P  T  R  A  K  R  R  V NarI
                                KasI
                                HaeII                      BstNI
       GTGGAGCGGGAGAAGAGAGCCGTGGGCATCGGCGCCGTGTTTCTGGGCTTCCTGGGAGCC
 1501  ---------+---------+---------+---------+---------+---------+
       CACCTCGCCCTCTTCTCTCGGCACCCGTAGCCGCGGCACAAAGACCCGAAGGACCCTCGG
        V  E  R  E  K  R  A  V  G  I  G  A  V  F  L  G  F  L  G  A
```

FIG. 17C

```
                                                                PvuII
     GCCGGATCTACAATGGGAGCCGCCAGCATCACCCTGACCGTGCAGGCCAGACAGCTGCTG
1561 ---------+---------+---------+---------+---------+---------+
     CGGCCTAGATGTTACCCTCGGCGGTCGTAGTGGGACTGGCACGTCCGGTCTGTCGACGAC
      A  G  S  T  M  G  A  A  S  I  T  L  T  V  Q  A  R  Q  L  L

PvuII
     AGCGGCATCGTGCAGCAGCAGAGCAATCTGCTGAGAGCCATCGAGGCCCAGCAGCAGCTG
1621 ---------+---------+---------+---------+---------+---------+
     TCGCCGTAGCACGTCGTCGTCTCGTTAGACGACTCTCGGTAGCTCCGGGTCGTCGTCGAC
      S  G  I  V  Q  Q  Q  S  N  L  L  R  A  I  E  A  Q  Q  Q  L

PvuII       BstXI
                                PstI    BstNI
     CTGAAGCTGACAGTGTGGGGCATCAAGCAGCTGCAGGCCAGGGTGCTGGCCGTGGAGAGA
1681 ---------+---------+---------+---------+---------+---------+
     GACTTCGACTGTCACACCCCGTAGTTCGTCGACGTCCGGTCCCACGACCGGCACCTCTCT
      L  K  L  T  V  W  G  I  K  Q  L  Q  A  R  V  L  A  V  E  R

BstNI             PstI
     TACCTGAGGGACCAGCAGCTCCTGGGCATCTGGGGCTGCAGCGGCAAGCTGATCTGCACC
1741 ---------+---------+---------+---------+---------+---------+
     ATGGACTCCCTGGTCGTCGAGGACCCGTAGACCCCGACGTCGCCGTTCGACTAGACGTGG
      Y  L  R  D  Q  Q  L  L  G  I  W  G  C  S  G  K  L  I  C  T

BstNI        PvuII
     ACCAACGTGCCCTGGAATAGCAGCTGGAGCAACAAGAGCTACGACGACATCTGGCAGAAC
1801 ---------+---------+---------+---------+---------+---------+
     TGGTTGCACGGGACCTTATCGTCGACCTCGTTGTTCTCGATGCTGCTGTAGACCGTCTTG
      T  N  V  P  W  N  S  S  W  S  N  K  S  Y  D  D  I  W  Q  N

PstI
       BstNI
     ATGACCTGGCTGCAGTGGGACAAGGAGATCAGCAACTACACCGACATCATCTACAGCCTG
1861 ---------+---------+---------+---------+---------+---------+
     TACTGGACCGACGTCACCCTGTTCCTCTAGTCGTTGATGTGGCTGTAGTAGATGTCGGAC
      M  T  W  L  Q  W  D  K  E  I  S  N  Y  T  D  I  I  Y  S  L

BstNI
     ATCGAGGAGAGCCAGAACCAGCAGGAGAAGAACGAGCAGGATCTGCTGGCCCTGGACAAG
1921 ---------+---------+---------+---------+---------+---------+
     TAGCTCCTCTCGGTCTTGGTCGTCCTCTTCTTGCTCGTCCTAGACGACCGGGACCTGTTC
      I  E  E  S  Q  N  Q  Q  E  K  N  E  Q  D  L  L  A  L  D  K

PflMI                                               BglII
     TGGGCCAACCTGTGGAACTGGTTCGACATCAGCAAGTGGCTGTGGTACATCAGATCTTGA
1981 ---------+---------+---------+---------+---------+---------+
     ACCCGGTTGGACACCTTGACCAAGCTGTAGTCGTTCACCGACACCATGTAGTCTAGAACT
      W  A  N  L  W  N  W  F  D  I  S  K  W  L  W  Y  I  R  S  *

XbaI
     TAATCTAGAA
2041 ---------+
     ATTAGATCTT
```

FIG. 17D

SEQUENCE LISTING

```
<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Phe Leu Gly
  1

<210> SEQ ID NO 2
<211> LENGTH: 499
<212> TYPE: PRT
<213> ORGANISM: Human immunodeficiency virus type 1
<220> FEATURE:
<221> NAME/KEY: MOD_RES
<222> LOCATION: (124)
<223> OTHER INFORMATION: Variable amino acid
<220> FEATURE:
<221> NAME/KEY: MOD_RES
<222> LOCATION: (146)
<223> OTHER INFORMATION: Variable amino acid
<220> FEATURE:
<221> NAME/KEY: MOD_RES
<222> LOCATION: (339)
<223> OTHER INFORMATION: Variable amino acid
<220> FEATURE:
<221> NAME/KEY: MOD_RES
<222> LOCATION: (481)..(482)
<223> OTHER INFORMATION: Variable amino acid

<400> SEQUENCE: 2

Met Gly Ala Arg Ala Ser Val Leu Ser Gly Gly Lys Leu Asp Ala Trp
  1               5                  10                  15

Glu Lys Ile Arg Leu Arg Pro Gly Gly Lys Lys Lys Tyr Arg Leu Lys
                 20                  25                  30

His Leu Val Trp Ala Ser Arg Glu Leu Glu Arg Phe Ala Leu Asn Pro
             35                  40                  45

Ser Leu Leu Glu Thr Ala Glu Gly Cys Gln Gln Ile Met Glu Gln Leu
     50                  55                  60

Gln Pro Ala Leu Lys Thr Gly Thr Glu Glu Leu Arg Ser Leu Phe Asn
 65                  70                  75                  80
```

```
Thr Val Ala Thr Leu Tyr Cys Val His Gln Arg Ile Asp Val Lys Asp
                85              90                  95

Thr Lys Glu Ala Leu Asp Lys Ile Glu Ile Gln Asn Lys Ser Lys
            100             105                 110

Gln Lys Thr Gln Gln Ala Ala Asp Thr Gly Xaa Ser Ser Lys Val
            115             120             125

Ser Gln Asn Tyr Pro Ile Val Gln Asn Ala Gln Gly Gln Met Ile His
    130             135                 140

Gln Xaa Leu Ser Pro Arg Thr Leu Asn Ala Trp Val Lys Val Ile Glu
145                 150             155                 160

Glu Lys Ala Phe Ser Pro Glu Val Ile Pro Met Phe Ser Ala Leu Ser
                165             170                 175

Glu Gly Ala Thr Pro Gln Asp Leu Asn Met Met Leu Asn Ile Val Gly
            180             185                 190

Gly His Gln Ala Ala Met Gln Met Leu Lys Asp Thr Ile Asn Glu Glu
    195             200             205

Ala Ala Glu Trp Asp Arg Leu His Pro Val His Ala Gly Pro Ile Pro
    210             215             220

Pro Gly Gln Met Arg Glu Pro Arg Gly Ser Asp Ile Ala Gly Thr Thr
225             230             235                 240

Ser Thr Pro Gln Glu Gln Gly Ala Trp Met Thr Gly Asn Pro Pro Ile
            245             250             255

Pro Val Gly Asp Ile Tyr Lys Arg Trp Ile Ile Leu Gly Leu Asn Lys
            260             265             270

Ile Val Arg Met Tyr Ser Pro Val Ser Ile Leu Asp Ile Lys Gln Gly
            275             280             285

Pro Lys Glu Pro Phe Arg Asp Tyr Val Asp Arg Phe Phe Lys Thr Leu
            290             295             300

Arg Ala Glu Gln Ala Thr Gln Glu Val Lys Gly Trp Met Thr Glu Thr
305             310             315                 320

Leu Leu Val Gln Asn Ala Asn Pro Asp Cys Lys Ser Ile Leu Arg Ala
            325             330             335

Leu Gly Xaa Gly Ala Thr Leu Glu Glu Met Met Thr Ala Cys Gln Gly
            340             345             350

Val Gly Gly Pro Gly His Lys Ala Arg Val Leu Ala Glu Ala Met Ser
            355             360             365

Gln Val Gln Gln Thr Asn Ile Met Met Gln Arg Gly Asn Phe Arg Gly
            370             375             380

Gln Lys Arg Ile Lys Cys Phe Asn Cys Gly Lys Glu Gly His Leu Ala
385             390             395                 400

Arg Asn Cys Arg Ala Pro Arg Lys Lys Gly Cys Trp Lys Cys Gly Lys
            405             410             415

Glu Gly His Gln Met Lys Asp Cys Thr Glu Arg Gln Ala Asn Phe Leu
            420             425             430

Gly Lys Ile Trp Pro Ser Ser Lys Gly Arg Pro Gly Asn Phe Pro Gln
            435             440             445

Ser Arg Pro Glu Pro Thr Ala Pro Pro Ala Glu Ile Phe Gly Met Gly
            450             455             460

Glu Glu Ile Ala Ser Pro Pro Lys Gln Glu Gln Lys Asp Arg Glu Gln
465             470             475                 480

Xaa Xaa Pro Pro Leu Val Ser Leu Lys Ser Leu Phe Gly Asn Asp Pro
                485             490             495

Leu Ser Gln
```

```
<210> SEQ ID NO 3
<211> LENGTH: 947
<212> TYPE: PRT
<213> ORGANISM: Human immunodeficiency virus type 1
<220> FEATURE:
<221> NAME/KEY: MOD_RES
<222> LOCATION: (344)
<223> OTHER INFORMATION: Variable amino acid
<220> FEATURE:
<221> NAME/KEY: MOD_RES
<222> LOCATION: (534)
<223> OTHER INFORMATION: Variable amino acid
<220> FEATURE:
<221> NAME/KEY: MOD_RES
<222> LOCATION: (582)
<223> OTHER INFORMATION: Variable amino acid
<220> FEATURE:
<221> NAME/KEY: MOD_RES
<222> LOCATION: (680)
<223> OTHER INFORMATION: Variable amino acid

<400> SEQUENCE: 3

Pro Gln Ile Thr Leu Trp Gln Arg Pro Leu Val Thr Val Lys Ile Gly
  1               5                  10                  15

Gly Gln Leu Lys Glu Ala Leu Leu Asp Thr Gly Ala Asp Asp Thr Val
             20                  25                  30

Leu Glu Asp Ile Asn Leu Pro Gly Lys Trp Lys Pro Lys Met Ile Gly
         35                  40                  45

Gly Ile Gly Gly Phe Ile Lys Val Lys Gln Tyr Asp Gln Ile Leu Ile
     50                  55                  60

Glu Ile Cys Gly Lys Lys Ala Ile Gly Thr Val Leu Val Gly Pro Thr
 65                  70                  75                  80

Pro Val Asn Ile Ile Gly Arg Asn Met Leu Thr Gln Ile Gly Cys Thr
                 85                  90                  95

Leu Asn Phe Pro Ile Ser Pro Ile Glu Thr Val Pro Val Lys Leu Lys
            100                 105                 110

Pro Gly Met Asp Gly Pro Lys Val Lys Gln Trp Pro Leu Thr Glu Glu
        115                 120                 125

Lys Ile Lys Ala Leu Thr Glu Ile Cys Thr Glu Met Glu Lys Glu Gly
130                 135                 140

Lys Ile Ser Lys Ile Gly Pro Glu Asn Pro Tyr Asn Thr Pro Ile Phe
145                 150                 155                 160

Ala Ile Lys Lys Lys Asp Ser Thr Lys Trp Arg Lys Leu Val Asp Phe
                165                 170                 175

Arg Glu Leu Asn Lys Arg Thr Gln Asp Phe Trp Glu Val Gln Leu Gly
            180                 185                 190

Ile Pro His Pro Ala Gly Leu Lys Lys Lys Ser Val Thr Val Leu
        195                 200                 205

Asp Val Gly Asp Ala Tyr Phe Ser Val Pro Leu Asp Glu Ser Phe Arg
    210                 215                 220

Lys Tyr Thr Ala Phe Thr Ile Pro Ser Thr Asn Asn Glu Thr Pro Gly
225                 230                 235                 240

Ile Arg Tyr Gln Tyr Asn Val Leu Pro Gln Gly Trp Lys Gly Ser Pro
                245                 250                 255

Ala Ile Phe Gln Ser Ser Met Thr Lys Ile Leu Glu Pro Phe Arg Ser
            260                 265                 270

Lys Asn Pro Glu Ile Ile Ile Tyr Gln Tyr Met Asp Asp Leu Tyr Val
        275                 280                 285

Gly Ser Asp Leu Glu Ile Gly Gln His Arg Thr Lys Ile Glu Glu Leu
    290                 295                 300
```

-continued

```
Arg Ala His Leu Leu Ser Trp Gly Phe Thr Thr Pro Asp Lys Lys His
305                 310                 315                 320

Gln Lys Glu Pro Pro Phe Leu Trp Met Gly Tyr Glu Leu His Pro Asp
            325                 330                 335

Lys Trp Thr Val Gln Pro Ile Xaa Leu Pro Glu Lys Glu Ser Trp Thr
        340                 345                 350

Val Asn Asp Ile Gln Lys Leu Val Gly Lys Leu Asn Trp Ala Ser Gln
    355                 360                 365

Ile Tyr Ala Gly Ile Lys Val Lys Gln Leu Cys Lys Leu Leu Arg Gly
370                 375                 380

Ala Lys Ala Leu Thr Asp Ile Val Thr Leu Thr Glu Glu Ala Glu Leu
385                 390                 395                 400

Glu Leu Ala Glu Asn Arg Glu Ile Leu Lys Asp Pro Val His Gly Val
            405                 410                 415

Tyr Tyr Asp Pro Ser Lys Asp Leu Ile Ala Glu Ile Gln Lys Gln Gly
        420                 425                 430

Gln Asp Gln Trp Thr Tyr Gln Ile Tyr Gln Glu Pro Phe Lys Asn Leu
    435                 440                 445

Lys Thr Gly Lys Tyr Ala Arg Lys Arg Ser Ala His Thr Asn Asp Val
450                 455                 460

Lys Gln Leu Ala Glu Val Val Gln Lys Val Val Met Glu Ser Ile Val
465                 470                 475                 480

Ile Trp Gly Lys Thr Pro Lys Phe Lys Leu Pro Ile Gln Lys Glu Thr
            485                 490                 495

Trp Glu Thr Trp Trp Met Asp Tyr Trp Gln Ala Thr Trp Ile Pro Glu
        500                 505                 510

Trp Glu Phe Val Asn Thr Pro Pro Leu Val Lys Leu Trp Tyr Gln Leu
    515                 520                 525

Glu Lys Asp Pro Ile Xaa Gly Ala Glu Thr Phe Tyr Val Asp Gly Ala
530                 535                 540

Ala Asn Arg Glu Thr Lys Leu Gly Lys Ala Gly Tyr Val Thr Asp Arg
545                 550                 555                 560

Gly Arg Gln Lys Val Val Ser Leu Thr Glu Thr Thr Asn Gln Lys Thr
            565                 570                 575

Glu Leu His Ala Ile Xaa Leu Ala Leu Gln Asp Ser Gly Ser Glu Val
        580                 585                 590

Asn Ile Val Thr Asp Ser Gln Tyr Ala Leu Gly Ile Ile Gln Ala Gln
    595                 600                 605

Pro Asp Arg Ser Glu Ser Glu Leu Val Asn Gln Ile Ile Glu Lys Leu
610                 615                 620

Ile Gly Lys Asp Lys Val Tyr Leu Ser Trp Val Pro Ala His Lys Gly
625                 630                 635                 640

Ile Gly Gly Asn Glu Gln Val Asp Lys Leu Val Ser Ser Gly Ile Arg
            645                 650                 655

Lys Val Leu Phe Leu Asp Gly Ile Asp Lys Ala Gln Glu Glu His Glu
        660                 665                 670

Arg Tyr His Ser Asn Trp Arg Xaa Met Ala Ser Asp Phe Asn Leu Pro
    675                 680                 685

Pro Ile Val Ala Lys Glu Ile Val Ala Ser Cys Asp Lys Cys Gln Leu
690                 695                 700

Lys Gly Glu Ala Met His Gly Gln Val Asp Cys Ser Pro Gly Ile Trp
705                 710                 715                 720

Gln Leu Asp Cys Thr His Leu Glu Gly Lys Val Ile Leu Val Ala Val
```

-continued

```
                    725                 730                 735
His Val Ala Ser Gly Tyr Ile Glu Ala Glu Val Ile Pro Ala Glu Thr
                740                 745                 750
Gly Gln Glu Thr Ala Tyr Phe Leu Leu Lys Leu Ala Gly Arg Trp Pro
            755                 760                 765
Val Lys Val Val His Thr Asp Asn Gly Ser Asn Phe Thr Ser Ala Ala
        770                 775                 780
Phe Lys Ala Ala Cys Trp Trp Ala Asn Ile Gln Gln Glu Phe Gly Ile
785                 790                 795                 800
Pro Tyr Asn Pro Gln Ser Gln Gly Val Val Glu Ser Met Asn Lys Glu
                805                 810                 815
Leu Lys Lys Ile Ile Gly Gln Val Arg Glu Gln Ala Glu His Leu Lys
                820                 825                 830
Thr Ala Val Gln Met Ala Val Phe Ile His Asn Phe Lys Arg Lys Gly
                835                 840                 845
Gly Ile Gly Gly Tyr Ser Ala Gly Glu Arg Ile Ile Asp Ile Ile Ala
            850                 855                 860
Thr Asp Ile Gln Thr Lys Glu Leu Gln Lys Gln Ile Thr Lys Ile Gln
865                 870                 875                 880
Asn Phe Arg Val Tyr Tyr Arg Asp Ser Arg Asp Pro Ile Trp Lys Gly
                885                 890                 895
Pro Ala Lys Leu Leu Trp Lys Gly Glu Gly Ala Val Val Ile Gln Asp
                900                 905                 910
Asn Ser Asp Ile Lys Val Val Pro Arg Arg Lys Ala Lys Ile Ile Arg
                915                 920                 925
Asp Tyr Gly Lys Gln Met Ala Gly Asp Asp Cys Val Ala Gly Arg Gln
            930                 935                 940
Asp Glu Asp
945

<210> SEQ ID NO 4
<211> LENGTH: 875
<212> TYPE: PRT
<213> ORGANISM: Human immunodeficiency virus type 1
<220> FEATURE:
<221> NAME/KEY: MOD_RES
<222> LOCATION: (29)
<223> OTHER INFORMATION: Variable amino acid
<220> FEATURE:
<221> NAME/KEY: MOD_RES
<222> LOCATION: (61)
<223> OTHER INFORMATION: Variable amino acid
<220> FEATURE:
<221> NAME/KEY: MOD_RES
<222> LOCATION: (64)
<223> OTHER INFORMATION: Variable amino acid
<220> FEATURE:
<221> NAME/KEY: MOD_RES
<222> LOCATION: (84)
<223> OTHER INFORMATION: Variable amino acid
<220> FEATURE:
<221> NAME/KEY: MOD_RES
<222> LOCATION: (86)
<223> OTHER INFORMATION: Variable amino acid
<220> FEATURE:
<221> NAME/KEY: MOD_RES
<222> LOCATION: (129)
<223> OTHER INFORMATION: Variable amino acid
<220> FEATURE:
<221> NAME/KEY: MOD_RES
<222> LOCATION: (131)..(158)
<223> OTHER INFORMATION: Variable amino acid
<220> FEATURE:
<221> NAME/KEY: MOD_RES
<222> LOCATION: (190)..(198)
```

```
<223> OTHER INFORMATION: Variable amino acid
<220> FEATURE:
<221> NAME/KEY: MOD_RES
<222> LOCATION: (200)
<223> OTHER INFORMATION: Variable amino acid
<220> FEATURE:
<221> NAME/KEY: MOD_RES
<222> LOCATION: (239)
<223> OTHER INFORMATION: Variable amino acid
<220> FEATURE:
<221> NAME/KEY: MOD_RES
<222> LOCATION: (241)
<223> OTHER INFORMATION: Variable amino acid
<220> FEATURE:
<221> NAME/KEY: MOD_RES
<222> LOCATION: (278)..(279)
<223> OTHER INFORMATION: Variable amino acid
<220> FEATURE:
<221> NAME/KEY: MOD_RES
<222> LOCATION: (281)
<223> OTHER INFORMATION: Variable amino acid
<220> FEATURE:
<221> NAME/KEY: MOD_RES
<222> LOCATION: (293)
<223> OTHER INFORMATION: Variable amino acid
<220> FEATURE:
<221> NAME/KEY: MOD_RES
<222> LOCATION: (299)..(300)
<223> OTHER INFORMATION: Variable amino acid
<220> FEATURE:
<221> NAME/KEY: MOD_RES
<222> LOCATION: (303)
<223> OTHER INFORMATION: Variable amino acid
<220> FEATURE:
<221> NAME/KEY: MOD_RES
<222> LOCATION: (345)..(346)
<223> OTHER INFORMATION: Variable amino acid
<220> FEATURE:
<221> NAME/KEY: MOD_RES
<222> LOCATION: (349)
<223> OTHER INFORMATION: Variable amino acid
<220> FEATURE:
<221> NAME/KEY: MOD_RES
<222> LOCATION: (353)
<223> OTHER INFORMATION: Variable amino acid
<220> FEATURE:
<221> NAME/KEY: MOD_RES
<222> LOCATION: (356)
<223> OTHER INFORMATION: Variable amino acid
<220> FEATURE:
<221> NAME/KEY: MOD_RES
<222> LOCATION: (360)..(362)
<223> OTHER INFORMATION: Variable amino acid
<220> FEATURE:
<221> NAME/KEY: MOD_RES
<222> LOCATION: (364)
<223> OTHER INFORMATION: Variable amino acid
<220> FEATURE:
<221> NAME/KEY: MOD_RES
<222> LOCATION: (371)..(372)
<223> OTHER INFORMATION: Variable amino acid
<220> FEATURE:
<221> NAME/KEY: MOD_RES
<222> LOCATION: (405)..(415)
<223> OTHER INFORMATION: Variable amino acid
<220> FEATURE:
<221> NAME/KEY: MOD_RES
<222> LOCATION: (417)..(418)
<223> OTHER INFORMATION: Variable amino acid
<220> FEATURE:
<221> NAME/KEY: MOD_RES
<222> LOCATION: (426)
<223> OTHER INFORMATION: Variable amino acid
<220> FEATURE:
<221> NAME/KEY: MOD_RES
<222> LOCATION: (439)
<223> OTHER INFORMATION: Variable amino acid
<220> FEATURE:
<221> NAME/KEY: MOD_RES
<222> LOCATION: (469)..(476)
```

-continued

```
<223> OTHER INFORMATION: Variable amino acid
<220> FEATURE:
<221> NAME/KEY: MOD_RES
<222> LOCATION: (631)..(632)
<223> OTHER INFORMATION: Variable amino acid
<220> FEATURE:
<221> NAME/KEY: MOD_RES
<222> LOCATION: (656)
<223> OTHER INFORMATION: Variable amino acid
<220> FEATURE:
<221> NAME/KEY: MOD_RES
<222> LOCATION: (820)
<223> OTHER INFORMATION: Variable amino acid
<220> FEATURE:
<221> NAME/KEY: MOD_RES
<222> LOCATION: (834)
<223> OTHER INFORMATION: Variable amino acid

<400> SEQUENCE: 4
```

| | | | | | | | | | | | | | | |
|---|---|---|---|---|---|---|---|---|---|---|---|---|---|---|
| Met | Arg | Val | Met | Gly | Ile | Gln | Arg | Asn | Cys | Gln | His | Leu | Leu | Arg | Trp |
| 1 | | | | 5 | | | | | 10 | | | | | 15 | |
| Gly | Thr | Met | Ile | Leu | Gly | Met | Ile | Ile | Ile | Cys | Ser | Xaa | Ala | Glu | Asn |
| | | | 20 | | | | | 25 | | | | | 30 | | |
| Leu | Trp | Val | Thr | Val | Tyr | Tyr | Gly | Val | Pro | Val | Trp | Lys | Asp | Ala | Glu |
| | | | 35 | | | | | 40 | | | | | 45 | | |
| Thr | Thr | Leu | Phe | Cys | Ala | Ser | Asp | Ala | Lys | Ala | Tyr | Xaa | Thr | Glu | Xaa |
| | 50 | | | | | 55 | | | | | 60 | | | | |
| His | Asn | Val | Trp | Ala | Thr | His | Ala | Cys | Val | Pro | Thr | Asp | Pro | Asn | Pro |
| 65 | | | | | 70 | | | | | 75 | | | | | 80 |
| Gln | Glu | Ile | Xaa | Leu | Xaa | Asn | Val | Thr | Glu | Glu | Phe | Asn | Met | Trp | Lys |
| | | | | 85 | | | | | 90 | | | | | 95 | |
| Asn | Asp | Met | Val | Glu | Gln | Met | His | Thr | Asp | Ile | Ile | Ser | Leu | Trp | Asp |
| | | | 100 | | | | | 105 | | | | | 110 | | |
| Gln | Ser | Leu | Lys | Pro | Cys | Val | Lys | Leu | Thr | Pro | Leu | Cys | Val | Thr | Leu |
| | | | 115 | | | | | 120 | | | | | 125 | | |
| Xaa | Cys | Xaa | Xaa | Xaa | Xaa | Xaa | Xaa | Xaa | Xaa | Xaa | Xaa | Xaa | Xaa | Xaa | Xaa |
| | 130 | | | | | 135 | | | | | 140 | | | | |
| Xaa | Xaa | Xaa | Xaa | Xaa | Xaa | Xaa | Xaa | Xaa | Xaa | Xaa | Xaa | Xaa | Xaa | Ile | Lys |
| 145 | | | | | 150 | | | | | 155 | | | | | 160 |
| Asn | Cys | Ser | Phe | Asn | Met | Thr | Thr | Glu | Leu | Arg | Asp | Lys | Lys | Gln | Lys |
| | | | | 165 | | | | | 170 | | | | | 175 | |
| Val | Tyr | Ser | Leu | Phe | Tyr | Arg | Leu | Asp | Val | Val | Gln | Ile | Xaa | Xaa | Xaa |
| | | | 180 | | | | | 185 | | | | | 190 | | |
| Xaa | Xaa | Xaa | Xaa | Xaa | Xaa | Ser | Xaa | Tyr | Arg | Leu | Ile | Asn | Cys | Asn | Thr |
| | | | 195 | | | | | 200 | | | | | 205 | | |
| Ser | Ala | Ile | Thr | Gln | Ala | Cys | Pro | Lys | Val | Ser | Phe | Glu | Pro | Ile | Pro |
| | 210 | | | | | 215 | | | | | 220 | | | | |
| Ile | His | Tyr | Cys | Ala | Pro | Ala | Gly | Phe | Ala | Leu | Ile | Lys | Cys | Xaa | Asp |
| 225 | | | | | 230 | | | | | 235 | | | | | 240 |
| Xaa | Glu | Phe | Asn | Gly | Thr | Gly | Pro | Cys | Lys | Asn | Val | Ser | Thr | Val | Gln |
| | | | | 245 | | | | | 250 | | | | | 255 | |
| Cys | Thr | His | Gly | Ile | Lys | Pro | Val | Val | Ser | Thr | Gln | Leu | Leu | Leu | Asn |
| | | | 260 | | | | | 265 | | | | | 270 | | |
| Gly | Ser | Leu | Ala | Glu | Xaa | Xaa | Val | Xaa | Ile | Arg | Glu | Ser | Asn | Ile | Thr |
| | | | 275 | | | | | 280 | | | | | 285 | | |
| Asn | Asn | Ala | Lys | Xaa | Ile | Ile | Val | Gln | Leu | Xaa | Xaa | Pro | Val | Xaa | Ile |
| | 290 | | | | | 295 | | | | | 300 | | | | |
| Asn | Cys | Thr | Arg | Pro | Asn | Asn | Asn | Thr | Arg | Lys | Ser | Ile | Arg | Ile | Gly |
| 305 | | | | | 310 | | | | | 315 | | | | | 320 |

```
Pro Gly Gln Ala Lys Tyr Ala Thr Gly Asp Ile Ile Gly Asp Ile Arg
                325                 330                 335

Gln Ala His Cys Asn Val Ser Arg Xaa Xaa Trp Asn Xaa Thr Leu Gln
            340                 345                 350

Xaa Val Ala Xaa Gln Leu Arg Xaa Xaa Xaa Phe Xaa Asn Lys Thr Ile
        355                 360                 365

Ile Phe Xaa Xaa Ser Ser Gly Gly Asp Leu Glu Ile Thr Thr His Ser
    370                 375                 380

Phe Asn Cys Gly Gly Glu Phe Phe Tyr Cys Asn Thr Ser Gly Leu Phe
385                 390                 395                 400

Asn Ser Thr Trp Xaa Xaa Xaa Xaa Xaa Xaa Xaa Xaa Xaa Xaa Xaa Ser
                405                 410                 415

Xaa Xaa Ser Asn Asp Thr Ile Thr Leu Xaa Cys Arg Ile Lys Gln Ile
        420                 425                 430

Val Asn Met Trp Gln Arg Xaa Gly Gln Ala Met Tyr Ala Pro Pro Ile
            435                 440                 445

Gln Gly Val Ile Arg Cys Glu Ser Asn Ile Thr Gly Leu Ile Leu Thr
        450                 455                 460

Arg Asp Gly Gly Xaa Xaa Xaa Xaa Xaa Xaa Xaa Asn Glu Thr Phe
465                 470                 475                 480

Arg Pro Gly Gly Gly Asp Met Arg Asp Asn Trp Arg Ser Glu Leu Tyr
                485                 490                 495

Lys Tyr Lys Val Val Lys Ile Glu Pro Leu Gly Val Ala Pro Thr Arg
                500                 505                 510

Ala Lys Arg Arg Val Val Glu Arg Glu Lys Arg Ala Val Gly Ile Gly
        515                 520                 525

Ala Val Phe Leu Gly Phe Leu Gly Ala Ala Gly Ser Thr Met Gly Ala
    530                 535                 540

Ala Ser Ile Thr Leu Thr Val Gln Ala Arg Gln Leu Leu Ser Gly Ile
545                 550                 555                 560

Val Gln Gln Gln Ser Asn Leu Leu Arg Ala Ile Glu Ala Gln Gln His
                565                 570                 575

Leu Leu Lys Leu Thr Val Trp Gly Ile Lys Gln Leu Gln Ala Arg Val
            580                 585                 590

Leu Ala Val Glu Arg Tyr Leu Arg Asp Gln Gln Leu Leu Gly Ile Trp
        595                 600                 605

Gly Cys Ser Gly Lys Leu Ile Cys Thr Thr Asn Val Pro Trp Asn Ser
    610                 615                 620

Ser Trp Ser Asn Lys Ser Xaa Xaa Glu Ile Trp Asp Asn Met Thr Trp
625                 630                 635                 640

Leu Gln Trp Asp Lys Glu Ile Ser Asn Tyr Thr Gln Ile Ile Tyr Xaa
                645                 650                 655

Leu Ile Glu Glu Ser Gln Asn Gln Gln Glu Lys Asn Glu Gln Asp Leu
            660                 665                 670

Leu Ala Leu Asp Lys Trp Ala Asn Leu Trp Asn Trp Phe Asp Ile Ser
        675                 680                 685

Asn Trp Leu Tyr Trp Ile Lys Ile Phe Ile Met Ile Val Gly Gly Leu
    690                 695                 700

Ile Gly Leu Arg Ile Val Phe Ala Val Leu Ser Ile Ile Asn Arg Val
705                 710                 715                 720

Arg Gln Gly Tyr Ser Pro Leu Ser Phe Gln Thr His Thr Pro Asn Pro
                725                 730                 735

Arg Gly Leu Asp Arg Pro Gly Arg Ile Glu Glu Glu Gly Glu Gln
                740                 745                 750
```

```
Gly Arg Asp Arg Ser Ile Arg Leu Val Ser Gly Phe Leu Ala Leu Ala
            755                 760                 765

Trp Asp Asp Leu Arg Ser Leu Cys Leu Phe Ser Tyr His Arg Leu Arg
    770                 775                 780

Asp Phe Ile Leu Ile Ala Ala Arg Thr Val Glu Leu Leu Gly His Ser
785                 790                 795                 800

Ser Leu Lys Gly Leu Arg Leu Gly Trp Glu Gly Leu Lys Tyr Leu Trp
                805                 810                 815

Asn Leu Leu Xaa Tyr Trp Gly Arg Glu Leu Lys Ile Ser Ala Ile Asn
            820                 825                 830

Leu Xaa Asp Thr Ile Ala Ile Ala Val Ala Gly Trp Thr Asp Arg Val
    835                 840                 845

Ile Glu Ile Gly Gln Arg Ile Gly Arg Ala Ile Leu His Ile Pro Arg
            850                 855                 860

Arg Ile Arg Gln Gly Leu Glu Arg Ala Leu Leu
865                 870                 875

<210> SEQ ID NO 5
<211> LENGTH: 203
<212> TYPE: PRT
<213> ORGANISM: Human immunodeficiency virus type 1
<220> FEATURE:
<221> NAME/KEY: MOD_RES
<222> LOCATION: (25)
<223> OTHER INFORMATION: Variable amino acid
<220> FEATURE:
<221> NAME/KEY: MOD_RES
<222> LOCATION: (28)
<223> OTHER INFORMATION: Variable amino acid
<220> FEATURE:
<221> NAME/KEY: MOD_RES
<222> LOCATION: (83)
<223> OTHER INFORMATION: Variable amino acid
<220> FEATURE:
<221> NAME/KEY: MOD_RES
<222> LOCATION: (131)
<223> OTHER INFORMATION: Variable amino acid
<220> FEATURE:
<221> NAME/KEY: MOD_RES
<222> LOCATION: (180)
<223> OTHER INFORMATION: Variable amino acid
<220> FEATURE:
<221> NAME/KEY: MOD_RES
<222> LOCATION: (194)
<223> OTHER INFORMATION: Variable amino acid

<400> SEQUENCE: 5

Met Gly Gly Lys Trp Ser Lys Ser Ser Ile Val Gly Trp Pro Glu Val
1               5                   10                  15

Arg Glu Arg Met Arg Arg Thr Pro Xaa Ala Ala Xaa Gly Val Gly Ala
                20                  25                  30

Val Ser Gln Asp Leu Asp Lys His Gly Ala Ile Thr Ser Ser Asn Ile
            35                  40                  45

Asn His Pro Ser Cys Val Trp Leu Glu Ala Gln Glu Glu Glu Glu Val
        50                  55                  60

Gly Phe Pro Val Arg Pro Gln Val Pro Leu Arg Pro Met Thr Tyr Lys
65                  70                  75                  80

Gly Ala Xaa Asp Leu Ser His Phe Leu Lys Glu Lys Gly Gly Leu Asp
                85                  90                  95

Gly Leu Ile Tyr Ser Arg Lys Arg Gln Glu Ile Leu Asp Leu Trp Val
                100                 105                 110

Tyr His Thr Gln Gly Tyr Phe Pro Asp Trp Gln Asn Tyr Thr Pro Gly
            115                 120                 125
```

-continued

```
Pro Gly Xaa Arg Tyr Pro Leu Thr Phe Gly Trp Cys Phe Lys Leu Val
    130                 135                 140

Pro Val Asp Pro Asp Glu Val Glu Lys Ala Thr Glu Gly Glu Asn Asn
145                 150                 155                 160

Ser Leu Leu His Pro Ile Cys Gln His Gly Met Asp Asp Glu Glu Arg
                165                 170                 175

Glu Val Leu Xaa Trp Lys Phe Asp Ser Arg Leu Ala Leu Lys His Arg
            180                 185                 190

Ala Xaa Glu Leu His Pro Glu Phe Tyr Lys Asp
    195                 200

<210> SEQ ID NO 6
<211> LENGTH: 498
<212> TYPE: PRT
<213> ORGANISM: Human immunodeficiency virus type 1

<400> SEQUENCE: 6

Met Gly Ala Arg Ala Ser Ile Leu Ser Gly Gly Lys Leu Asp Ala Trp
  1               5                  10                  15

Glu Lys Ile Arg Leu Arg Pro Gly Gly Lys Lys Lys Tyr Arg Leu Lys
             20                  25                  30

His Leu Val Trp Ala Ser Arg Glu Leu Asp Arg Phe Ala Leu Asn Pro
         35                  40                  45

Ser Leu Leu Glu Thr Thr Glu Gly Cys Gln Gln Ile Met Asn Gln Leu
     50                  55                  60

Gln Pro Ala Val Lys Thr Gly Thr Glu Gly Ile Lys Ser Leu Phe Asn
 65                  70                  75                  80

Thr Val Ala Thr Leu Tyr Cys Val His Gln Arg Ile Asp Val Lys Asp
                 85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Asp Ser Ser Lys Val
        115                 120                 125

Ser Gln Asn Tyr Pro Ile Ile Gln Asn Ala Gln Gly Gln Met Ile His
    130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
    210                 215                 220

Pro Gly Gln Ile Arg Glu Pro Arg Gly Ser Asp Ile Ala Gly Thr Thr
225                 230                 235                 240

Ser Thr Pro Gln Glu Gln Leu Gln Trp Met Thr Gly Asn Pro Pro Ile
                245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
        275                 280                 285

Pro Lys Glu Pro Phe Arg Asp Tyr Val Asp Arg Phe Phe Lys Ala Leu
    290                 295                 300
```

```
Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Ala Gln Gln Thr Asn Ile Met Met Gln Arg Gly Asn Phe Arg Gly
    370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Pro Ala Glu Leu Phe Gly Met Gly
    450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln

<210> SEQ ID NO 7
<211> LENGTH: 947
<212> TYPE: PRT
<213> ORGANISM: Human immunodeficiency virus type 1

<400> SEQUENCE: 7

Pro Gln Ile Leu Thr Trp Gln Arg Pro Leu Val Thr Val Lys Ile Gly
  1               5                  10                  15

Gly Gln Leu Lys Glu Ala Leu Leu Asp Thr Gly Ala Asp Asp Thr Val
                 20                  25                  30

Leu Glu Asp Ile Asn Leu Pro Gly Lys Trp Lys Pro Arg Met Ile Gly
             35                  40                  45

Gly Ile Gly Gly Phe Ile Lys Val Lys Gln Tyr Asp Gln Ile Leu Ile
         50                  55                  60

Glu Ile Cys Gly Lys Lys Ala Ile Gly Thr Val Leu Val Gly Pro Thr
 65                  70                  75                  80

Pro Val Asn Ile Ile Gly Arg Asn Met Leu Thr Gln Ile Gly Cys Thr
                 85                  90                  95

Leu Asn Phe Pro Ile Ser Pro Ile Glu Thr Val Pro Val Thr Leu Lys
            100                 105                 110

Pro Gly Met Asp Gly Pro Lys Val Lys Gln Trp Pro Leu Thr Glu Glu
        115                 120                 125

Lys Ile Lys Ala Leu Thr Glu Ile Cys Thr Glu Met Glu Lys Glu Gly
    130                 135                 140

Lys Ile Ser Lys Ile Gly Pro Glu Asn Pro Tyr Asn Thr Pro Ile Phe
145                 150                 155                 160

Ala Ile Lys Lys Lys Asp Ser Thr Lys Trp Arg Lys Leu Val Asp Phe
                165                 170                 175
```

```
Arg Glu Leu Asn Lys Arg Thr Gln Asp Phe Trp Glu Val Gln Leu Gly
            180                 185                 190
Ile Pro His Pro Ala Gly Leu Lys Lys Ser Val Thr Val Leu
        195                 200                 205
Asp Val Gly Asp Ala Tyr Phe Ser Val Pro Leu Asp Glu Asn Phe Arg
    210                 215                 220
Lys Tyr Thr Ala Phe Thr Ile Pro Ser Thr Asn Asn Glu Thr Pro Gly
225                 230                 235                 240
Val Arg Tyr Gln Tyr Asn Val Leu Pro Gln Gly Trp Lys Gly Ser Pro
                245                 250                 255
Ala Ile Phe Gln Ser Ser Met Thr Lys Ile Leu Glu Pro Phe Arg Ser
            260                 265                 270
Lys Asn Pro Glu Ile Ile Ile Tyr Gln Tyr Met Asp Asp Leu Tyr Val
        275                 280                 285
Gly Ser Asp Leu Glu Ile Gly Gln His Arg Thr Lys Ile Glu Glu Leu
    290                 295                 300
Arg Ala His Leu Leu Ser Trp Gly Phe Thr Thr Pro Asp Lys Lys His
305                 310                 315                 320
Gln Lys Glu Pro Pro Phe Leu Trp Met Gly Tyr Glu Leu His Pro Asp
                325                 330                 335
Lys Trp Thr Val Gln Pro Ile Met Leu Pro Asp Lys Glu Ser Trp Thr
            340                 345                 350
Val Asn Asp Ile Gln Lys Leu Val Gly Lys Leu Asn Trp Ala Ser Gln
        355                 360                 365
Ile Tyr Ala Gly Ile Lys Val Lys Gln Leu Cys Arg Leu Leu Arg Gly
    370                 375                 380
Ala Lys Ala Leu Thr Asp Ile Val Thr Leu Thr Glu Glu Ala Glu Leu
385                 390                 395                 400
Glu Leu Ala Glu Asn Arg Glu Ile Leu Lys Asp Pro Val His Gly Val
                405                 410                 415
Tyr Tyr Asp Pro Ser Lys Asp Leu Val Ala Glu Ile Gln Lys Gln Gly
            420                 425                 430
Gln Asp Gln Trp Thr Tyr Gln Ile Tyr Gln Glu Pro Phe Lys Asn Leu
        435                 440                 445
Lys Thr Gly Lys Tyr Ala Arg Lys Arg Ser Ala His Thr Asn Asp Val
    450                 455                 460
Arg Gln Leu Ala Glu Val Val Gln Lys Val Ala Met Glu Ser Ile Val
465                 470                 475                 480
Ile Trp Gly Lys Thr Pro Lys Phe Lys Leu Pro Ile Gln Lys Glu Thr
                485                 490                 495
Trp Glu Thr Trp Trp Met Asp Tyr Trp Gln Ala Thr Trp Ile Pro Glu
            500                 505                 510
Trp Glu Phe Val Asn Thr Pro Pro Leu Val Lys Leu Trp Tyr Gln Leu
        515                 520                 525
Glu Lys Asp Pro Ile Leu Gly Ala Glu Thr Phe Tyr Val Asp Gly Ala
    530                 535                 540
Ala Asn Arg Glu Thr Lys Leu Gly Lys Ala Gly Tyr Val Thr Asp Arg
545                 550                 555                 560
Gly Arg Gln Lys Val Val Ser Leu Thr Glu Thr Thr Asn Gln Lys Thr
                565                 570                 575
Glu Leu His Ala Ile Leu Leu Ala Leu Gln Asp Ser Gly Ser Glu Val
            580                 585                 590
Asn Ile Val Thr Asp Ser Gln Tyr Ala Leu Gly Ile Ile Gln Ala Gln
        595                 600                 605
```

```
Pro Asp Arg Ser Glu Ser Glu Leu Val Asn Gln Ile Glu Lys Leu
    610                 615                 620

Ile Gly Lys Asp Lys Ile Tyr Leu Ser Trp Val Pro Ala His Lys Gly
625                 630                 635                 640

Ile Gly Gly Asn Glu Gln Val Asp Lys Leu Val Ser Ser Gly Ile Arg
                645                 650                 655

Lys Val Leu Phe Leu Asp Gly Ile Asp Lys Ala Gln Glu Asp His Glu
            660                 665                 670

Arg Tyr His Ser Asn Trp Arg Thr Met Ala Ser Asp Phe Asn Leu Pro
        675                 680                 685

Pro Ile Val Ala Lys Glu Ile Val Ala Ser Cys Asp Lys Cys Gln Leu
    690                 695                 700

Lys Gly Glu Ala Met His Gly Gln Val Asp Cys Ser Pro Gly Ile Trp
705                 710                 715                 720

Gln Leu Asp Cys Thr His Leu Glu Gly Lys Val Ile Leu Val Ala Val
                725                 730                 735

His Val Ala Ser Gly Tyr Ile Glu Ala Glu Val Ile Pro Ala Glu Thr
            740                 745                 750

Gly Gln Glu Thr Ala Tyr Phe Leu Leu Lys Leu Ala Gly Arg Trp Pro
        755                 760                 765

Val Lys Val Val His Thr Asp Asn Gly Ser Asn Phe Thr Ser Ala Ala
    770                 775                 780

Val Lys Ala Ala Cys Trp Trp Ala Asn Ile Gln Gln Glu Phe Gly Ile
785                 790                 795                 800

Pro Tyr Asn Pro Gln Ser Gln Gly Val Val Glu Ser Met Asn Lys Glu
                805                 810                 815

Leu Lys Lys Ile Ile Gly Gln Val Arg Asp Gln Ala Glu His Leu Lys
            820                 825                 830

Thr Ala Val Gln Met Ala Val Phe Ile His Asn Phe Lys Arg Lys Gly
        835                 840                 845

Gly Ile Gly Gly Tyr Ser Ala Gly Glu Arg Ile Ile Asp Ile Ile Ala
    850                 855                 860

Thr Asp Ile Gln Thr Lys Glu Leu Gln Lys Gln Ile Thr Lys Ile Gln
865                 870                 875                 880

Asn Phe Arg Val Tyr Tyr Arg Asp Ser Arg Asp Pro Ile Trp Lys Gly
                885                 890                 895

Pro Ala Lys Leu Leu Trp Lys Gly Glu Gly Ala Val Val Ile Gln Asp
            900                 905                 910

Asn Ser Asp Ile Lys Val Val Pro Arg Arg Lys Ala Lys Ile Leu Arg
        915                 920                 925

Asp Tyr Gly Lys Gln Met Ala Gly Asp Asp Cys Val Ala Gly Arg Gln
    930                 935                 940

Asp Glu Asp
945

<210> SEQ ID NO 8
<211> LENGTH: 204
<212> TYPE: PRT
<213> ORGANISM: Human immunodeficiency virus type 1

<400> SEQUENCE: 8

Met Gly Gly Lys Trp Ser Lys Gly Ser Ile Val Gly Trp Pro Glu Ile
 1               5                  10                  15

Arg Glu Arg Met Arg Arg Ala Pro Ala Ala Ala Pro Gly Val Gly Ala
            20                  25                  30
```

```
Val Ser Gln Asp Leu Asp Lys His Gly Ala Ile Thr Ser Ser Asn Ile
         35                  40                  45

Asn Asn Pro Ser Cys Val Trp Leu Glu Ala Gln Glu Glu Glu Val
 50                  55                  60

Gly Phe Pro Val Arg Pro Gln Val Pro Leu Arg Pro Met Thr Tyr Lys
 65                  70                  75                  80

Gly Ala Phe Asp Leu Ser His Phe Leu Lys Glu Lys Gly Gly Leu Asp
                 85                  90                  95

Gly Leu Ile Tyr Ser Arg Lys Arg Gln Glu Ile Leu Asp Leu Trp Val
            100                 105                 110

Tyr His Thr Gln Gly Tyr Phe Pro Asp Trp Gln Asn Tyr Thr Pro Gly
        115                 120                 125

Pro Gly Val Arg Tyr Pro Leu Thr Phe Gly Trp Cys Phe Lys Leu Val
    130                 135                 140

Pro Met Glu Pro Asp Glu Val Glu Lys Ala Thr Glu Gly Glu Asn Asn
145                 150                 155                 160

Ser Leu Leu His Pro Ile Cys Gln His Gly Met Asp Asp Glu Glu Arg
                165                 170                 175

Glu Val Leu Ile Trp Lys Phe Asp Ser Arg Leu Ala Leu Lys His Arg
            180                 185                 190

Ala Gln Glu Leu His Pro Glu Phe Tyr Lys Asp Cys
        195                 200

<210> SEQ ID NO 9
<211> LENGTH: 672
<212> TYPE: PRT
<213> ORGANISM: Human immunodeficiency virus type 1

<400> SEQUENCE: 9

Met Arg Val Met Glu Ile Gln Arg Asn Cys Gln His Leu Leu Arg Trp
  1               5                  10                  15

Gly Ile Met Ile Leu Gly Met Ile Ile Cys Ser Thr Ala Asp Asn
             20                  25                  30

Leu Trp Val Thr Val Tyr Tyr Gly Val Pro Val Trp Arg Asp Ala Glu
         35                  40                  45

Thr Thr Leu Phe Cys Ala Ser Asp Ala Lys Ala Tyr Ser Thr Glu Lys
 50                  55                  60

His Asn Val Trp Ala Thr His Ala Cys Val Pro Thr Asp Pro Asn Pro
 65                  70                  75                  80

Gln Glu Ile Pro Leu Asp Asn Val Thr Glu Glu Phe Asn Met Trp Lys
                 85                  90                  95

Asn Asn Met Val Asp Gln Met His Glu Asp Ile Ile Ser Leu Trp Asp
            100                 105                 110

Gln Ser Leu Lys Pro Cys Val Gln Leu Thr Pro Leu Cys Val Thr Leu
        115                 120                 125

Asn Cys Ser Asn Ala Arg Val Asn Ala Thr Phe Asn Ser Thr Glu Asp
    130                 135                 140

Arg Glu Gly Met Lys Asn Cys Ser Phe Asn Met Thr Thr Glu Leu Arg
145                 150                 155                 160

Asp Lys Lys Gln Gln Val Tyr Ser Leu Phe Tyr Arg Leu Asp Ile Glu
                165                 170                 175

Lys Ile Asn Ser Ser Asn Asn Ser Glu Tyr Arg Leu Val Asn Cys
            180                 185                 190

Asn Thr Ser Ala Ile Thr Gln Ala Cys Pro Lys Val Thr Phe Glu Pro
        195                 200                 205
```

```
Ile Pro Ile His Tyr Cys Ala Pro Ala Gly Phe Ala Ile Leu Lys Cys
    210                 215                 220
Asn Asp Thr Glu Phe Asn Gly Thr Gly Pro Cys Lys Asn Val Ser Thr
225                 230                 235                 240
Val Gln Cys Thr His Gly Ile Lys Pro Val Val Ser Thr Gln Leu Leu
                245                 250                 255
Leu Asn Gly Ser Leu Ala Glu Arg Glu Val Arg Ile Arg Ser Glu Asn
            260                 265                 270
Ile Ala Asn Asn Ala Lys Asn Ile Ile Val Gln Phe Ala Ser Pro Val
        275                 280                 285
Lys Ile Asn Cys Ile Arg Pro Asn Asn Asn Thr Arg Lys Ser Tyr Arg
    290                 295                 300
Ile Gly Pro Gly Gln Thr Phe Tyr Ala Thr Asp Ile Val Gly Asp Ile
305                 310                 315                 320
Arg Gln Ala His Cys Asn Val Ser Arg Thr Asp Trp Asn Asn Thr Leu
                325                 330                 335
Arg Leu Val Ala Asn Gln Leu Arg Lys Tyr Phe Ser Asn Lys Thr Ile
            340                 345                 350
Ile Phe Thr Asn Ser Ser Gly Gly Asp Leu Glu Ile Thr Thr His Ser
        355                 360                 365
Phe Asn Cys Gly Gly Glu Phe Phe Tyr Cys Asn Thr Ser Gly Leu Phe
    370                 375                 380
Asn Ser Thr Trp Thr Thr Asn Asn Met Gln Glu Ser Asn Asp Thr Ser
385                 390                 395                 400
Asn Gly Thr Ile Thr Leu Pro Cys Arg Ile Lys Gln Ile Ile Arg Met
                405                 410                 415
Trp Gln Arg Val Gly Gln Ala Met Tyr Ala Pro Pro Ile Glu Gly Val
            420                 425                 430
Ile Arg Cys Glu Ser Asn Ile Thr Gly Leu Ile Leu Thr Arg Asp Gly
        435                 440                 445
Gly Asn Asn Asn Ser Ala Asn Glu Thr Phe Arg Pro Gly Gly Gly Asp
    450                 455                 460
Ile Arg Asp Asn Trp Arg Ser Glu Leu Tyr Lys Tyr Lys Val Val Lys
465                 470                 475                 480
Ile Glu Pro Leu Gly Val Ala Pro Thr Arg Ala Lys Arg Arg Val Val
                485                 490                 495
Glu Arg Glu Lys Arg Ala Val Gly Ile Gly Ala Val Phe Leu Gly Phe
            500                 505                 510
Leu Gly Ala Ala Gly Ser Thr Met Gly Ala Ala Ser Ile Thr Leu Thr
        515                 520                 525
Val Gln Ala Arg Gln Leu Leu Ser Gly Ile Val Gln Gln Gln Ser Asn
    530                 535                 540
Leu Leu Arg Ala Ile Glu Ala Gln Gln Gln Leu Leu Lys Leu Thr Val
545                 550                 555                 560
Trp Gly Ile Lys Gln Leu Gln Ala Arg Val Leu Ala Val Glu Arg Tyr
                565                 570                 575
Leu Arg Asp Gln Gln Leu Leu Gly Ile Trp Gly Cys Ser Gly Lys Leu
            580                 585                 590
Ile Cys Thr Thr Asn Val Pro Trp Asn Ser Ser Trp Ser Asn Lys Ser
        595                 600                 605
Tyr Asp Asp Ile Trp Gln Asn Met Thr Trp Leu Gln Trp Asp Lys Glu
    610                 615                 620
Ile Ser Asn Tyr Thr Asp Ile Ile Tyr Ser Leu Ile Glu Glu Ser Gln
```

```
                625            630            635            640
            Asn Gln Gln Glu Lys Asn Glu Gln Asp Leu Leu Ala Leu Asp Lys Trp
                            645                 650                 655
            Ala Asn Leu Trp Asn Trp Phe Asp Ile Ser Lys Trp Leu Trp Tyr Ile
                            660                 665                 670

<210> SEQ ID NO 10
<211> LENGTH: 5775
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 10
agtcttctgt ttttacgtag gtgtcagcct aggtggtcaa tattggccat tagccatatt      60
attcattggt tatatagcat aaatcaatat tggctattgg ccattgcata cgttgtatcc     120
atatcataat atgtacattt atattggctc atgtccaaca ttaccgccat gttgacattg     180
attattgact agttattaat agtaatcaat tacggggtca ttagttcata gcccatatat     240
ggagttccgc gttacataac ttacggtaaa tggcccgcct ggctgaccgc ccaacgaccc     300
ccgcccattg acgtcaataa tgacgtatgt tcccatagta acgccaatag ggactttcca     360
ttgacgtcaa tgggtggagt atttacgta  aactgcccac ttggcagtac atcaagtgta     420
tcatatgcca agtacgcccc ctattgacgt caatgacggt aaatggcccg cctggcatta     480
tgcccagtac atgaccttat gggactttcc tacttggcag tacatctacg tattagtcat     540
cgctattacc atggtgatgc ggttttggca gtacatcaat gggcgtggat agcggtttga     600
ctcacgggga tttccaagtc tccaccccat tgacgtcaat gggagtttgt tttggcacca     660
aaatcaacgg gactttccaa aatgtcgtaa caactccgcc ccattgacgc aaatgggcgg     720
taggcgtgta cggtgggagg tctatataag cagagctcgt ttagtgaacc gtcagatcgc     780
ctggagacgc catccacgct gttttgacct ccatagaaga caccgggacc gatccagcct     840
ccgcggccgg gaacggtgca ttggaagctt gccgccacca tggccgccag agccagcatc     900
ctgagcgggg gcaagctgga cgcctgggag aagatcagac tgaggcctgg cggcaagaag     960
aagtaccggc tgaagcacct ggtgtgggcc agcagagagc tggatcgctt cgccctgaat    1020
cctagcctgc tggagaccac cgagggctgc cagcagatca tgaaccagct gcagcccgcc    1080
gtgaaaaccg gcaccgagga gatcaagagc ctgttcaaca ccgtggccac cctgtactgc    1140
gtgcaccagc ggatcgacgt gaaggatacc aaggaggccc tggacaagat cgaggagatc    1200
cagaacaaga gcaagcagaa aacccagcag gccgctgccg acaccggcga cagcagcaaa    1260
gtgagccaga actaccccat catccagaat gcccagggcc agatgatcca ccagaacctg    1320
agccccagaa ccctgaatgc ctgggtgaaa gtgatcgagg aaaaggcctt cagccccgaa    1380
gtgatcccta tgttcagcgc cctgagcgag ggcgccaccc ccagggacct gaacgtgatg    1440
ctgaacattg gggcggaca ccaggccgcc atgcagatgc tgaaggacac catcaatgag    1500
gaggccgccg agtgggacag actgcacccc gtgcaggccg acccatcccc cctggccag    1560 atcagagagc cagaggcag cgacatcgcc ggcaccacct ccacccctca agaacagctg    1620
cagtggatga ccgcaaccc tcccatccct gtgggcaaca tctacaagcg gtggatcatc    1680
ctgggcctga acaagattgt gcggatgtac agcccgtgt ccatcctgga tatcaagcag    1740 ggcccccaagg agcccttcag agactacgtg accggttct tcaaggccct gagagccgag    1800
caggccaccc aggacgtgaa gggctggatg accgagaccc tgctggtgca aacgccaac    1860
```

```
cccgactgca agagcatcct gaaggccctg ggcagcggcg ccacactgga ggagatgatg   1920
accgcctgcc agggagtggg cggacccggc cacaaggcca gagtgctggc cgaggccatg   1980
agccaggccc agcagaccaa catcatgatg cagcggggca acttcagagg ccagaagcgg   2040
atcaagtgct tcaactgcgg caaggagggc cacctggcca gaaactgcag agcccccagg   2100
aagaagggct gctggaagtg tggcaaggaa gggcaccaga tgaaggactg caccgagagg   2160
caggccaatt tcctgggcaa gatttggcct agcagcaagg gcagacccgg caatttcccc   2220
cagagcagac ccgagcccac cgccctccc gccgagctgt tcggcatggg cgagggcatc   2280
gccagcctgc ccaagcagga gcagaaggac agagagcagg tgccccccct ggtgtccctg   2340
aagtccctgt tcggcaacga tcctctgagc cagggatccc ccatcagccc catcgagacc   2400
gtgcccgtga ccctgaagcc cggcatggat ggccccaaag tgaaacagtg gcccctgacc   2460
gaggagaaga ttaaggccct gaccgaaatc tgtaccgaga tggagaagga gggcaagatc   2520
agcaagatcg gccccgagaa ccccctacaac acccccatct cgccatcaa gaagaaggac   2580 agcaccaagt ggcggaaact ggtggacttc cgggagctga acaagaggac ccaggacttc   2640
tgggaagtgc agctgggcat cccccaccct gccggcctga agaagaagaa gtccgtgaca   2700
gtgctggatg tgggcgacgc ctacttcagc gtgcccctgg acgagaactt caggaagtac   2760
accgccttca ccatccccag caccaacaac gagaccccg gagtgagata ccagtacaac   2820
gtgctgcctc agggctggaa gggcagcccc gccatcttcc agagcagcat gaccaagatc   2880 ctggagcccct tccggagcaa gaaccccgag atcatcatct accagtacat ggccgccctg   2940
tatgtgggca gcgatctgga gatcggccag cacaggacca agatcgaaga gctgagggcc   3000
cacctgctga gctggggctt caccaccccc gataagaagc accagaagga gccccctttc   3060
ctgtggatgg gctacgagct gcaccccgat aagtggaccg tgcagcccat catgctgccc   3120
gataaggaga gctggaccgt gaacgacatc cagaaactgg tggcaagct gaattgggcc   3180 agccaaatct acgccggcat taaagtgaag cagctgtgca ggctgctgag aggcgccaaa   3240
gccctgacag acatcgtgac actgacagag gaggccgagc tggagctggc cgagaacagg   3300
gagatcctga aggaccccgt gcacggcgtg tactacgacc ccagcaagga cctggtggcc   3360
gagattcaga agcagggcca ggaccagtgg acctaccaaa tctaccagga gcctttcaag   3420
aacctgaaaa ccgggaagta cgccaggaag agaagcgccc acaccaacga tgtgaggcag   3480
ctggccgaag tggtgcagaa agtggctatg gagagcatcg tgatctgggg caagaccccc   3540
aagttcaagc tgcccatcca gaaggagacc tgggaaacct ggtggatgga ctactggcag   3600
gccacctgga ttcctgagtg ggagttcgtg aacacccccc ctctggtgaa gctgtggtat   3660
cagctggaga aggaccccat cctgggcgcc gagaccttct acgtggacgg agccgccaat   3720
agagagacca gctgggcaa ggccggctac gtgaccgaca gaggcagaca gaaagtggtg   3780
tctctgaccg agacaaccaa ccagaaaacc gagctgcacg ccatcctgct ggccctgcag   3840
gacagcggca gcgaagtgaa catcgtgacc gactcccagt acgccctggg catcattcag   3900
gcccagcccg atagaagcga gagcgagctg gtgaaccaga tcatcgagaa gctgatcggc   3960
aaggacaaaa tctacctgag ctgggtgccc gcccacaagg gcatcggcgg caacgagcag   4020
gtggacaagc tggtgtccag cggcatccgg aaagtgctgt ttctgacgg catcgacaag   4080 gcccaggagg accacgagag ataccacagc aactggcgga caatggccag cgacttcaac   4140
ctgcctccca tcgtgccaa ggagatcgtg ccagctgcg ataagtgtca gctgaagggc   4200
gaggccatgc acggccaggt ggactgcagc cctggcatct ggcagctggc ctgcacccac   4260
```

```
ctggagggca aagtgattct ggtggccgtg cacgtggcca gcggctacat cgaggccgaa    4320
gtgattcccg ccgagaccgg ccaggagacc gcctacttcc tgctgaagct ggccggcaga    4380
tggcccgtga agtggtgca caccgccaac ggcagcaact tcacctctgc cgccgtgaag    4440
gccgcctgtt ggtgggccaa tatccagcag gagttcggca tccoctacaa ccctcagagc    4500 cagggcgtgg tggccagcat gaacaaggag ctgaagaaga tcatcggcca ggtgagggac    4560
caggccgagc acctgaaaac agccgtgcag atggccgtgt catccacaa cttcaagcgg    4620 aagggcggca ttggcggcta cagcgccgga gagcggatca tcgacatcat cgccaccgat    4680
atccagacca aggaactgca gaagcagatc accaagattc agaacttcag agtgtactac    4740
cgggacagca gggaccccat ctggaagggc cctgccaagc tgctgtggaa gggcgaaggc    4800
gccgtggtga tccaggacaa cagcgacatc aaagtggtgc cccggaggaa ggccaagatt    4860
ctgcgggact acggcaaaca gatggccggc gatgactgcg tggccggcag gcaggatgag    4920
gacagatcta tgggcggcaa gtggtccaag ggcagcattg tgggctggcc cgagatccgg    4980
gagagaatga gaagagcccc tgccgccgct cctggagtgg gcgccgtgtc tcaggatctg    5040
gataagcacg gcgccatcac cagcagcaac atcaacaacc ccagctgtgt gtggctggag    5100
gcccaggaag aggaggaagt gggcttccct gtgagacccc aggtgcccct gagacccatg    5160
acctacaagg gcgccttcga cctgagccac ttcctgaagg agaagggcgg cctggacggc    5220
ctgatctaca gccggaagcg gcaggagatc ctggatctgt gggtgtacca cacccagggc    5280
tacttccccg actggcagaa ttacaccct ggccctggag tgcggtatcc cctgaccttc    5340
ggctggtgct tcaagctggt gcctatggag cccgacgaag tggagaaggc cacagagggc    5400
gagaacaaca gcctgctgca ccctatctgc agcacggca tggacgatga ggagcgggaa    5460
gtgctgatct ggaagttcga cagcaggctg gccctgaagc acagagccca ggaactgcac    5520
ccagagttct acaaggactg ctgatgatca taataatcta gacgagatcc gaacttgttt    5580
attgcagctt ataatggtta caaataaagc aatagcatca caaatttcac aaataaagca    5640 ttttttcac tgcattctag ttgtggtttg tccaaactca tcaatgtatc ttatcatgtc    5700
tagatctgag gtatgatgat acgagatcga gggtgcgcgc atgcgaatgc ggaggcaagc    5760
atgccaggtt ccagc                                                     5775
```

<210> SEQ ID NO 11
<211> LENGTH: 4071
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 11

```
attattgaag catttatcag ggttattgtc tcatgagcgg atacatattt gaatgtattt      60
agaaaaataa acaaataggg gttccgcgca catttccccg aaaagtgcca cctgacgtct     120
aagaaaccat tattatcatg acattaacct ataaaaatag gcgtatcacg aggccctttc     180
gtcttcaaga attggtcgat ggcaaacagc tattatgggt attatgggtt cgaattaatt     240
aatcgacatc atcaataata taccttatag atggaatggt gccaatatgt aaatgaggtg     300
attttaaaaa gtgtgggccg tgtggtgatt ggctgtgggg ttaacggtta aaaggggcgg     360
cgcggccgtg ggaaaatgac gttttatggg ggtggagttt ttttgcaagt tgtcgcggga     420
aatgttacgc ataaaaaggc ttcttttctc acggaactac ttagttttcc cacggtattt     480
```

```
aacaggaaat gaggtagttt tgaccggatg caagtgaaaa ttgctgattt tcgcgcgaaa    540
actgaatgag gaagtgtttt tctgaataat gtggtattta tggcagggtg gagtatttgt    600
tcagggccag gtagactttg acccattacg tggaggtttc gattaccgtg tttttttacct   660 gaatttccgc gtaccgtgtc aaagtcttct gttttttacgt aggtgtcagc ctaggtggtc   720
aatattggcc attagccata ttattcattg gttatatagc ataaatcaat attggctatt    780
ggccattgca tacgttgtat ccatatcata atatgtacat ttatattggc tcatgtccaa    840
cattaccgcc atgttgacat tgattattga ctagttatta atagtaatca attacggggt    900
cattagttca tagcccatat atggagttcc gcgttacata acttacggta aatgcccgc     960 ctggctgacc gcccaacgac ccccgcccat tgacgtcaat aatgacgtat gttcccatag   1020
taacgccaat agggactttc cattgacgtc aatgggtgga gtatttacgg taaactgccc   1080
acttggcagt acatcaagtg tatcatatgc caagtacgcc ccctattgac gtcaatgacg   1140
gtaaatggcc cgcctggcat tatgcccagt acatgacctt atgggacttt cctacttggc   1200
agtacatcta cgtattagtc atcgctatta ccatggtgat gcggttttgg cagtacatca   1260
atgggcgtgg atagcggttt gactcacggg gatttccaag tctccacccc attgacgtca   1320
atgggagttt gttttggcac caaaatcaac gggactttcc aaaatgtcgt aacaactccg   1380
ccccattgac gcaaatgggc ggtaggcgtg tacggtggga ggtctatata agcagagctc   1440
gtttagtgaa ccgtcagatc gcctggagac gccatccacg ctgttttgac ctccatagaa   1500
gacaccggga ccgatccagc ctccgcggcc gggaacggtg cattggaagc ttgccgccac   1560
catgagggtg atggagatcc agcggaactg ccagcacctg ctgagatggg gcatcatgat   1620
cctgggcatg attatcatct gcagcaccgc cgacaacctg tgggtgaccg tgtactacgg   1680
cgtgcctgtg tggagagatg ccgagaccac cctgttctgc gccagcgacg ccaaggccta   1740
cagcaccgag aagcacaatg tgtgggccac ccacgcctgc gtgcctaccg atcccaaccc   1800
tcaggagatc cccctggaca acgtgaccga ggagttcaac atgtgaaga acaacatggt    1860 ggaccagatg cacgaggaca tcatcagcct gtgggaccag agcctgaagc cctgcgtgca   1920
gctgaccccc ctgtgcgtga ccctgaactg cagcaacgcc agagtgaacg ccaccttcaa   1980
ctccaccgag gacagggagg gcatgaagaa ctgcagcttc aacatgacca ccgagctgcg   2040
ggataagaag cagcaggtgt acagcctgtt ctaccggctg gacatcgaga agatcaacag   2100
cagcaacaac aacagcgagt accggctggt gaactgcaat accagcgcca tcacccaggc   2160
ctgccctaag gtgaccttcg agcccatccc catccactac tgcgcccctg ccggcttcgc   2220
catcctgaag tgcaacgaca ccgagttcaa tggcaccggc ccctgcaaga atgtgagcac   2280
cgtgcagtgc acccacggca tcaagcccgt ggtgtccacc cagctgctgc tgaacggcag   2340
cctggccgag agagaagtgc ggatcaggag cgagaacatc gccaacaacg ccaagaacat   2400
catcgtgcag ttcgccagcc ccgtgaagat caactgcatc cggcccaaca acaataccg    2460 gaagagctac agaatcggcc ctggccagac cttctacgcc accgacattg tgggcgacat   2520
cagacaggcc cactgcaacg tgtccaggac cgactggaac aacaccctga gactggtggc   2580
caaccagctg cggaagtact tcagcaacaa gaccatcatc ttcaccaaca gcagcggcgg   2640
agacctggag atcaccaccc acagcttcaa ttgtggcggc gagttcttct actgcaacac   2700
ctccggcctg ttcaatagca cctggaccac caacaacatg caggagtcca acgacaccag   2760
caacggcacc atcaccctgc cctgccggat caagcagatc atccggatgt ggcagcgcgt   2820
gggccaggcc atgtacgccc ctcccatcga gggcgtgatt cgctgcgaga gcaacatcac   2880
```

-continued

```
cggcctgatc ctgaccagag atggcggcaa caacaattcc gccaacgaga ccttcagacc    2940
tggcggcgga gatatccggg acaactggcg gagcgagctg tacaagtaca aggtggtgaa    3000
gatcgagccc ctgggcgtgg cccccaccag agccaagaga agagtggtgg agcgggagaa    3060
gagagccgtg ggcatcggcg ccgtgtttct gggcttcctg ggagccgccg gatctacaat    3120
gggagccgcc agcatcaccc tgaccgtgca ggccagacag ctgctgagcg catcgtgca    3180 gcagcagagc aatctgctga gagccatcga ggcccagcag cagctgctga agctgacagt    3240
gtggggcatc aagcagctgc aggccagggt gctggccgtg agagatacc tgagggacca    3300 gcagctcctg ggcatctggg gctgcagcgg caagctgatc tgcaccacca acgtgccctg    3360
gaatagcagc tggagcaaca gagctacga cgacatctgg cagaacatga cctggctgca    3420
gtgggacaag gagatcagca actacaccga catcatctac agcctgatcg aggagagcca    3480
gaaccagcag gagaagaacg agcaggatct gctggccctg acaagtggg ccaacctgtg    3540 gaactggttc gacatcagca gtggctgtg gtacatcaga tcttgataat ctagacgaga    3600
tccgaacttg tttattgcag cttataatgg ttacaaataa agcaatagca tcacaaattt    3660
cacaaataaa gcattttttt cactgcattc tagttgtggt ttgtccaaac tcatcaatgt    3720
atcttatcat gtctagatct gaggtatgat gatacgagat cgaggtgcg cgcatgcgaa    3780 tgcggaggca agcatgccag gttccagccg gtgtgtgtag atgtgaccga agatctcaga    3840
ccggatcatt tggttattgc ccgcactgga gcagagttcg gatccagtgg agaagaaact    3900
gactaaggtg agtattggga aaactttggg gtgggatttt cagatggaca gattgagtaa    3960
aaatttgttt tttctgtctt gcagctgaca tgactggaaa tgcttctttt aagggggga    4020 gtcttcagcc cttatctgac agggcgtctc ccatcctggg caggagttcg t    4071
```

```
<210> SEQ ID NO 12
<211> LENGTH: 5002
<212> TYPE: DNA
<213> ORGANISM: Artificial Sequence
<220> FEATURE:
<221> NAME/KEY: CDS
<222> LOCATION: (16)..(4980)
<220> FEATURE:
<223> OTHER INFORMATION: Description of Artificial Sequence: Synthetic
      construct

<400> SEQUENCE: 12
aagcttgccg ccacc atg gcc gcc aga gcc agc atc ctg agc ggg ggc aag       51
                Met Ala Ala Arg Ala Ser Ile Leu Ser Gly Gly Lys
                  1               5                  10 ctg gac gcc tgg gag aag atc aga ctg agg cct ggc ggc aag aag aag        99
Leu Asp Ala Trp Glu Lys Ile Arg Leu Arg Pro Gly Gly Lys Lys Lys
         15                  20                  25 tac cgg ctg aag cac ctg gtg tgg gcc agc aga gag ctg gat cgc ttc       147
Tyr Arg Leu Lys His Leu Val Trp Ala Ser Arg Glu Leu Asp Arg Phe
 30                  35                  40 gcc ctg aat cct agc ctg ctg gag acc acc gag ggc tgc cag cag atc       195
Ala Leu Asn Pro Ser Leu Leu Glu Thr Thr Glu Gly Cys Gln Gln Ile
 45                  50                  55                  60 atg aac cag ctg cag ccc gcc gtg aaa acc ggc acc gag gag atc aag       243
Met Asn Gln Leu Gln Pro Ala Val Lys Thr Gly Thr Glu Glu Ile Lys
                 65                  70                  75 agc ctg ttc aac acc gtg gcc acc ctg tac tgc gtg cac cag cgg atc       291
Ser Leu Phe Asn Thr Val Ala Thr Leu Tyr Cys Val His Gln Arg Ile
             80                  85                  90 gac gtg aag gat acc aag gag gcc ctg gac aag atc gag gag atc cag       339
Asp Val Lys Asp Thr Lys Glu Ala Leu Asp Lys Ile Glu Glu Ile Gln
```

-continued

```
                95                      100                     105
aac aag agc aag cag aaa acc cag cag gcc gct gcc gac acc ggc gac            387
Asn Lys Ser Lys Gln Lys Thr Gln Gln Ala Ala Ala Asp Thr Gly Asp
    110                     115                     120 agc agc aaa gtg agc cag aac tac ccc atc atc cag aat gcc cag ggc            435
Ser Ser Lys Val Ser Gln Asn Tyr Pro Ile Ile Gln Asn Ala Gln Gly
125                     130                     135                 140 cag atg atc cac cag aac ctg agc ccc aga acc ctg aat gcc tgg gtg            483
Gln Met Ile His Gln Asn Leu Ser Pro Arg Thr Leu Asn Ala Trp Val
                145                     150                     155 aaa gtg atc gag gaa aag gcc ttc agc ccc gaa gtg atc cct atg ttc            531
Lys Val Ile Glu Glu Lys Ala Phe Ser Pro Glu Val Ile Pro Met Phe
            160                     165                     170 agc gcc ctg agc gag ggc gcc acc ccc cag gac ctg aac gtg atg ctg            579
Ser Ala Leu Ser Glu Gly Ala Thr Pro Gln Asp Leu Asn Val Met Leu
        175                     180                     185 aac att gtg ggc gga cac cag gcc gcc atg cag atg ctg aag gac acc            627
Asn Ile Val Gly Gly His Gln Ala Ala Met Gln Met Leu Lys Asp Thr
    190                     195                     200 atc aat gag gag gcc gcc gag tgg gac aga ctg cac ccc gtg cag gcc            675
Ile Asn Glu Glu Ala Ala Glu Trp Asp Arg Leu His Pro Val Gln Ala
205                     210                     215                 220 gga ccc atc ccc cct ggc cag atc aga gag ccc aga ggc agc gac atc            723
Gly Pro Ile Pro Pro Gly Gln Ile Arg Glu Pro Arg Gly Ser Asp Ile
                225                     230                     235 gcc ggc acc acc tcc acc cct caa gaa cag ctg cag tgg atg acc ggc            771
Ala Gly Thr Thr Ser Thr Pro Gln Glu Gln Leu Gln Trp Met Thr Gly
            240                     245                     250 aac cct ccc atc cct gtg ggc aac atc tac aag cgg tgg atc atc ctg            819
Asn Pro Pro Ile Pro Val Gly Asn Ile Tyr Lys Arg Trp Ile Ile Leu
        255                     260                     265 ggc ctg aac aag att gtg cgg atg tac agc ccc gtg tcc atc ctg gat            867
Gly Leu Asn Lys Ile Val Arg Met Tyr Ser Pro Val Ser Ile Leu Asp
    270                     275                     280 atc aag cag ggc ccc aag gag ccc ttc aga gac tac gtg gac cgg ttc            915
Ile Lys Gln Gly Pro Lys Glu Pro Phe Arg Asp Tyr Val Asp Arg Phe
285                     290                     295                 300 ttc aag gcc ctg aga gcc gag cag gcc acc cag gac gtg aag ggc tgg            963
Phe Lys Ala Leu Arg Ala Glu Gln Ala Thr Gln Asp Val Lys Gly Trp
                305                     310                     315 atg acc gag acc ctg ctg gtg cag aac gcc aac ccc gac tgc aag agc            1011
Met Thr Glu Thr Leu Leu Val Gln Asn Ala Asn Pro Asp Cys Lys Ser
            320                     325                     330 atc ctg aag gcc ctg ggc agc ggc gcc aca ctg gag gag atg atg acc            1059
Ile Leu Lys Ala Leu Gly Ser Gly Ala Thr Leu Glu Glu Met Met Thr
        335                     340                     345 gcc tgc cag gga gtg ggc gga ccc ggc cac aag gcc aga gtg ctg gcc            1107
Ala Cys Gln Gly Val Gly Gly Pro Gly His Lys Ala Arg Val Leu Ala
    350                     355                     360 gag gcc atg agc cag gcc cag cag acc aac atc atg atg cag cgg ggc            1155
Glu Ala Met Ser Gln Ala Gln Gln Thr Asn Ile Met Met Gln Arg Gly
365                     370                     375                 380 aac ttc aga ggc cag aag cgg atc aag tgc ttc aac tgc ggc aag gag            1203
Asn Phe Arg Gly Gln Lys Arg Ile Lys Cys Phe Asn Cys Gly Lys Glu
                385                     390                     395 ggc cac ctg gcc aga aac tgc aga gcc ccc agg aag aag ggc tgc tgg            1251
Gly His Leu Ala Arg Asn Cys Arg Ala Pro Arg Lys Lys Gly Cys Trp
            400                     405                     410 aag tgt ggc aag gaa ggg cac cag atg aag gac tgc acc gag agg cag            1299
Lys Cys Gly Lys Glu Gly His Gln Met Lys Asp Cys Thr Glu Arg Gln
```

```
                  415                 420                 425
gcc aat ttc ctg ggc aag att tgg cct agc agc aag ggc aga ccc ggc    1347
Ala Asn Phe Leu Gly Lys Ile Trp Pro Ser Ser Lys Gly Arg Pro Gly
    430                 435                 440 aat ttc ccc cag agc aga ccc gag ccc acc gcc cct ccc gcc gag ctg    1395
Asn Phe Pro Gln Ser Arg Pro Glu Pro Thr Ala Pro Pro Ala Glu Leu
445                 450                 455                 460 ttc ggc atg ggc gag ggc atc gcc agc ctg ccc aag cag gag cag aag    1443
Phe Gly Met Gly Glu Gly Ile Ala Ser Leu Pro Lys Gln Glu Gln Lys
                465                 470                 475 gac aga gag cag gtg ccc ccc ctg gtg tcc ctg aag tcc ctg ttc ggc    1491
Asp Arg Glu Gln Val Pro Pro Leu Val Ser Leu Lys Ser Leu Phe Gly
                    480                 485                 490 aac gat cct ctg agc cag gga tcc atg gcc ccc cag atc acc ctg tgg    1539
Asn Asp Pro Leu Ser Gln Gly Ser Met Ala Pro Gln Ile Thr Leu Trp
                495                 500                 505 cag aga ccc ctg gtg acc gtg aag atc ggc ggc cag ctg aag gaa gcc    1587
Gln Arg Pro Leu Val Thr Val Lys Ile Gly Gly Gln Leu Lys Glu Ala
    510                 515                 520 ctg ctg gat aca ggc gcc gat gat acc gtg ctg gag gac atc aac ctg    1635
Leu Leu Asp Thr Gly Ala Asp Asp Thr Val Leu Glu Asp Ile Asn Leu
525                 530                 535                 540 ccc ggc aag tgg aag cct aga atg atc ggc ggc atc ggg ggc ttc atc    1683
Pro Gly Lys Trp Lys Pro Arg Met Ile Gly Gly Ile Gly Gly Phe Ile
                545                 550                 555 aaa gtg aag cag tac gac cag atc ctg atc gag att tgc ggg aag aag    1731
Lys Val Lys Gln Tyr Asp Gln Ile Leu Ile Glu Ile Cys Gly Lys Lys
                560                 565                 570 gcc atc ggc acc gtg ctg gtg ggc ccc acc cct gtg aat atc atc ggc    1779
Ala Ile Gly Thr Val Leu Val Gly Pro Thr Pro Val Asn Ile Ile Gly
    575                 580                 585 cgg aac atg ctg acc cag atc ggc tgc acc ctg aac ttc ccc atc agc    1827
Arg Asn Met Leu Thr Gln Ile Gly Cys Thr Leu Asn Phe Pro Ile Ser
590                 595                 600 ccc atc gag acc gtg ccc gtg acc ctg aag ccc ggc atg gat ggc ccc    1875
Pro Ile Glu Thr Val Pro Val Thr Leu Lys Pro Gly Met Asp Gly Pro
605                 610                 615                 620 aaa gtg aaa cag tgg ccc ctg acc gag gag aag att aag gcc ctg acc    1923
Lys Val Lys Gln Trp Pro Leu Thr Glu Glu Lys Ile Lys Ala Leu Thr
                625                 630                 635 gaa atc tgt acc gag atg gag aag gag ggc aag atc agc aag atc ggc    1971
Glu Ile Cys Thr Glu Met Glu Lys Glu Gly Lys Ile Ser Lys Ile Gly
                640                 645                 650 ccc gag aac ccc tac aac acc ccc atc ttc gcc atc aag aag aag gac    2019
Pro Glu Asn Pro Tyr Asn Thr Pro Ile Phe Ala Ile Lys Lys Lys Asp
                655                 660                 665 agc acc aag tgg cgg aaa ctg gtg gac ttc cgg gag ctg aac aag agg    2067
Ser Thr Lys Trp Arg Lys Leu Val Asp Phe Arg Glu Leu Asn Lys Arg
    670                 675                 680 acc cag gac ttc tgg gaa gtg cag ctg ggc atc ccc cac cct gcc ggc    2115
Thr Gln Asp Phe Trp Glu Val Gln Leu Gly Ile Pro His Pro Ala Gly
685                 690                 695                 700 ctg aag aag aag aag tcc gtg aca gtg ctg gat gtg ggc gac gcc tac    2163
Leu Lys Lys Lys Lys Ser Val Thr Val Leu Asp Val Gly Asp Ala Tyr
                705                 710                 715 ttc agc gtg ccc ctg gac gag aac ttc agg aag tac acc gcc ttc acc    2211
Phe Ser Val Pro Leu Asp Glu Asn Phe Arg Lys Tyr Thr Ala Phe Thr
                720                 725                 730 atc ccc agc acc aac aac gag acc ccc gga gtg aga tac cag tac aac    2259
Ile Pro Ser Thr Asn Asn Glu Thr Pro Gly Val Arg Tyr Gln Tyr Asn
```

-continued

```
                735                 740                 745
gtg ctg cct cag ggc tgg aag ggc agc ccc gcc atc ttc cag agc agc      2307
Val Leu Pro Gln Gly Trp Lys Gly Ser Pro Ala Ile Phe Gln Ser Ser
750                 755                 760 atg acc aag atc ctg gag ccc ttc cgg agc aag aac ccc gag atc atc      2355
Met Thr Lys Ile Leu Glu Pro Phe Arg Ser Lys Asn Pro Glu Ile Ile
765                 770                 775                 780 atc tac cag tac atg gcc gcc ctg tat gtg ggc agc gat ctg gag atc      2403
Ile Tyr Gln Tyr Met Ala Ala Leu Tyr Val Gly Ser Asp Leu Glu Ile
                785                 790                 795 ggc cag cac agg acc aag atc gaa gag ctg agg gcc cac ctg ctg agc      2451
Gly Gln His Arg Thr Lys Ile Glu Glu Leu Arg Ala His Leu Leu Ser
800                 805                 810 tgg ggc ttc acc acc ccc gat aag aag cac cag aag gag ccc cct ttc      2499
Trp Gly Phe Thr Thr Pro Asp Lys Lys His Gln Lys Glu Pro Pro Phe
        815                 820                 825 ctg tgg atg ggc tac gag ctg cac ccc gat aag tgg acc gtg cag ccc      2547
Leu Trp Met Gly Tyr Glu Leu His Pro Asp Lys Trp Thr Val Gln Pro
830                 835                 840 atc atg ctg ccc gat aag gag agc tgg acc gtg aac gac atc cag aaa      2595
Ile Met Leu Pro Asp Lys Glu Ser Trp Thr Val Asn Asp Ile Gln Lys
845                 850                 855                 860 ctg gtg ggc aag ctg aat tgg gcc agc caa atc tac gcc ggc att aaa      2643
Leu Val Gly Lys Leu Asn Trp Ala Ser Gln Ile Tyr Ala Gly Ile Lys
                865                 870                 875 gtg aag cag ctg tgc agg ctg ctg aga ggc gcc aaa gcc ctg aca gac      2691
Val Lys Gln Leu Cys Arg Leu Leu Arg Gly Ala Lys Ala Leu Thr Asp
                880                 885                 890 atc gtg aca ctg aca gag gag gcc gag ctg gag ctg gcc gag aac agg      2739
Ile Val Thr Leu Thr Glu Glu Ala Glu Leu Glu Leu Ala Glu Asn Arg
        895                 900                 905 gag atc ctg aag gac ccc gtg cac ggc gtg tac tac gac ccc agc aag      2787
Glu Ile Leu Lys Asp Pro Val His Gly Val Tyr Tyr Asp Pro Ser Lys
910                 915                 920 gac ctg gtg gcc gag att cag aag cag ggc cag gac cag tgg acc tac      2835
Asp Leu Val Ala Glu Ile Gln Lys Gln Gly Gln Asp Gln Trp Thr Tyr
925                 930                 935                 940 caa atc tac cag gag cct ttc aag aac ctg aaa acc ggg aag tac gcc      2883
Gln Ile Tyr Gln Glu Pro Phe Lys Asn Leu Lys Thr Gly Lys Tyr Ala
                945                 950                 955 agg aag aga agc gcc cac acc aac gat gtg agg cag ctg gcc gaa gtg      2931
Arg Lys Arg Ser Ala His Thr Asn Asp Val Arg Gln Leu Ala Glu Val
                960                 965                 970 gtg cag aaa gtg gct atg gag agc atc gtg atc tgg ggc aag acc ccc      2979
Val Gln Lys Val Ala Met Glu Ser Ile Val Ile Trp Gly Lys Thr Pro
975                 980                 985 aag ttc aag ctg ccc atc cag aag gag acc tgg gaa acc tgg tgg atg      3027
Lys Phe Lys Leu Pro Ile Gln Lys Glu Thr Trp Glu Thr Trp Trp Met
990                 995                 1000 gac tac tgg cag gcc acc tgg att cct gag tgg gag ttc gtg aac acc      3075
Asp Tyr Trp Gln Ala Thr Trp Ile Pro Glu Trp Glu Phe Val Asn Thr
1005                1010                1015                1020 ccc cct ctg gtg aag ctg tgg tat cag ctg gag aag gac ccc atc ctg      3123
Pro Pro Leu Val Lys Leu Trp Tyr Gln Leu Glu Lys Asp Pro Ile Leu
                1025                1030                1035 ggc gcc gag acc ttc tac gtg gac gga gcc gcc aat aga gag acc aag      3171
Gly Ala Glu Thr Phe Tyr Val Asp Gly Ala Ala Asn Arg Glu Thr Lys
        1040                1045                1050 ctg ggc aag gcc ggc tac gtg acc gac aga ggc aga cag aaa gtg gtg      3219
Leu Gly Lys Ala Gly Tyr Val Thr Asp Arg Gly Arg Gln Lys Val Val
```

|  |  |
|---|---|
| tct ctg acc gag aca acc aac cag aaa acc gag ctg cac gcc atc ctg<br>Ser Leu Thr Glu Thr Thr Asn Gln Lys Thr Glu Leu His Ala Ile Leu<br>1070              1075                   1080 | 3267 |
| ctg gcc ctg cag gac agc ggc agc gaa gtg aac atc gtg acc gac tcc<br>Leu Ala Leu Gln Asp Ser Gly Ser Glu Val Asn Ile Val Thr Asp Ser<br>1085           1090             1095                1100 | 3315 |
| cag tac gcc ctg ggc atc att cag gcc cag ccc gat aga agc gag agc<br>Gln Tyr Ala Leu Gly Ile Ile Gln Ala Gln Pro Asp Arg Ser Glu Ser<br>1105              1110                 1115 | 3363 |
| gag ctg gtg aac cag atc atc gag aag ctg atc ggc aag gac aaa atc<br>Glu Leu Val Asn Gln Ile Ile Glu Lys Leu Ile Gly Lys Asp Lys Ile<br>           1120               1125                1130 | 3411 |
| tac ctg agc tgg gtg ccc gcc cac aag ggc atc ggc ggc aac gag cag<br>Tyr Leu Ser Trp Val Pro Ala His Lys Gly Ile Gly Gly Asn Glu Gln<br>1135             1140               1145 | 3459 |
| gtg gac aag ctg gtg tcc agc ggc atc cgg aaa gtg ctg ttt ctg gac<br>Val Asp Lys Leu Val Ser Ser Gly Ile Arg Lys Val Leu Phe Leu Asp<br>           1150               1155               1160 | 3507 |
| ggc atc gac aag gcc cag gag gac cac gag aga tac cac agc aac tgg<br>Gly Ile Asp Lys Ala Gln Glu Asp His Glu Arg Tyr His Ser Asn Trp<br>1165            1170             1175                1180 | 3555 |
| cgg aca atg gcc agc gac ttc aac ctg cct ccc atc gtg gcc aag gag<br>Arg Thr Met Ala Ser Asp Phe Asn Leu Pro Pro Ile Val Ala Lys Glu<br>           1185               1190               1195 | 3603 |
| atc gtg gcc agc tgc gat aag tgt cag ctg aag ggc gag gcc atg cac<br>Ile Val Ala Ser Cys Asp Lys Cys Gln Leu Lys Gly Glu Ala Met His<br>1200             1205               1210 | 3651 |
| ggc cag gtg gac tgc agc cct ggc atc tgg cag ctg gcc tgc acc cac<br>Gly Gln Val Asp Cys Ser Pro Gly Ile Trp Gln Leu Ala Cys Thr His<br>           1215               1220               1225 | 3699 |
| ctg gag ggc aaa gtg att ctg gtg gcc gtg cac gtg gcc agc ggc tac<br>Leu Glu Gly Lys Val Ile Leu Val Ala Val His Val Ala Ser Gly Tyr<br>1230            1235               1240 | 3747 |
| atc gag gcc gaa gtg att ccc gcc gag acc ggc cag gag acc gcc tac<br>Ile Glu Ala Glu Val Ile Pro Ala Glu Thr Gly Gln Glu Thr Ala Tyr<br>1245            1250             1255                1260 | 3795 |
| ttc ctg ctg aag ctg gcc ggc aga tgg ccc gtg aaa gtg gtg cac acc<br>Phe Leu Leu Lys Leu Ala Gly Arg Trp Pro Val Lys Val Val His Thr<br>           1265               1270               1275 | 3843 |
| gcc aac ggc agc aac ttc acc tct gcc gcc gtg aag gcc gcc tgt tgg<br>Ala Asn Gly Ser Asn Phe Thr Ser Ala Ala Val Lys Ala Ala Cys Trp<br>1280            1285               1290 | 3891 |
| tgg gcc aat atc cag cag gag ttc ggc atc ccc tac aac cct cag agc<br>Trp Ala Asn Ile Gln Gln Glu Phe Gly Ile Pro Tyr Asn Pro Gln Ser<br>           1295               1300               1305 | 3939 |
| cag ggc gtg gtg gcc agc atg aac aag gag ctg aag aag atc atc ggc<br>Gln Gly Val Val Ala Ser Met Asn Lys Glu Leu Lys Lys Ile Ile Gly<br>1310            1315               1320 | 3987 |
| cag gtg agg gac cag gcc gag cac ctg aaa aca gcc gtg cag atg gcc<br>Gln Val Arg Asp Gln Ala Glu His Leu Lys Thr Ala Val Gln Met Ala<br>1325            1330               1335               1340 | 4035 |
| gtg ttc atc cac aac ttc aag cgg aag ggc ggc att ggc ggc tac agc<br>Val Phe Ile His Asn Phe Lys Arg Lys Gly Gly Ile Gly Gly Tyr Ser<br>           1345               1350               1355 | 4083 |
| gcc gga gag cgg atc atc gac atc atc gcc acc gat atc cag acc aag<br>Ala Gly Glu Arg Ile Ile Asp Ile Ile Ala Thr Asp Ile Gln Thr Lys<br>1360            1365               1370 | 4131 |
| gaa ctg cag aag cag atc acc aag att cag aac ttc aga gtg tac tac<br>Glu Leu Gln Lys Gln Ile Thr Lys Ile Gln Asn Phe Arg Val Tyr Tyr | 4179 |

```
cgg gac agc agg gac ccc atc tgg aag ggc cct gcc aag ctg ctg tgg      4227
Arg Asp Ser Arg Asp Pro Ile Trp Lys Gly Pro Ala Lys Leu Leu Trp
    1390                1395                1400 aag ggc gaa ggc gcc gtg gtg atc cag gac aac agc gac atc aaa gtg      4275
Lys Gly Glu Gly Ala Val Val Ile Gln Asp Asn Ser Asp Ile Lys Val
1405                1410                1415                1420 gtg ccc cgg agg aag gcc aag att ctg cgg gac tac ggc aaa cag atg      4323
Val Pro Arg Arg Lys Ala Lys Ile Leu Arg Asp Tyr Gly Lys Gln Met
                1425                1430                1435 gcc ggc gat gac tgc gtg gcc ggc agg cag gat gag gac aga tct atg      4371
Ala Gly Asp Asp Cys Val Ala Gly Arg Gln Asp Glu Asp Arg Ser Met
            1440                1445                1450 ggc ggc aag tgg tcc aag ggc agc att gtg ggc tgg ccc gag atc cgg      4419
Gly Gly Lys Trp Ser Lys Gly Ser Ile Val Gly Trp Pro Glu Ile Arg
        1455                1460                1465 gag aga atg aga aga gcc cct gcc gcc gct cct gga gtg ggc gcc gtg      4467
Glu Arg Met Arg Arg Ala Pro Ala Ala Ala Pro Gly Val Gly Ala Val
    1470                1475                1480 tct cag gat ctg gat aag cac ggc gcc atc acc agc agc aac atc aac      4515
Ser Gln Asp Leu Asp Lys His Gly Ala Ile Thr Ser Ser Asn Ile Asn
1485                1490                1495                1500 aac ccc agc tgt gtg tgg ctg gag gcc cag gaa gag gag gaa gtg ggc      4563
Asn Pro Ser Cys Val Trp Leu Glu Ala Gln Glu Glu Glu Glu Val Gly
                1505                1510                1515 ttc cct gtg aga ccc cag gtg ccc ctg aga ccc atg acc tac aag ggc      4611
Phe Pro Val Arg Pro Gln Val Pro Leu Arg Pro Met Thr Tyr Lys Gly
            1520                1525                1530 gcc ttc gac ctg agc cac ttc ctg aag gag aag ggc ggc ctg gac ggc      4659
Ala Phe Asp Leu Ser His Phe Leu Lys Glu Lys Gly Gly Leu Asp Gly
        1535                1540                1545 ctg atc tac agc cgg aag cgg cag gag atc ctg gat ctg tgg gtg tac      4707
Leu Ile Tyr Ser Arg Lys Arg Gln Glu Ile Leu Asp Leu Trp Val Tyr
    1550                1555                1560 cac acc cag ggc tac ttc ccc gac tgg cag aat tac acc cct ggc cct      4755
His Thr Gln Gly Tyr Phe Pro Asp Trp Gln Asn Tyr Thr Pro Gly Pro
1565                1570                1575                1580 gga gtg cgg tat ccc ctg acc ttc ggc tgg tgc ttc aag ctg gtg cct      4803
Gly Val Arg Tyr Pro Leu Thr Phe Gly Trp Cys Phe Lys Leu Val Pro
                1585                1590                1595 atg gag ccc gac gaa gtg gag aag gcc aca gag ggc gag aac aac agc      4851
Met Glu Pro Asp Glu Val Glu Lys Ala Thr Glu Gly Glu Asn Asn Ser
            1600                1605                1610 ctg ctg cac cct atc tgc cag cac ggc atg gac gat gag gag cgg gaa      4899
Leu Leu His Pro Ile Cys Gln His Gly Met Asp Asp Glu Glu Arg Glu
        1615                1620                1625 gtg ctg atc tgg aag ttc gac agc agg ctg gcc ctg aag cac aga gcc      4947
Val Leu Ile Trp Lys Phe Asp Ser Arg Leu Ala Leu Lys His Arg Ala
    1630                1635                1640 cag gaa ctg cac cca gag ttc tac aag gac tgc tgatgatcat aataatctag   5000
Gln Glu Leu His Pro Glu Phe Tyr Lys Asp Cys
1645                1650                1655 aa                                                                   5002

<210> SEQ ID NO 13
<211> LENGTH: 1655
<212> TYPE: PRT
<213> ORGANISM: Artificial Sequence
<220> FEATURE:
<223> OTHER INFORMATION: Description of Artificial Sequence: Synthetic
      construct
```

<400> SEQUENCE: 13

```
Met Ala Arg Ala Ser Ile Leu Ser Gly Gly Lys Leu Asp Ala Trp
  1               5                  10                 15

Glu Lys Ile Arg Leu Arg Pro Gly Gly Lys Lys Lys Tyr Arg Leu Lys
             20                 25                  30

His Leu Val Trp Ala Ser Arg Glu Leu Asp Arg Phe Ala Leu Asn Pro
             35                  40                  45

Ser Leu Leu Glu Thr Thr Glu Gly Cys Gln Gln Ile Met Asn Gln Leu
 50                  55                  60

Gln Pro Ala Val Lys Thr Gly Thr Glu Glu Ile Lys Ser Leu Phe Asn
 65                  70                  75                  80

Thr Val Ala Thr Leu Tyr Cys Val His Gln Arg Ile Asp Val Lys Asp
                 85                  90                  95

Thr Lys Glu Ala Leu Asp Lys Ile Glu Glu Ile Gln Asn Lys Ser Lys
                100                 105                 110

Gln Lys Thr Gln Gln Ala Ala Ala Asp Thr Gly Asp Ser Ser Lys Val
            115                 120                 125

Ser Gln Asn Tyr Pro Ile Ile Gln Asn Ala Gln Gly Gln Met Ile His
130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
210                 215                 220

Pro Gly Gln Ile Arg Glu Pro Arg Gly Ser Asp Ile Ala Gly Thr Thr
225                 230                 235                 240

Ser Thr Pro Gln Glu Gln Leu Gln Trp Met Thr Gly Asn Pro Pro Ile
                245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
        275                 280                 285

Pro Lys Glu Pro Phe Arg Asp Tyr Val Asp Arg Phe Phe Lys Ala Leu
290                 295                 300

Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Ala Gln Gln Thr Asn Ile Met Met Gln Arg Gly Asn Phe Arg Gly
370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415
```

-continued

```
Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
            435                 440                 445

Ser Arg Pro Glu Pro Thr Ala Pro Pro Ala Glu Leu Phe Gly Met Gly
450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
            485                 490                 495

Ser Gln Gly Ser Met Ala Pro Gln Ile Thr Leu Trp Gln Arg Pro Leu
            500                 505                 510

Val Thr Val Lys Ile Gly Gly Gln Leu Lys Glu Ala Leu Leu Asp Thr
            515                 520                 525

Gly Ala Asp Asp Thr Val Leu Glu Asp Ile Asn Leu Pro Gly Lys Trp
530                 535                 540

Lys Pro Arg Met Ile Gly Gly Ile Gly Gly Phe Ile Lys Val Lys Gln
545                 550                 555                 560

Tyr Asp Gln Ile Leu Ile Glu Ile Cys Gly Lys Lys Ala Ile Gly Thr
            565                 570                 575

Val Leu Val Gly Pro Thr Pro Val Asn Ile Ile Gly Arg Asn Met Leu
            580                 585                 590

Thr Gln Ile Gly Cys Thr Leu Asn Phe Pro Ile Ser Pro Ile Glu Thr
            595                 600                 605

Val Pro Val Thr Leu Lys Pro Gly Met Asp Gly Pro Lys Val Lys Gln
            610                 615                 620

Trp Pro Leu Thr Glu Glu Lys Ile Lys Ala Leu Thr Glu Ile Cys Thr
625                 630                 635                 640

Glu Met Glu Lys Glu Gly Lys Ile Ser Lys Ile Gly Pro Glu Asn Pro
            645                 650                 655

Tyr Asn Thr Pro Ile Phe Ala Ile Lys Lys Lys Asp Ser Thr Lys Trp
            660                 665                 670

Arg Lys Leu Val Asp Phe Arg Glu Leu Asn Lys Arg Thr Gln Asp Phe
            675                 680                 685

Trp Glu Val Gln Leu Gly Ile Pro His Pro Ala Gly Leu Lys Lys Lys
            690                 695                 700

Lys Ser Val Thr Val Leu Asp Val Gly Asp Ala Tyr Phe Ser Val Pro
705                 710                 715                 720

Leu Asp Glu Asn Phe Arg Lys Tyr Thr Ala Phe Thr Ile Pro Ser Thr
            725                 730                 735

Asn Asn Glu Thr Pro Gly Val Arg Tyr Gln Tyr Asn Val Leu Pro Gln
            740                 745                 750

Gly Trp Lys Gly Ser Pro Ala Ile Phe Gln Ser Ser Met Thr Lys Ile
            755                 760                 765

Leu Glu Pro Phe Arg Ser Lys Asn Pro Glu Ile Ile Ile Tyr Gln Tyr
            770                 775                 780

Met Ala Ala Leu Tyr Val Gly Ser Asp Leu Glu Ile Gly Gln His Arg
785                 790                 795                 800

Thr Lys Ile Glu Glu Leu Arg Ala His Leu Leu Ser Trp Gly Phe Thr
            805                 810                 815

Thr Pro Asp Lys Lys His Gln Lys Glu Pro Pro Phe Leu Trp Met Gly
            820                 825                 830

Tyr Glu Leu His Pro Asp Lys Trp Thr Val Gln Pro Ile Met Leu Pro
```

-continued

```
              835                 840                 845
Asp Lys Glu Ser Trp Thr Val Asn Asp Ile Gln Lys Leu Val Gly Lys
850                 855                 860

Leu Asn Trp Ala Ser Gln Ile Tyr Ala Gly Ile Lys Val Lys Gln Leu
865                 870                 875                 880

Cys Arg Leu Leu Arg Gly Ala Lys Ala Leu Thr Asp Ile Val Thr Leu
                885                 890                 895

Thr Glu Glu Ala Glu Leu Glu Leu Ala Glu Asn Arg Glu Ile Leu Lys
                900                 905                 910

Asp Pro Val His Gly Val Tyr Tyr Asp Pro Ser Lys Asp Leu Val Ala
                915                 920                 925

Glu Ile Gln Lys Gln Gly Gln Asp Gln Trp Thr Tyr Gln Ile Tyr Gln
930                 935                 940

Glu Pro Phe Lys Asn Leu Lys Thr Gly Lys Tyr Ala Arg Lys Arg Ser
945                 950                 955                 960

Ala His Thr Asn Asp Val Arg Gln Leu Ala Glu Val Val Gln Lys Val
                965                 970                 975

Ala Met Glu Ser Ile Val Ile Trp Gly Lys Thr Pro Lys Phe Lys Leu
                980                 985                 990

Pro Ile Gln Lys Glu Thr Trp Glu Thr Trp Trp Met Asp Tyr Trp Gln
                995                 1000                1005

Ala Thr Trp Ile Pro Glu Trp Glu Phe Val Asn Thr Pro Pro Leu Val
    1010                1015                1020

Lys Leu Trp Tyr Gln Leu Glu Lys Asp Pro Ile Leu Gly Ala Glu Thr
1025                1030                1035                1040

Phe Tyr Val Asp Gly Ala Ala Asn Arg Glu Thr Lys Leu Gly Lys Ala
                1045                1050                1055

Gly Tyr Val Thr Asp Arg Gly Arg Gln Lys Val Val Ser Leu Thr Glu
                1060                1065                1070

Thr Thr Asn Gln Lys Thr Glu Leu His Ala Ile Leu Leu Ala Leu Gln
                1075                1080                1085

Asp Ser Gly Ser Glu Val Asn Ile Val Thr Asp Ser Gln Tyr Ala Leu
                1090                1095                1100

Gly Ile Ile Gln Ala Gln Pro Asp Arg Ser Glu Ser Glu Leu Val Asn
1105                1110                1115                1120

Gln Ile Ile Glu Lys Leu Ile Gly Lys Asp Lys Ile Tyr Leu Ser Trp
                1125                1130                1135

Val Pro Ala His Lys Gly Ile Gly Gly Asn Glu Gln Val Asp Lys Leu
                1140                1145                1150

Val Ser Ser Gly Ile Arg Lys Val Leu Phe Leu Asp Gly Ile Asp Lys
                1155                1160                1165

Ala Gln Glu Asp His Glu Arg Tyr His Ser Asn Trp Arg Thr Met Ala
                1170                1175                1180

Ser Asp Phe Asn Leu Pro Pro Ile Val Ala Lys Glu Ile Val Ala Ser
1185                1190                1195                1200

Cys Asp Lys Cys Gln Leu Lys Gly Glu Ala Met His Gly Gln Val Asp
                1205                1210                1215

Cys Ser Pro Gly Ile Trp Gln Leu Ala Cys Thr His Leu Glu Gly Lys
                1220                1225                1230

Val Ile Leu Val Ala Val His Val Ala Ser Gly Tyr Ile Glu Ala Glu
                1235                1240                1245

Val Ile Pro Ala Glu Thr Gly Gln Glu Thr Ala Tyr Phe Leu Leu Lys
                1250                1255                1260
```

Leu Ala Gly Arg Trp Pro Val Lys Val Val His Thr Ala Asn Gly Ser
1265                1270                1275                1280

Asn Phe Thr Ser Ala Ala Val Lys Ala Ala Cys Trp Trp Ala Asn Ile
            1285                1290                1295

Gln Gln Glu Phe Gly Ile Pro Tyr Asn Pro Gln Ser Gln Gly Val Val
        1300                1305                1310

Ala Ser Met Asn Lys Glu Leu Lys Lys Ile Ile Gly Gln Val Arg Asp
    1315                1320                1325

Gln Ala Glu His Leu Lys Thr Ala Val Gln Met Ala Val Phe Ile His
1330                1335                1340

Asn Phe Lys Arg Lys Gly Gly Ile Gly Gly Tyr Ser Ala Gly Glu Arg
            1345                1350                1355                1360

Ile Ile Asp Ile Ile Ala Thr Asp Ile Gln Thr Lys Glu Leu Gln Lys
        1365                1370                1375

Gln Ile Thr Lys Ile Gln Asn Phe Arg Val Tyr Tyr Arg Asp Ser Arg
    1380                1385                1390

Asp Pro Ile Trp Lys Gly Pro Ala Lys Leu Leu Trp Lys Gly Glu Gly
1395                1400                1405

Ala Val Val Ile Gln Asp Asn Ser Asp Ile Lys Val Val Pro Arg Arg
            1410                1415                1420

Lys Ala Lys Ile Leu Arg Asp Tyr Gly Lys Gln Met Ala Gly Asp Asp
1425                1430                1435                1440

Cys Val Ala Gly Arg Gln Asp Glu Asp Arg Ser Met Gly Gly Lys Trp
            1445                1450                1455

Ser Lys Gly Ser Ile Val Gly Trp Pro Glu Ile Arg Glu Arg Met Arg
        1460                1465                1470

Arg Ala Pro Ala Ala Ala Pro Gly Val Gly Ala Val Ser Gln Asp Leu
    1475                1480                1485

Asp Lys His Gly Ala Ile Thr Ser Ser Asn Ile Asn Asn Pro Ser Cys
1490                1495                1500

Val Trp Leu Glu Ala Gln Glu Glu Glu Val Gly Phe Pro Val Arg
1505                1510                1515                1520

Pro Gln Val Pro Leu Arg Pro Met Thr Tyr Lys Gly Ala Phe Asp Leu
            1525                1530                1535

Ser His Phe Leu Lys Glu Lys Gly Gly Leu Asp Gly Leu Ile Tyr Ser
        1540                1545                1550

Arg Lys Arg Gln Glu Ile Leu Asp Leu Trp Val Tyr His Thr Gln Gly
    1555                1560                1565

Tyr Phe Pro Asp Trp Gln Asn Tyr Thr Pro Gly Pro Gly Val Arg Tyr
1570                1575                1580

Pro Leu Thr Phe Gly Trp Cys Phe Lys Leu Val Pro Met Glu Pro Asp
1585                1590                1595                1600

Glu Val Glu Lys Ala Thr Glu Gly Glu Asn Asn Ser Leu Leu His Pro
            1605                1610                1615

Ile Cys Gln His Gly Met Asp Asp Glu Glu Arg Glu Val Leu Ile Trp
        1620                1625                1630

Lys Phe Asp Ser Arg Leu Ala Leu Lys His Arg Ala Gln Glu Leu His
    1635                1640                1645

Pro Glu Phe Tyr Lys Asp Cys
1650                1655

<210> SEQ ID NO 14
<211> LENGTH: 2050
<212> TYPE: DNA
<213> ORGANISM: Artificial Sequence

```
<220> FEATURE:
<221> NAME/KEY: CDS
<222> LOCATION: (16)..(2037)
<220> FEATURE:
<223> OTHER INFORMATION: Description of Artificial Sequence: Synthetic
      construct

<400> SEQUENCE: 14
aagcttgccg ccacc atg agg gtg atg gag atc cag cgg aac tgc cag cac        51
                 Met Arg Val Met Glu Ile Gln Arg Asn Cys Gln His
                 1               5                   10 ctg ctg aga tgg ggc atc atg atc ctg ggc atg att atc atc tgc agc        99
Leu Leu Arg Trp Gly Ile Met Ile Leu Gly Met Ile Ile Ile Cys Ser
        15                  20                  25 acc gcc gac aac ctg tgg gtg acc gtg tac tac ggc gtg cct gtg tgg       147
Thr Ala Asp Asn Leu Trp Val Thr Val Tyr Tyr Gly Val Pro Val Trp
30                  35                  40 aga gat gcc gag acc acc ctg ttc tgc gcc agc gac gcc aag gcc tac       195
Arg Asp Ala Glu Thr Thr Leu Phe Cys Ala Ser Asp Ala Lys Ala Tyr
45                  50                  55                  60 agc acc gag aag cac aat gtg tgg gcc acc cac gcc tgc gtg cct acc       243
Ser Thr Glu Lys His Asn Val Trp Ala Thr His Ala Cys Val Pro Thr
            65                  70                  75 gat ccc aac cct cag gag atc ccc ctg gac aac gtg acc gag gag ttc       291
Asp Pro Asn Pro Gln Glu Ile Pro Leu Asp Asn Val Thr Glu Glu Phe
        80                  85                  90 aac atg tgg aag aac aac atg gtg gac cag atg cac gag gac atc atc       339
Asn Met Trp Lys Asn Asn Met Val Asp Gln Met His Glu Asp Ile Ile
    95                  100                 105 agc ctg tgg gac cag agc ctg aag ccc tgc gtg cag ctg acc ccc ctg       387
Ser Leu Trp Asp Gln Ser Leu Lys Pro Cys Val Gln Leu Thr Pro Leu
110                 115                 120 tgc gtg acc ctg aac tgc agc aac gcc aga gtg aac gcc acc ttc aac       435
Cys Val Thr Leu Asn Cys Ser Asn Ala Arg Val Asn Ala Thr Phe Asn
125                 130                 135                 140 tcc acc gag gac agg gag ggc atg aag aac tgc agc ttc aac atg acc       483
Ser Thr Glu Asp Arg Glu Gly Met Lys Asn Cys Ser Phe Asn Met Thr
            145                 150                 155 acc gag ctg cgg gat aag aag cag cag gtg tac agc ctg ttc tac cgg       531
Thr Glu Leu Arg Asp Lys Lys Gln Gln Val Tyr Ser Leu Phe Tyr Arg
        160                 165                 170 ctg gac atc gag aag atc aac agc agc aac aac agc gag tac cgg          579
Leu Asp Ile Glu Lys Ile Asn Ser Ser Asn Asn Ser Glu Tyr Arg
    175                 180                 185 ctg gtg aac tgc aat acc agc gcc atc acc cag gcc tgc cct aag gtg       627
Leu Val Asn Cys Asn Thr Ser Ala Ile Thr Gln Ala Cys Pro Lys Val
190                 195                 200 acc ttc gag ccc atc ccc atc cac tac tgc gcc cct gcc ggc ttc gcc       675
Thr Phe Glu Pro Ile Pro Ile His Tyr Cys Ala Pro Ala Gly Phe Ala
205                 210                 215                 220 atc ctg aag tgc aac gac acc gag ttc aat ggc acc ggc ccc tgc aag       723
Ile Leu Lys Cys Asn Asp Thr Glu Phe Asn Gly Thr Gly Pro Cys Lys
            225                 230                 235 aat gtg agc acc gtg cag tgc acc cac ggc atc aag ccc gtg gtg tcc       771
Asn Val Ser Thr Val Gln Cys Thr His Gly Ile Lys Pro Val Val Ser
        240                 245                 250 acc cag ctg ctg ctg aac ggc agc ctg gcc gag aga gaa gtg cgg atc       819
Thr Gln Leu Leu Leu Asn Gly Ser Leu Ala Glu Arg Glu Val Arg Ile
    255                 260                 265 agg agc gag aac atc gcc aac aac gcc aag aac atc atc gtg cag ttc       867
Arg Ser Glu Asn Ile Ala Asn Asn Ala Lys Asn Ile Ile Val Gln Phe
270                 275                 280
```

```
gcc agc ccc gtg aag atc aac tgc atc cgg ccc aac aac aat acc cgg    915
Ala Ser Pro Val Lys Ile Asn Cys Ile Arg Pro Asn Asn Asn Thr Arg
285             290                 295                 300 aag agc tac aga atc ggc cct ggc cag acc ttc tac gcc acc gac att    963
Lys Ser Tyr Arg Ile Gly Pro Gly Gln Thr Phe Tyr Ala Thr Asp Ile
                    305                 310                 315 gtg ggc gac atc aga cag gcc cac tgc aac gtg tcc agg acc gac tgg   1011
Val Gly Asp Ile Arg Gln Ala His Cys Asn Val Ser Arg Thr Asp Trp
                320                 325                 330 aac aac acc ctg aga ctg gtg gcc aac cag ctg cgg aag tac ttc agc   1059
Asn Asn Thr Leu Arg Leu Val Ala Asn Gln Leu Arg Lys Tyr Phe Ser
            335                 340                 345 aac aag acc atc atc ttc acc aac agc agc ggc gga gac ctg gag atc   1107
Asn Lys Thr Ile Ile Phe Thr Asn Ser Ser Gly Gly Asp Leu Glu Ile
350                 355                 360 acc acc cac agc ttc aat tgt ggc ggc gag ttc ttc tac tgc aac acc   1155
Thr Thr His Ser Phe Asn Cys Gly Gly Glu Phe Phe Tyr Cys Asn Thr
365                 370                 375                 380 tcc ggc ctg ttc aat agc acc tgg acc acc aac aac atg cag gag tcc   1203
Ser Gly Leu Phe Asn Ser Thr Trp Thr Thr Asn Asn Met Gln Glu Ser
                385                 390                 395 aac gac acc agc aac ggc acc atc acc ctg ccc tgc cgg atc aag cag   1251
Asn Asp Thr Ser Asn Gly Thr Ile Thr Leu Pro Cys Arg Ile Lys Gln
                400                 405                 410 atc atc cgg atg tgg cag cgc gtg ggc cag gcc atg tac gcc cct ccc   1299
Ile Ile Arg Met Trp Gln Arg Val Gly Gln Ala Met Tyr Ala Pro Pro
            415                 420                 425 atc gag ggc gtg att cgc tgc gag agc aac atc acc ggc ctg atc ctg   1347
Ile Glu Gly Val Ile Arg Cys Glu Ser Asn Ile Thr Gly Leu Ile Leu
430                 435                 440 acc aga gat ggc ggc aac aac aat tcc gcc aac gag acc ttc aga cct   1395
Thr Arg Asp Gly Gly Asn Asn Asn Ser Ala Asn Glu Thr Phe Arg Pro
445                 450                 455                 460 ggc ggc gga gat atc cgg gac aac tgg cgg agc gag ctg tac aag tac   1443
Gly Gly Gly Asp Ile Arg Asp Asn Trp Arg Ser Glu Leu Tyr Lys Tyr
                465                 470                 475 aag gtg gtg aag atc gag ccc ctg ggc gtg gcc ccc acc aga gcc aag   1491
Lys Val Val Lys Ile Glu Pro Leu Gly Val Ala Pro Thr Arg Ala Lys
                480                 485                 490 aga aga gtg gtg gag cgg gag aag aga gcc gtg ggc atc ggc gcc gtg   1539
Arg Arg Val Val Glu Arg Glu Lys Arg Ala Val Gly Ile Gly Ala Val
            495                 500                 505 ttt ctg ggc ttc ctg gga gcc gcc gga tct aca atg gga gcc gcc agc   1587
Phe Leu Gly Phe Leu Gly Ala Ala Gly Ser Thr Met Gly Ala Ala Ser
510                 515                 520 atc acc ctg acc gtg cag gcc aga cag ctg ctg agc ggc atc gtg cag   1635
Ile Thr Leu Thr Val Gln Ala Arg Gln Leu Leu Ser Gly Ile Val Gln
525                 530                 535                 540 cag cag agc aat ctg ctg aga gcc atc gag gcc cag cag cag ctg ctg   1683
Gln Gln Ser Asn Leu Leu Arg Ala Ile Glu Ala Gln Gln Gln Leu Leu
                545                 550                 555 aag ctg aca gtg tgg ggc atc aag cag ctg cag gcc agg gtg ctg gcc   1731
Lys Leu Thr Val Trp Gly Ile Lys Gln Leu Gln Ala Arg Val Leu Ala
                560                 565                 570 gtg gag aga tac ctg agg gac cag cag ctc ctg ggc atc tgg ggc tgc   1779
Val Glu Arg Tyr Leu Arg Asp Gln Gln Leu Leu Gly Ile Trp Gly Cys
            575                 580                 585 agc ggc aag ctg atc tgc acc acc aac gtg ccc tgg aat agc agc tgg   1827
Ser Gly Lys Leu Ile Cys Thr Thr Asn Val Pro Trp Asn Ser Ser Trp
590                 595                 600
```

```
agc aac aag agc tac gac gac atc tgg cag aac atg acc tgg ctg cag      1875
Ser Asn Lys Ser Tyr Asp Asp Ile Trp Gln Asn Met Thr Trp Leu Gln
605             610                 615                 620 tgg gac aag gag atc agc aac tac acc gac atc atc tac agc ctg atc      1923
Trp Asp Lys Glu Ile Ser Asn Tyr Thr Asp Ile Ile Tyr Ser Leu Ile
                625                 630                 635 gag gag agc cag aac cag cag gag aag aac gag cag gat ctg ctg gcc      1971
Glu Glu Ser Gln Asn Gln Gln Glu Lys Asn Glu Gln Asp Leu Leu Ala
            640                 645                 650 ctg gac aag tgg gcc aac ctg tgg aac tgg ttc gac atc agc aag tgg      2019
Leu Asp Lys Trp Ala Asn Leu Trp Asn Trp Phe Asp Ile Ser Lys Trp
        655                 660                 665 ctg tgg tac atc aga tct tgataatcta gaa                               2050
Leu Trp Tyr Ile Arg Ser
    670
```

<210> SEQ ID NO 15
<211> LENGTH: 674
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

```
Met Arg Val Met Glu Ile Gln Arg Asn Cys Gln His Leu Leu Arg Trp
 1               5                  10                  15

Gly Ile Met Ile Leu Gly Met Ile Ile Ile Cys Ser Thr Ala Asp Asn
            20                  25                  30

Leu Trp Val Thr Val Tyr Tyr Gly Val Pro Val Trp Arg Asp Ala Glu
        35                  40                  45

Thr Thr Leu Phe Cys Ala Ser Asp Ala Lys Ala Tyr Ser Thr Glu Lys
    50                  55                  60

His Asn Val Trp Ala Thr His Ala Cys Val Pro Thr Asp Pro Asn Pro
 65                 70                  75                  80

Gln Glu Ile Pro Leu Asp Asn Val Thr Glu Glu Phe Asn Met Trp Lys
                85                  90                  95

Asn Asn Met Val Asp Gln Met His Glu Asp Ile Ile Ser Leu Trp Asp
            100                 105                 110

Gln Ser Leu Lys Pro Cys Val Gln Leu Thr Pro Leu Cys Val Thr Leu
        115                 120                 125

Asn Cys Ser Asn Ala Arg Val Asn Ala Thr Phe Asn Ser Thr Glu Asp
    130                 135                 140

Arg Glu Gly Met Lys Asn Cys Ser Phe Asn Met Thr Thr Glu Leu Arg
145                 150                 155                 160

Asp Lys Lys Gln Gln Val Tyr Ser Leu Phe Tyr Arg Leu Asp Ile Glu
                165                 170                 175

Lys Ile Asn Ser Ser Asn Asn Ser Glu Tyr Arg Leu Val Asn Cys
            180                 185                 190

Asn Thr Ser Ala Ile Thr Gln Ala Cys Pro Lys Val Thr Phe Glu Pro
        195                 200                 205

Ile Pro Ile His Tyr Cys Ala Pro Ala Gly Phe Ala Ile Leu Lys Cys
    210                 215                 220

Asn Asp Thr Glu Phe Asn Gly Thr Gly Pro Cys Lys Asn Val Ser Thr
225                 230                 235                 240

Val Gln Cys Thr His Gly Ile Lys Pro Val Val Ser Thr Gln Leu Leu
                245                 250                 255
```

```
Leu Asn Gly Ser Leu Ala Glu Arg Glu Val Arg Ile Arg Ser Glu Asn
                260                 265                 270

Ile Ala Asn Asn Ala Lys Asn Ile Ile Val Gln Phe Ala Ser Pro Val
            275                 280                 285

Lys Ile Asn Cys Ile Arg Pro Asn Asn Asn Thr Arg Lys Ser Tyr Arg
290                 295                 300

Ile Gly Pro Gly Gln Thr Phe Tyr Ala Thr Asp Ile Val Gly Asp Ile
305                 310                 315                 320

Arg Gln Ala His Cys Asn Val Ser Arg Thr Asp Trp Asn Asn Thr Leu
                325                 330                 335

Arg Leu Val Ala Asn Gln Leu Arg Lys Tyr Phe Ser Asn Lys Thr Ile
            340                 345                 350

Ile Phe Thr Asn Ser Ser Gly Gly Asp Leu Glu Ile Thr Thr His Ser
            355                 360                 365

Phe Asn Cys Gly Gly Glu Phe Phe Tyr Cys Asn Thr Ser Gly Leu Phe
        370                 375                 380

Asn Ser Thr Trp Thr Thr Asn Asn Met Gln Glu Ser Asn Asp Thr Ser
385                 390                 395                 400

Asn Gly Thr Ile Thr Leu Pro Cys Arg Ile Lys Gln Ile Ile Arg Met
                405                 410                 415

Trp Gln Arg Val Gly Gln Ala Met Tyr Ala Pro Pro Ile Glu Gly Val
            420                 425                 430

Ile Arg Cys Glu Ser Asn Ile Thr Gly Leu Ile Leu Thr Arg Asp Gly
435                 440                 445

Gly Asn Asn Asn Ser Ala Asn Glu Thr Phe Arg Pro Gly Gly Gly Asp
    450                 455                 460

Ile Arg Asp Asn Trp Arg Ser Glu Leu Tyr Lys Tyr Lys Val Val Lys
465                 470                 475                 480

Ile Glu Pro Leu Gly Val Ala Pro Thr Arg Ala Lys Arg Arg Val Val
                485                 490                 495

Glu Arg Glu Lys Arg Ala Val Gly Ile Gly Ala Val Phe Leu Gly Phe
            500                 505                 510

Leu Gly Ala Ala Gly Ser Thr Met Gly Ala Ala Ser Ile Thr Leu Thr
            515                 520                 525

Val Gln Ala Arg Gln Leu Leu Ser Gly Ile Val Gln Gln Gln Ser Asn
530                 535                 540

Leu Leu Arg Ala Ile Glu Ala Gln Gln Gln Leu Leu Lys Leu Thr Val
545                 550                 555                 560

Trp Gly Ile Lys Gln Leu Gln Ala Arg Val Leu Ala Val Glu Arg Tyr
                565                 570                 575

Leu Arg Asp Gln Gln Leu Leu Gly Ile Trp Gly Cys Ser Gly Lys Leu
            580                 585                 590

Ile Cys Thr Thr Asn Val Pro Trp Asn Ser Ser Trp Ser Asn Lys Ser
            595                 600                 605

Tyr Asp Asp Ile Trp Gln Asn Met Thr Trp Leu Gln Trp Asp Lys Glu
        610                 615                 620

Ile Ser Asn Tyr Thr Asp Ile Ile Tyr Ser Leu Ile Glu Glu Ser Gln
625                 630                 635                 640

Asn Gln Gln Glu Lys Asn Glu Gln Asp Leu Leu Ala Leu Asp Lys Trp
                645                 650                 655

Ala Asn Leu Trp Asn Trp Phe Asp Ile Ser Lys Trp Leu Trp Tyr Ile
            660                 665                 670

Arg Ser
```

HIV-1 CLADE A CONSENSUS SEQUENCES, ANTIGENS, AND TRANSGENES

CROSS-REFERENCE TO RELATED APPLICATIONS

This application is a continuation of U.S. application Ser. No. 11/757,550, filed Jun. 4, 2007, now U.S. Pat. No. 8,119,144, which claims priority to U.S. Provisional Patent Application No. 60/810,816 filed Jun. 2, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to consensus nucleotide and protein sequences for HIV-1 Clade A antigens, and to nucleotide and protein sequences for Clade A antigens from circulating HIV-1 field isolates wherein the antigen sequences are closely related to the these consensus sequences. In a preferred embodiment, the present invention relates to HIV-1 Clade A transgenes that are derived from such sequences, and that encode either HIV-1 Clade A Gag, Pol (RT and Int), and Nef (referred to as "GRIN"), HIV-1 Clade A Gag, RT, and Nef (referred to as ("GRN"), or HIV-1 Clade A Env. The invention also relates to vectors containing such transgenes, including in a preferred embodiment, adenovirus vectors containing such transgenes. The invention also relates to immunogenic compositions comprising the HIV-1 Clade A antigens, nucleotide sequences, vectors, or transgenes of the invention, and to methods of generating an immune response against HIV-1 in a subject by administering an effective amount of such immunogenic compositions.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HTV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The Gag gene encodes core structural proteins of the nucleocapsid core and matrix. The Pol gene encodes reverse transcriptase (RT), integrase (Int), and viral protease enzymes required for viral replication. The tat gene encodes a protein that is required for elongation of viral transcripts. The rev gene encodes a protein that promotes the nuclear export of incompletely spliced or unspliced viral RNAs. The Vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The Env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas, pp. 454-456). Gp140 is a modified form of the env glycoprotein which contains the external 120-kDa envelope glycoprotein portion and a part of the gp41 portion of env and has characteristics of both gp120 and gp41. The Nef gene is conserved among primate lentiviruses and is one of the first viral genes that is transcribed following infection. In vitro, several functions have been described, including down regulation of CD4 and MHC class surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

The different isolates of HIV-1 have been classified into three groups: M (main), O (outlier) and N (non-M, non-O). The HIV-1 M group dominates the global HIV pandemic (Gaschen et al., (2002) Science 296: 2354-2360). Since the HIV-1 M group began its expansion in humans roughly 70 years ago (Korber et al., Retroviral Immunology, Pantaleo et al., eds., Humana Press, Totowa, N.J., 2001, pp. 1-31), it has diversified rapidly (Jung et al., (2002) Nature 418: 144). The HIV-1 M group consists of a number of different clades (also known as subtypes) as well as variants resulting from the combination of two or more clades, known as circulating recombinant forms (CRFs). Subtypes are defined as having genomes that are at least 25% unique (AIDS epidemic update, December 2002). Eleven clades have been identified and a letter designates each subtype. When clades combine with each other and are successfully established in the environment, as can occur when an individual is infected with two different HIV subtypes, the resulting virus is known as a CRF. Thus far, roughly 13 CRFs have been identified. HIV-1 clades also exhibit geographical preference. For example, Clade A, the second-most prevalent clade, is prevalent in East Africa, while Clade B is common in Europe, the Americas and Australia. Clade C, the most common subtype, is widespread in southern Africa, India and Ethiopia (AIDS epidemic update, December 2002). Even within Clades there is variability in the virus between different strains and viral isolates.

This genetic variability of HIV creates a scientific challenge to vaccine development. One approach that has been suggested is to develop consensus sequences based on the sequences of multiple different HIV strains, and to develop vaccines based on these consensus sequences. The rationale behind such approaches is that the consensus sequences will encode antigens that are conserved among different HIV strains and that such antigens are therefore likely to be useful in generating immune responses against multiple different strains of HIV. HIV-1 clade A consensus sequences have been generated by others. See for example, Nkolola et al. (2004) Gene Ther. 2004. Jul. 11 (13): 1068-80, and Korber B (eds) et al. Human Retroviruses and AIDS: A Compilation and Analysis of Nucleic Acid and Amino Acid Sequences. Los Alamos National Laboratory: Los Alamos, N. Mex., USA, (1997) which involve transgene RENTA and HIVA derived from consensus clade A sequences. However, the consensus sequences described in these articles appear to have been derived from the HIV-1 clade A consensus sequence obtained from the Los Alamos laboratory, and were not generated in the same way as the consensus sequences of the present invention. In addition, these references do not teach use of sequences from actual recently circulating HIV strains which closely match the consensus sequence. Instead they involve using the consensus sequences themselves.

Citation or identification of any document in this application is not an admission that such document is available as prior art to the present application.

SUMMARY OF THE INVENTION

The present invention provides new and improved consensus sequences for HIV-1 Clade A antigens and methods for producing such new and improved consensus sequences. The consensus sequences of the present invention are particularly advantageous because they are based on the antigen sequences of a large number of different HIV-1 Clade A strains, and also because they are based on the sequences of antigens from recently isolated HIV-1 Clade A strains. Accordingly, the consensus sequences of the present invention have superior biological relevance as compared to previously generated HIV-1 Clade A consensus sequences.

Another major advantage of the present invention is that it provides HIV-1 Clade A antigens, and strategies for producing such antigens, that are derived from naturally occurring HIV-1 Clade A strains. These antigens are selected such that they are closely related to, or have a small "protein distance" from, the consensus sequences of the present invention. An advantage of using these naturally occurring sequences with the closest match to the consensus sequences, as opposed to the artificially generated consensus sequences, is that less genetic manipulations are needed to generate these sequences and importantly biological relevance is assured.

In a first aspect the present invention is directed to a consensus amino acid sequence for an HIV-1 Clade A antigen. In one embodiment the invention relates to consensus amino acid sequences for the HIV-1 Clade A antigens Gag, Pol (comprising RT and Int), Nef and Env. In preferred embodiments, the invention relates to the consensus Gag amino acid sequence of FIG. 1, the consensus Pol amino acid sequence of FIG. 3, to the consensus Env amino acid sequence of FIG. 5, and/or the consensus Nef amino acid sequence of FIG. 7.

In a further aspect the present invention is directed to a method of identifying a consensus amino acid sequence for an HIV-1 Clade A antigen of interest comprising determining the amino acid sequence of the antigen of interest in several circulating HIV-1 strains or field isolates, aligning such sequences, and determining the consensus sequence for that antigen.

In another aspect, the invention relates to a method of identifying an HIV-1 Clade A antigen from a circulating strain or field isolate of HIV-1 Clade A that has an amino acid sequence that is similar to the consensus amino acid sequence for that HIV-1 Clade A antigen. In a preferred embodiment the HIV-1 Clade A antigen is selected based the degree of similarity to the consensus sequence, with sequences having the highest degree of similarity to, or the smallest "protein distance" from, the consensus sequence being preferred. In a further preferred embodiment the HIV-1 Clade A antigen is selected from a recently circulating strain or field isolate of HIV-1 Clade A. In a further embodiment the invention relates to HIV-1 Clade A antigens identified using such methods.

In another aspect, the invention relates to a method of identifying an HIV-1 Clade A antigen from a circulating strain or field isolate of HIV-1 Clade A that has an amino acid sequence that is similar to the consensus amino acid sequence for that HIV-1 Clade A antigen, and then making mutations in that sequence to abrogate the biological functions of the sequences. It is preferred that a minimalist approach is used, i.e. that the number of mutations is kept to a minimum so that only those mutations necessary to abrogate function and facilitate obtaining regulatory authority approval are made and un-necessary alteration of the original HIV-1 gene sequences are avoided. For example, in one embodiment the Nef component of GRIN is not altered but rather fusion of the Nef N-terminus to the Int C-terminus abrogates nef function while retaining all the original nucleotide sequences of Nef.

In yet another aspect, the invention relates to a method of improving genetic stability of the HIV-1 Clade A transgene for insertion into viral vector technologies. The PR (protease) component is removed from Gag-full-length Pol-Nef (full length Pol contains PR, and Int and RT) so that only the Int and RT portions of Pol are left. This has the advantage of improved genetic stability and improved cloning and virus rescue properties, particularly using Ad35 and/or Ad11. Removing PR in this way is a minimalist approach in that only the smallest functional subunit of POL is removed, thereby preserving the larger IN & RT functional subunits. The invention also relates to HTV-1 Clade A antigens selected and produced using such methods.

In one embodiment the antigen is a Gag antigen from one of the strains listed in Table 1 and FIG. 2. Preferably the Gag antigen is selected from a strain in which the "protein distance" from the consensus Gag sequence is less than 0.07%, or more preferably less than 0.06%, or more preferably still less than 0.05%. In a preferred embodiment the Gag antigen is from HIV-1 Clade A strain TZA173, strain 97TZ02, strain KNH1144 or strain SE7535UG.

In another embodiment the antigen is a Pol antigen from one of the strains listed in Table 2 and FIG. 4. Preferably the Pol antigen is selected from a strain in which the "protein distance" from the consensus Pol sequence is less than 0.03%, or more preferably less than 0.025%. In a preferred embodiment the Pol antigen is from HIV-1 Clade A strain MSA4070, strain SE7245SO, or strain SE8538.

In a further embodiment the antigen is an Env antigen from one of the strains listed in Table 3 and FIG. 6. Preferably the Env antigen is selected from a strain in which the "protein distance" from the consensus Gag sequence is less than 0.1, or more preferably less than 0.08%, or more preferably less than 0.07%, or more preferably still less than 0.065%. In a preferred embodiment the Env antigen is from HIV-1 Clade A strain KEQ23, strain TZA341, or strain KNH1088.

In another embodiment the antigen is a Nef antigen from one of the strains listed in Table 4 and FIG. 8. Preferably the Nef antigen is selected from a strain in which the "protein distance" from the consensus Gag sequence is less than 0.1%, or more preferably less than 0.08%, or more preferably less than 0.07%, or more preferably less than 0.06, or more preferably still, less than 0.05%. In a preferred embodiment the Nef antigen is from HIV-1 Clade A strain MSA4070, or strain KNH1211, or strain 97TZ03, or strain 99UGA070, or strain SE8891UG.

In yet another aspect, the present invention is directed to the nucleotide sequences that encode the HIV-1 Clade A antigens of the invention. The invention also relates to vectors comprising these nucleotide sequences. The nucleotide sequences of the invention, and the vectors that comprise them, and also the antigens encoded by the nucleotide sequences of the invention, are useful in generating an immune response against HIV Clade A antigens in vivo and are useful in the production of vaccines against HIV-1 Clade A strains. The nucleotide sequences of the invention may also be useful for expressing and producing the HIV-1 Clade A antigens that they encode in cells or in vitro, for example, so that the antigens may be produced, isolated, and/or purified.

The nucleotides of the invention may be altered as compared to the consensus nucleotide sequences, or as compared to the sequences from circulating HIV-1 isolates that are closely related to such consensus sequences. For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

In a preferred embodiment, a single nucleotide sequence encodes a fusion protein comprising the Gag, RT (part of Pol) and Nef antigens of the invention. As used herein the abbreviations "GRN" and "GRtN" are used interchangeably to refer to HIV-1 Clade A fusion proteins comprising the Gag, RT and Nef antigens and to refer to the nucleotide sequences that encode these fusion proteins. In a still more preferred embodiment the nucleotide sequence encoding GRN is inserted into a vector suitable for allowing expression of the GRN fusion protein. Preferably the vector is an adenovirus vector selected from the group consisting of Ad5, Ad35, Ad11, C6, and C7.

In another preferred embodiment a single nucleotide sequence encodes a fusion protein comprising the Gag, Pol (includes RT and Int) and Nef antigens of the invention. As used herein the abbreviations "GRIN" and "GRtIN" are used interchangeably to refer to HIV-1 Clade A fusion proteins comprising the Gag, Pol and Nef antigens and to refer to the nucleotide sequences that encode these fusion proteins. In even more preferred embodiments GRIN has the amino acid sequence illustrated in FIGS. 16A-16J and is encoded by the nucleotide sequence illustrated in FIGS. 16A-16J. In a still more preferred embodiment the nucleotide sequence encoding GRIN is inserted into a vector suitable for allowing expression of the GRIN fusion protein. Preferably the vector is an adenovirus vector, more preferably and adenovirus vector selected from the group consisting of Ad5, Ad35, Ad11, C6, and C7.

In yet another embodiment a single nucleotide sequence of the invention encodes an HIV-1 Clade A Env antigen according to the invention. In a preferred embodiment the Env antigen has the amino acid sequence illustrated in FIGS. 17A-17D and is encoded by the nucleotide sequence illustrated in FIGS. 17A-17D. In a still more preferred embodiment the nucleotide sequence encoding Env is inserted into a vector suitable for allowing expression of the Env protein. Preferably the vector is an adenovirus vector, more preferably and adenovirus vector selected from the group consisting of Ad5, Ad35, Ad11, C6, and C7.

In another embodiment, the present invention provides methods of generating an immune response against HIV-1 Clade A antigens comprising administering to a subject a nucleotide sequence or antigen according to the invention. In preferred embodiments the method of generating an immune response against HIV-1 Clade A comprises administering a nucleotide sequence encoding either GRIN or GRN wherein the nucleotide sequence is contained in an adenovirus vector selected from the group consisting of Ad5, Ad35, Ad11, C6, and C7. In further preferred embodiments, the vectors comprising GRIN or GRN are co-administered with a vector comprising a nucleotide sequence encoding an Env antigen of the invention.

In a further embodiment, the present invention provides immunogenic compositions or vaccine compositions comprising the nucleotide sequences of the invention.

It should be noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following Detailed Description, given by way of example, but not intended to limit the invention to the specific embodiments described, may be best understood in conjunction with the accompanying Figures.

FIG. 1 is a consensus amino acid sequence of the Gag protein of HIV-1 Clade A (SEQ ID NO: 2).

FIG. 2 is a graph illustrating the "distance" of the Gag protein sequences of circulating HIV-Clade A strains to that of the consensus HIV-1 Clade A Gag protein sequence.

FIG. 3 is a consensus amino acid sequence of the Pol protein of HIV-1 Clade A (SEQ ID NO: 3).

FIG. 4 is a graph illustrating the "distance" of the Pol protein sequences of circulating HIV-Clade A strains to that of the consensus HIV-1 Clade A Pol protein sequence.

FIG. 5 is a consensus amino acid sequence of the Env protein of HIV-1 Clade A (SEC) ID NO: 4).

FIG. 7 is a consensus amino acid sequence of the Nef protein of HIV-1 Clade A (SEQ ID NO: 5).

FIG. 10 illustrates the amino acid sequence of the Gag protein from HIV-1 Clade A strain TZA173 (SEQ ID NO: 6) having Genbank accession number AY253305.

FIG. 11 illustrates the amino acid sequence of the Pol protein from HIV-1 Clade A strain MSA4070 (SEQ ID NO: 7) having Genbank accession number AF457081.

FIG. 12 illustrates the amino acid sequence of the Nef protein from HIV-1 Clade A strain MSA4070 (SEQ ID NO: 8) having Genbank accession number AF457081.

FIG. 13 illustrates the amino acid sequence of the Env protein from HIV-1 Clade A strain TZA341 (SEQ ID NO: 9) having Genbank accession number AY253314.

FIGS. 14A-14C provide a sequence of GRIN as inserted into the Ad35 vector (SEQ ID NO: 10).

FIGS. 15A-15B provide a sequence of Env as inserted into the Ad35 vector (SEQ ID NO: 11).

FIGS. 16A-16J provide nucleotide (SEQ ID NO: 12) and amino acid (SEQ ID NO: 13) sequences of the codon optimized GRIN transgene.

FIGS. 17A-17D provide nucleotide (SEQ ID NO: 14) and amino acid (SEQ ID NO: 15) sequences of the codon optimized Env transgene.

Figure 18:
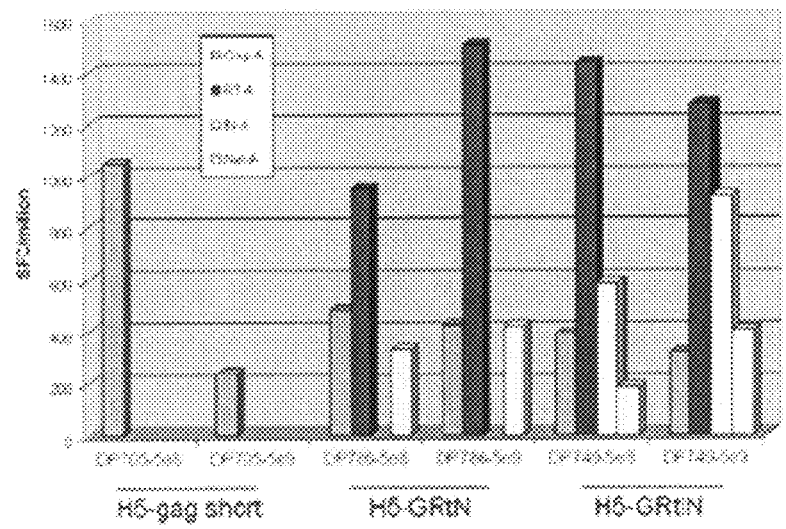

FIG. 18 illustrates graphically the immunogenicity of Ad5-GRIN and Ad5-GRN in mice as measured by IFN-gamma ELIspot assay.

Figure 19:
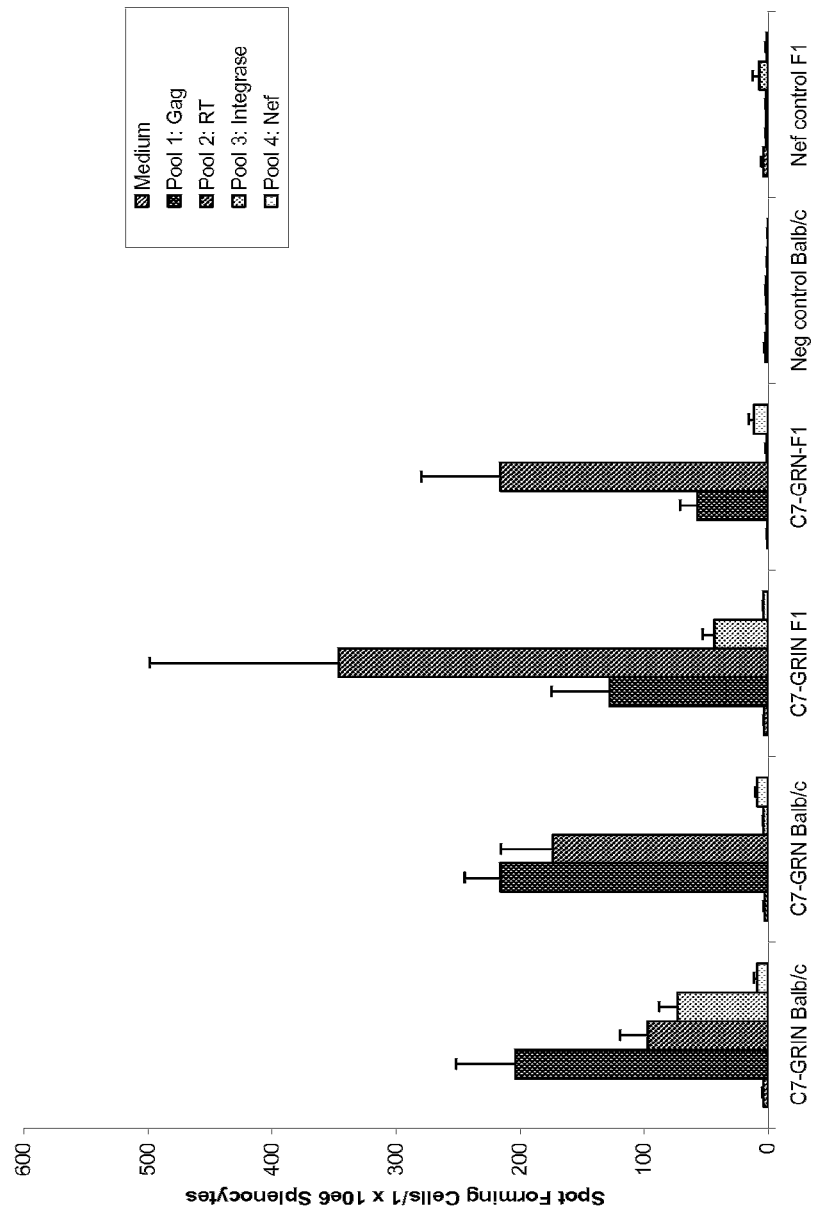

FIG. 19 illustrates graphically the immunogenicity of C7-GRIN and C7-GRN in mice as measured by IFN-gamma ELIspot assay.

Figure 20:
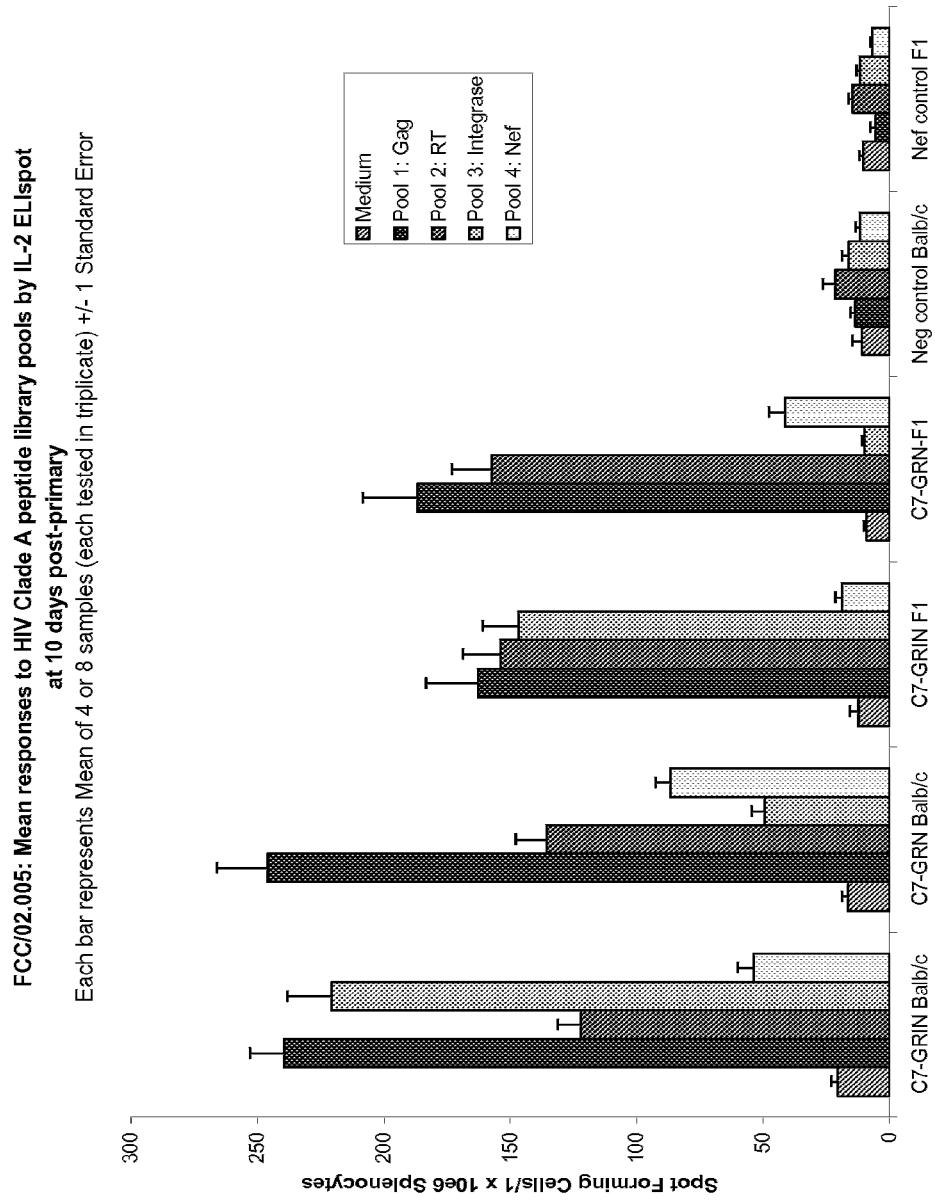

FIG. 20 illustrates graphically the immunogenicity of C7-GRIN and C7-GRN in mice as measured by IL-2 ELIspot assay.

Figure 21:
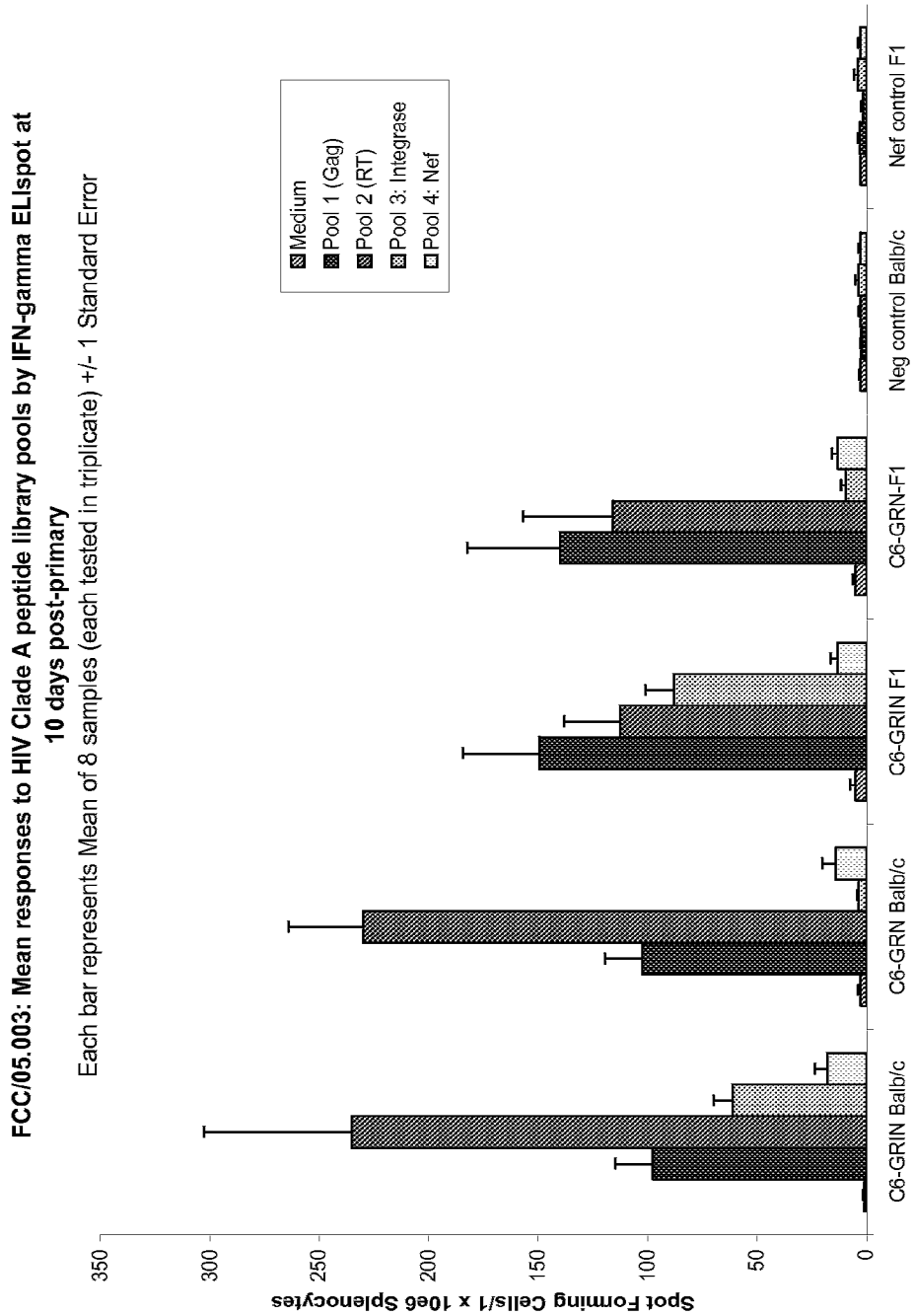

FIG. 21 illustrates graphically the immunogenicity of C6-GRIN and C6-GRN in mice as measured by IFN-gamma ELIspot assay.

Figure 22:
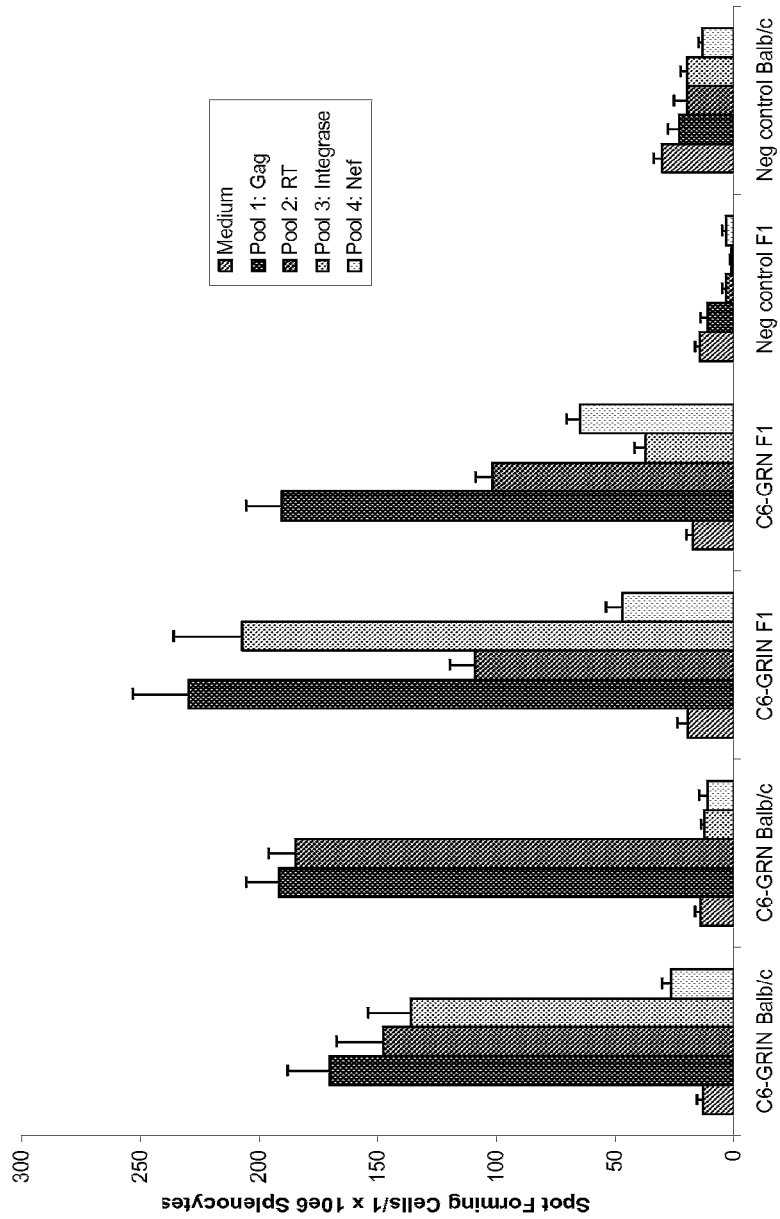

FIG. 22 illustrates graphically the immunogenicity of C6-GRIN and C6-GRN in mice as measured by IL-2 ELIspot assay.

Figure 23A:
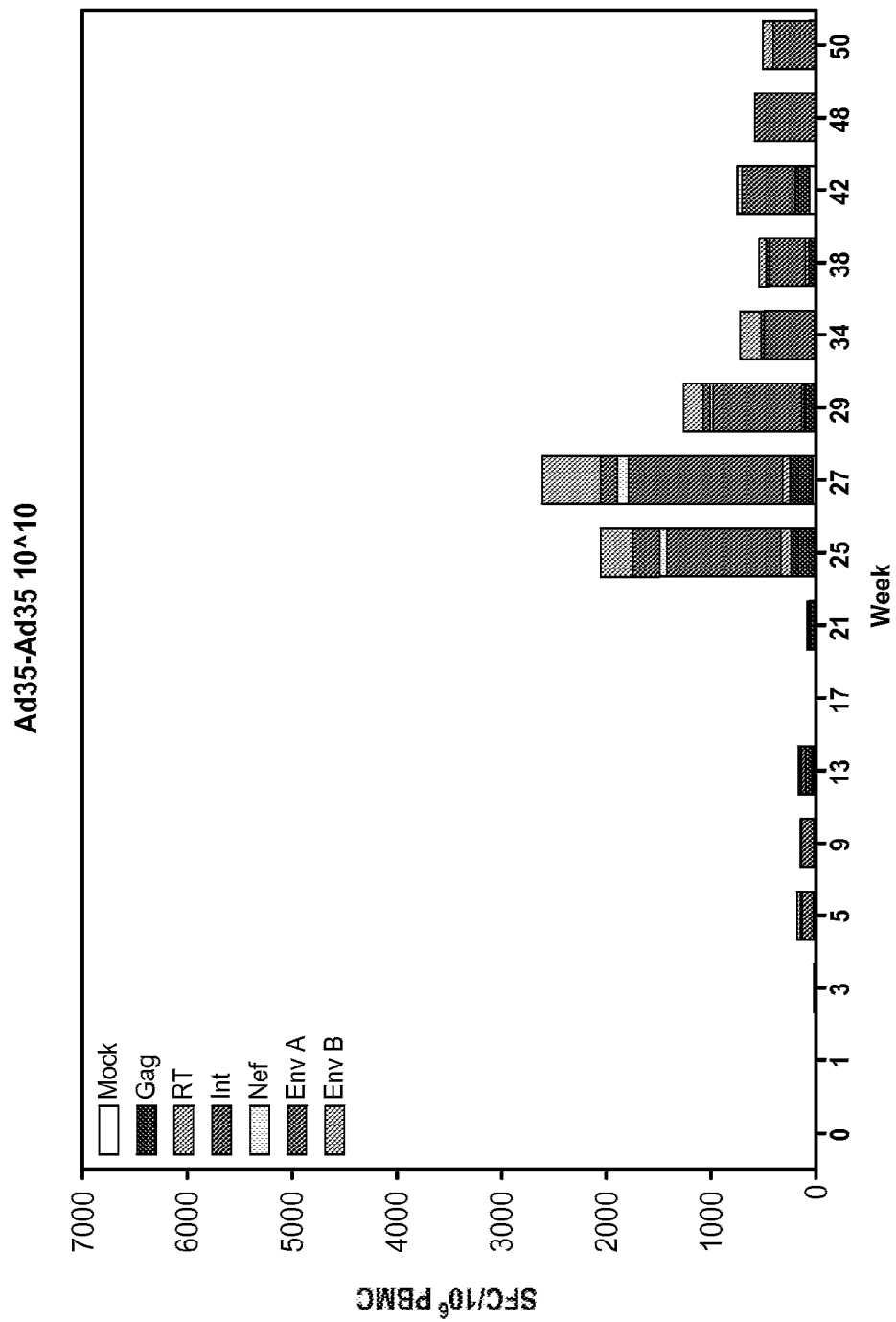

FIG. 23A illustrates IFN-γ immunogenicity of Ad35-GRIN/ENV at the $10^{10}$ vp dose following a month 0-6 immunization schedule in rhesus macaques. Definition of Positive Response For a single peptide pool from a single sample: Response=(mean peptide count—mean no-peptide count). To be positive, a single peptide response must satisfy: 1. Mean peptide count>4× mean no-peptide count from same plate; 2. Coefficient of variation amongst replicate counts≤70% & 3. Response>55 SFC/106. Geometric mean responses for Spot Forming Cells (SFC) per million PBMCs to each antigen component (Gag, RT, IN and ENV) are shown on the y-axis and bleed timepoints in weeks on the x-axis.

Figure 23B:
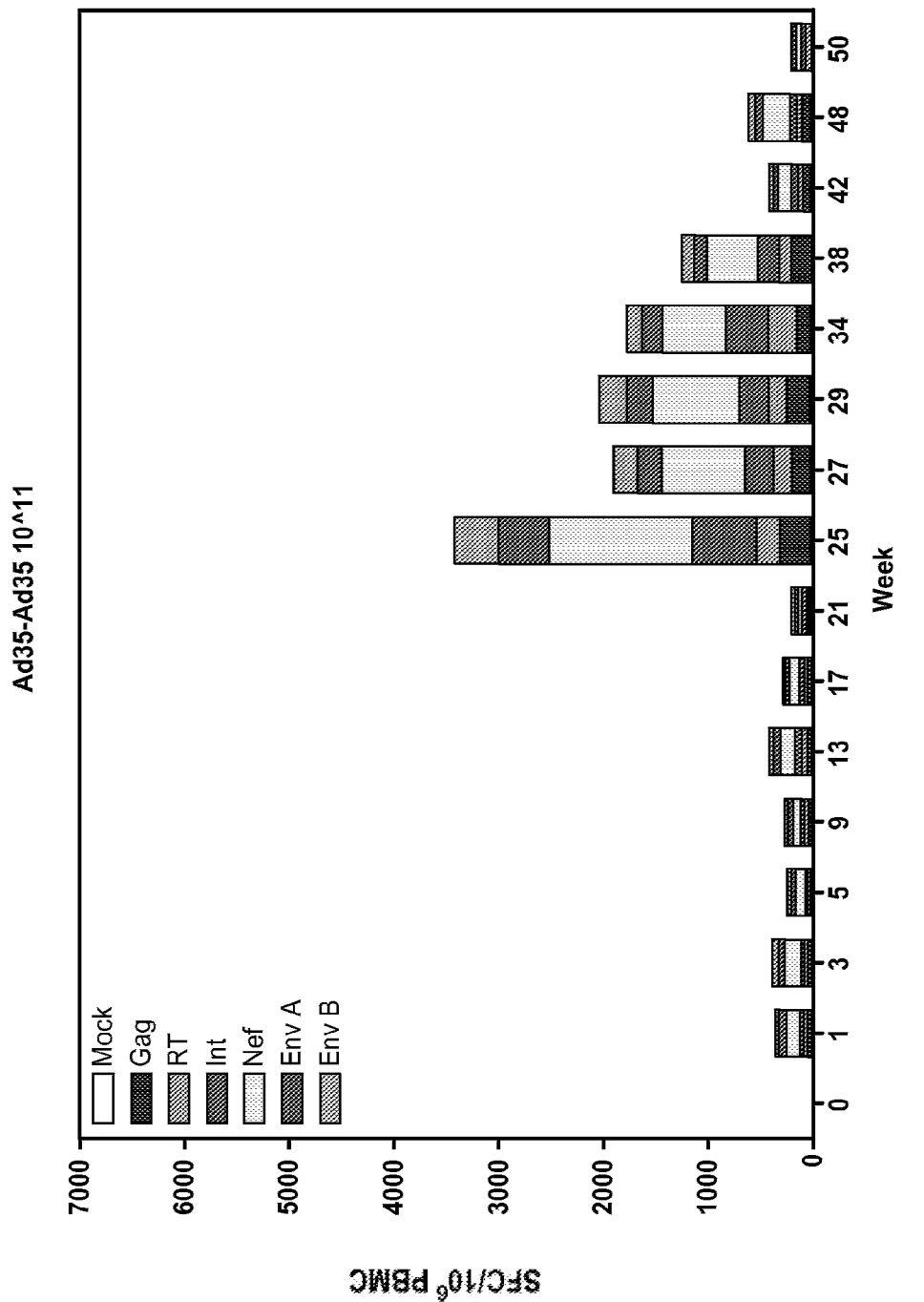

FIG. 23B illustrates IFN-γ ELISpot immunogenicity of Ad35-GRIN/ENV at the $10^{11}$ vp dose following a month 0-6 immunization schedule in rhesus macaques. Definition of Positive Response For a single peptide pool from a single sample: Response=(mean peptide count—mean no-peptide count). To be positive, a single peptide response must satisfy: 1. Mean peptide count>4× mean no-peptide count from same plate; 2. Coefficient of variation amongst replicate counts≤70% & 3. Response>55 SFC/106. Geometric mean responses for Spot Forming Cells (SFC) per million PBMCs to each antigen component (Gag, RT, IN and ENV) are shown on the y-axis and bleed timepoints in weeks on the x-axis.

DETAILED DESCRIPTION OF THE INVENTION

The present invention relates to consensus nucleotide and protein sequences for HIV-1 clade A antigens, and to circulating HIV-1 field isolates that closely match these consensus sequences. The invention also relates to altered version of these sequences, which may be altered such that the function of the gene products in vivo is abrogated, to constructs and vectors comprising the sequences of the invention, and to immunogens, immunogenic compositions, and vaccines made using the sequences of the invention. The invention also relates to methods of generating an immune response against HIV-1 Clade A antigens in a subject and to methods of inducing protective immunity against challenge with HIV-1. The various embodiments of the invention are summarized above in the section entitled "Summary of the Invention." Further details of the invention are provided in the Detailed Description and Examples that follow, and also in the Drawings.

As described in the above "Summary of the Invention" and the "Examples" below, the present invention provides HIV-1 Clade A consensus antigens, and also antigens from circulating HTV-1 Clade A strains that are closely related to these consensus sequences. The invention also provides HIV-1 transgenes and antigens encoded by these transgenes. These transgenes comprise sequences encoding the HIV-1 Clade A antigens of the invention, for example the Gag, Pol, Env, Nef, RT, and Int antigens of the invention. For example, in one preferred embodiment the present invention provides a GRIN (also referred to as GRtIN) transgene which comprises Gag, Pol (both RT and Int) and Nef antigens of the invention. In another preferred embodiment the present invention provides a GRN (also referred to as GRtN) transgene which comprises the Gag, RT and Nef antigens of the invention. In another embodiment the present invention provides an Env transgene which comprises and Env antigens of the invention.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

It should be understood that the proteins and antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

In one embodiment the present invention is directed to "consensus" amino acid sequences for an HIV-1 Clade A antigens. In one embodiment the invention relates to consensus amino acid sequences for the HIV-1 Clade A antigens Gag, Pol (comprising RT and Int), Nef and Env. In preferred embodiments, the invention relates to a consensus Gag amino acid sequence of FIG. 1, the consensus Pol amino acid sequence of FIG. 3, to a consensus Env amino acid sequence of FIG. 5, and/or a consensus Nef amino acid sequence of FIG. 7. In a further aspect the present invention is directed to a method of identifying a consensus amino acid sequence for an HIV-1 Clade A antigen of interest comprising obtaining the amino acid sequence of the antigen of interest in several circulating HIV-1 strains or field isolates, aligning such sequences, and determining the consensus sequence for that antigen. For example, in one embodiment a database is generated using available sequences for HIV-1 Clade A non-recombinant circulating strains, and the individual HIV-1 genes (for example gag, pol, nef and env) from all the sequences in the database are then aligned, with dashes inserted to maintain alignment in regions with insertions or deletions in the sequence, and a 50% consensus sequence can then be derived.

The present invention also relates to methods of identifying antigens from naturally occurring HIV-1 Clade A strains that have an amino acid sequence that has a small "protein distance" from the consensus amino acid sequence of that antigen. The "protein distance" is a measure of the level of similarity or difference between two amino acid sequences. Two amino acid sequences that are very similar have a low protein distance. Two amino acid sequences that are very different have a high protein distance. Protein distances are preferably calculated using the Dayhoff PAM250 substitution matrix (M. O. Dayhoff, ed., 1978, Atlas of Protein Sequence and Structure, Vol. 5) which weights substitutions according to the degree of biochemical similarity. However, other methods for determining protein distance can also be used.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As described in the above "Summary of the Invention" and the "Examples" below, the present invention provides HIV-1 Clade A consensus antigens and to the nucleotide sequences that encode these consensus antigen. The invention also relates to antigens from circulating HIV-1 Clade A strains that are closely related to these consensus sequences, and to the nucleotide sequences that encode them. The invention also provides HIV-1 Clade A transgenes which comprise sequences encoding the HIV-1 Clade A antigens of the invention. As used herein the term "transgene" is used to refer to "recombinant" nucleotide sequences that are derived from either the HIV-1 Clade A consensus nucleotide sequences of the invention, or from the nucleotide sequences that encode the antigens from recently circulating HIV-1 Clade A strains that have been identified as being closely matched to these consensus sequences. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc. For example, in preferred embodiments the present invention provides the GRIN, GRN, and Env transgenes.

The nucleotides of the invention may be altered as compared to the consensus nucleotide sequences, or as compared to the sequences from circulating HIV-1 isolates that are closely related to such consensus sequences. For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

The types of mutations that can be made to abrogate the in vivo function of the antigens include, but are not limited to, the following which are also described in Example 7: Mutation of Gly2 to Ala in Gag to remove a myristylation site and prevent formation of virus-like-particles (VLPs); Mutation of Gag to avoid slippage at the natural frame shift sequence to leave the conserved amino acid sequence (NFLG) (SEQ ID NO: 1) intact and allow only the full-length GagPol protein product to be translated; Mutation of RT Asp185 to Ala and mutation of Asp186 to Ala to inactivate active enzyme residues. Mutation of Int Asp64 to Ala, and mutation of Asp116 to Ala and mutation of Glu152 to Ala to inactivate active enzyme residues.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. For example, codons may be optimized for human usage as illustrated in Example 8. However, any other suitable methods of codon optimization may be used. Such methods, and the selection of such methods, are well known to those of skill in the art. In addition, there are several companies that will optimize codons of sequences, such as Geneart (geneart-.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and transgenes of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the HIV-1 Clade A transgenes of the present invention may be used in accordance with the present invention. In certain embodiments, the HIV-1 Clade A transgenes of the present invention may be used in vitro (such as using cell-free expression systems) and/or in cultured cells grown in vitro in order to produce the encoded HIV-1 antigens which may then be used for various applications such as in the production of proteinaceous vaccines. For such applications, any vector that allows expression of the HIV-1 Clade A transgenes in vitro and/or in cultured cells may be used.

For applications where it is desired that the transgenes be expressed in vivo, for example when the transgenes of the invention are used in DNA or DNA-containing vaccines, any vector that allows for the expression of the HIV-1 Clade A transgenes of the present invention and is safe for use in vivo may be used. In preferred embodiments the vectors used are safe for use in humans, mammals and/or laboratory animals.

In order for the transgenes of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the transgenes of the invention can be expressed.

For example, when the aim is to express the transgenes of the invention in vitro, or in cultured cells, or in any prokaryotic or eukaryotic system for the purpose of producing the protein(s) encoded by that transgene, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the transgenes under the identified circumstances.

When the aim is to express the transgenes of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the transgenes of the invention in a laboratory animal, such as for pre-clinical testing of the HIV-1 immunogenic compositions and vaccines of the invention. In other embodiments, it will be desirable to express the transgenes of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

In particularly preferred embodiments adenovirus vectors are used. Many adenovirus vectors are known in the art and any such suitable vector my be used. In preferred embodiments the adenovirus vector used is selected from the group consisting of the Ad5, Ad35, Ad11, C6, and C7 vectors.

The sequence of the Adenovirus 5 ("Ad5") genome has been published. (Chroboczek, J., Bieber, F., and Jacrot, B. (1992) The Sequence of the Genome of Adenovirus Type 5 and Its Comparison with the Genome of Adenovirus Type 2, Virology 186, 280-285; the contents if which is hereby incorporated by reference). Ad35 vectors are described in U.S. Pat. Nos. 6,974,695, 6,913,922, and 6,869,794. Ad11 vectors are described in U.S. Pat. No. 6,913,922. C6 adenovirus vectors are described in U.S. Pat. Nos. 6,780,407; 6,537,594; 6,309,647; 6,265,189; 6,156,567; 6,090,393; 5,942,235 and 5,833,975. C7 vectors are described in U.S. Pat. No. 6,277,558.

Adenovirus vectors that are E1-defective or deleted, E3-defective or deleted, and/or E4-defective or deleted may also be used. Certain adenoviruses having mutations in the E1 region have improved safety margin because E1-defective adenovirus mutants are replication-defective in non-permissive cells, or, at the very least, are highly attenuated. Adenoviruses having mutations in the E3 region may have enhanced the immunogenicity by disrupting the mechanism whereby adenovirus down-regulates MHC class I molecules. Adenoviruses having E4 mutations may have reduced immunogenicity of the adenovirus vector because of suppression of late gene expression. Such vectors may be particularly useful when repeated re-vaccination utilizing the same vector is desired. Adenovirus vectors that are deleted or mutated in E1, E3, E4, E1 and E3, and E1 and E4 can be used in accordance with the present invention.

Furthermore, "gutless" adenovirus vectors, in which all viral genes are deleted, can also be used in accordance with the present invention. Such vectors require a helper virus for their replication and require a special human 293 cell line expressing both E1a and Cre, a condition that does not exist in natural environment. Such "gutless" vectors are non-immunogenic and thus the vectors may be inoculated multiple times for re-vaccination. The "gutless" adenovirus vectors can be used for insertion of heterologous inserts/genes such as the transgenes of the present invention, and can even be used for co-delivery of a large number of heterologous inserts/genes.

The present invention also encompasses a design that puts the Env and GRIN on separate vectors to allow assessment of whether inclusion of Env is beneficial or detrimental in terms of cell-mediated immunity (CMI) and protective efficacy. The benefits and/or detriments of Env on CMI and protective efficacy remains an open question in the HTV vaccine field. Therefore, the present invention provides for the assessment of Env on CMI and protective efficacy. It is within the purview of one of skill in the art to utilize the transgenes and vectors of the present invention to determine the effect of Env on CMI and protective efficacy.

The nucleotide sequences and vectors of the invention can be delivered to cells, for example if aim is to express and the HIV-1 antigens in cells in order to produce and isolate the expressed proteins, such as from cells grown in culture. For expressing the transgenes in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antigens can be carried out in any suitable type of host cells, such as bacterial cells, yeast, insect cells, and mammalian cells. The HIV-1 Clade A antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

Following expression, the antigens of the invention can be isolated and/or purified or concentrated using any suitable technique known in the art. For example, anion or cation exchange chromatography, phosphocellulose chromatography, hydrophobic interaction chromatography, affinity chromatography, immuno-affinity chromatography, hydroxyapatite chromatography, lectin chromatography, molecular sieve chromatography, isoelectric focusing, gel electrophoresis, or any other suitable method or combination of methods can be used.

In preferred embodiments, the nucleotide sequences and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the transgenes of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences and/or antigens if the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the HIV-1 Clade A antigens of the invention to a subject, such as a human, such that the HIV-1 Clade A antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol diolcate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71 (3): 538-44; Ahmad-Nejad, P. et al (2002) Eur. J. Immunol. 32 (7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20 (29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169 (7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22 (13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167 (6): 3398-405), polyphosphazenes (Allcock, H. R. (1998) App. Organometallic Chem. 12 (10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77 (3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

The immunogenic compositions can be designed to introduce the HIV-1 Clade A antigens, nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulations can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the HIV-1 Clade A antigens, nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, especially DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the HIV-1 Clade A antigens of the invention, (preferably GRIN, GRN, or Env, or a combination thereof), one or more times to a subject wherein the HIV-1 Clade A antigen(s) are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. Many other HIV immunogens are known in the art, one such preferred immunogen is HIVA (described in WO 01/47955), which can be administered as a protein, on a plasmid (e.g., pTHr.HIVA) or in a viral vector (e.g., MVA.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an HIV-1 Clade A antigen of the invention, a nucleic acid encoding an HIV-1 Clade A antigen of the invention or an expression vector, preferably an adenovirus vector, encoding an HIV-1 Clade A antigen of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

It is to be understood and expected that variations in the principles of invention as described above, and as described in the below example, may be made by one skilled in the art and it is intended that such modifications, changes, and substitutions are to be included within the scope of the present invention.

The following non-limiting examples are given for the purpose of illustrating various embodiments of the invention.

EXAMPLES

Example 1

Consensus Sequence for Gag of HIV Clade A

TABLE 1

| | Distance from consensus | Country | Year |
|---|---|---|---|
| A_consensu | 0 | | |
| A_97TZ02_1 | 0.04081 | TZ | 1997 |
| A_TZA173_1 | 0.0425 | TZ | 2001 |
| A_KNH1144_ | 0.04259 | KE | 2000 |
| A_SE7535UG | 0.04303 | UG | 1994 |
| A_KNH1211_ | 0.04463 | KE | 2000 |
| A_KSM4024_ | 0.04684 | KE | 2000 |
| A_KNH1207_ | 0.04701 | KE | 2000 |
| A_SE6594UG | 0.04709 | UG | 1993 |
| A_92UG037_ | 0.05079 | UG | 1992 |
| A_TZA195_1 | 0.05127 | TZ | 2001 |
| A_MSA4079_ | 0.05279 | KE | 2000 |
| A_TZA341_1 | 0.05523 | TZ | 2001 |
| A_MSA4072_ | 0.05583 | KE | 2000 |

TABLE 1-continued

| | Distance from consensus | Country | Year |
|---|---|---|---|
| A_MSA4076_ | 0.056 | KE | 2000 |
| A_KNH1199_ | 0.05687 | KE | 2000 |
| A_MSA4070_ | 0.05947 | KE | 2000 |
| A_98UG5713 | 0.06038 | UG | 1998 |
| A_KEQ23-17 | 0.06072 | KE | 1994 |
| A_KNH1209_ | 0.06101 | KE | 2000 |
| A_NKU3005_ | 0.06108 | KE | 2000 |
| A_SE7253SO | 0.06113 | SO | 1994 |
| A_98UG5713 | 0.06119 | UG | 1998 |
| A_SE8538TZ | 0.06137 | TZ | 1995 |
| A_KNH1088_ | 0.06262 | KE | 1999 |
| A_KER2008_ | 0.065 | KE | 2000 |
| A_99UGA070 | 0.06531 | UG | 1999 |
| A_KER2012- | 0.06654 | KE | 2000 |
| A_KER2009_ | 0.0674 | KE | 2000 |
| A_99UGG033 | 0.06871 | UG | 1999 |
| A_KSM4030- | 0.07026 | KE | 2000 |
| A_KSM4021- | 0.07145 | KE | 1999 |
| A_98UG5713 | 0.07189 | UG | 1998 |
| A_SE8891UG | 0.07197 | UG | 1995 |
| A_SE8131UG | 0.07462 | UG | 1995 |
| A_97TZ03_1 | 0.07653 | TZ | 1997 |
| A_KNH1135_ | 0.07687 | KE | 1999 |
| A_98UG5714 | 0.0781 | UG | 1998 |
| A_UGU455_1 | 0.08349 | UG | 1985 |
| A_MSA4069_ | 0.08867 | KE | 2000 |

The amino acid sequences of the Gag proteins of 39 non-recombinant HIV Clade A strains were analyzed. Table 1 lists the 39 strains used, and refers to each by its Genbank accession number. Table 1 also identifies the country and year of isolation of each of these 39 strains. 20 of the strains were from Kenya, 12 from Uganda, 6 from Tanzania, and 1 from Somalia. 20 of the strains were isolated between 2000 and 2002, 10 were isolated between 1997 and 1999, 6 were isolated between 1994 and 1996 and 3 were isolated before 1993.

The Gag protein sequences were aligned with spaces added to preserve alignment in regions with insertions or deletions. A 50% consensus sequence was derived. The consensus amino acid sequence is shown FIG. 1. In FIG. 1 the spaces that were added to preserve alignment in regions with insertions or deletions are represented by dashes, and the positions for which a 50% consensus was not attained are represented by an "X.

For each of the 39 sequences used to generate the consensus sequence, the "distance" of that sequence from the consensus sequence was calculated using the Dayhoff PAM250 substitution matrix, which weights substitutions according to the degree of biochemical similarity. As shown in Table 1, the distance of each strain's sequence from the consensus sequence ranged from 4 to 9%.

Figure 2:
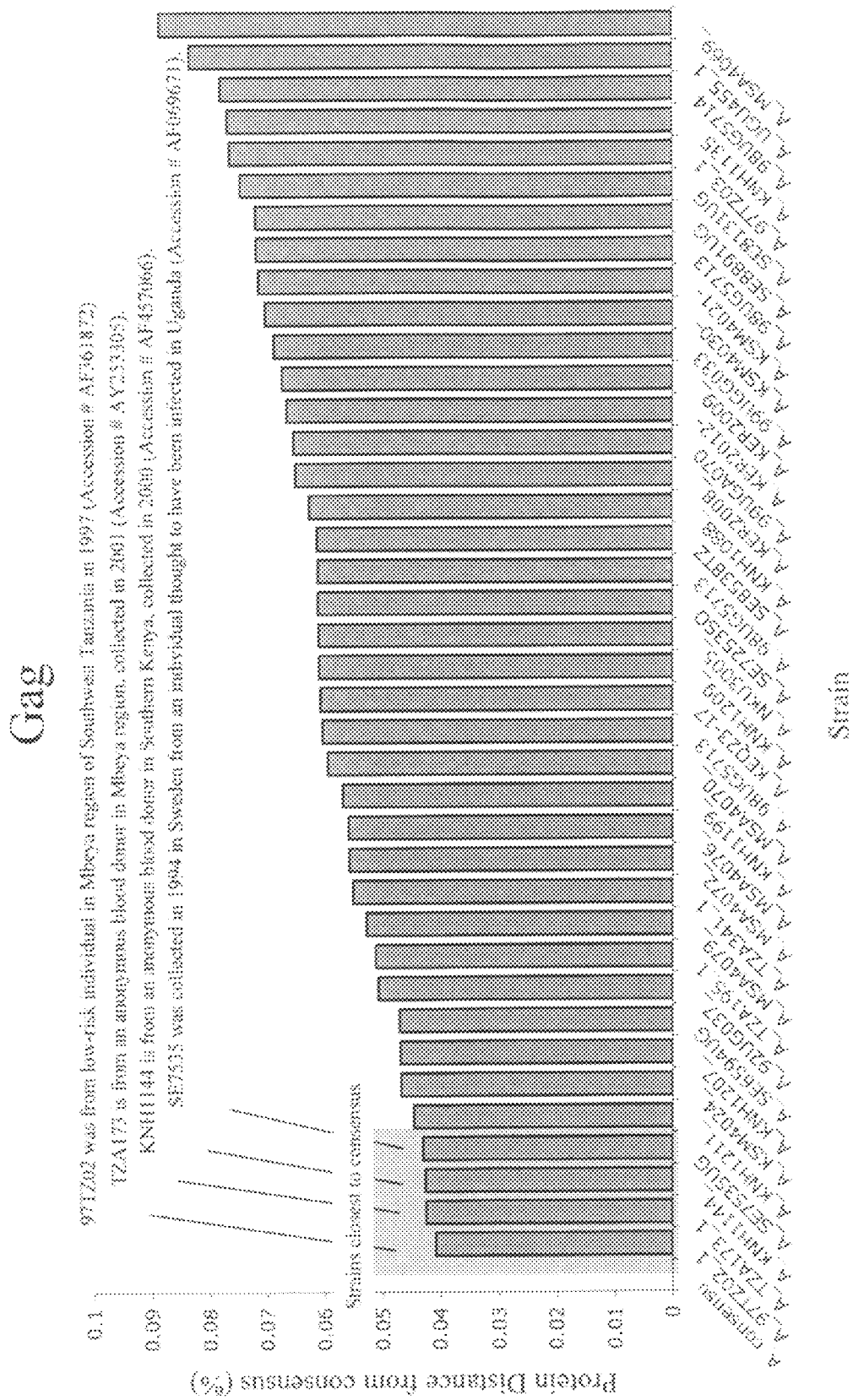

FIG. 2 illustrates the distance of each strain's amino acid sequence from the consensus amino acid sequence in graphical form, and identifies the four strains having sequences that are closest to the consensus sequences. These four strains are strain 97TZ02 which from a low-risk individual in the Mbeya region of southwest Tanzania in 1997 which has Genbank accession number AF361872, strain TZA173 collected from an anonymous blood donor in the Mbeya region of southwest Tanzania in 2001 which has Genbank accession number AY253305, strain KNH1144 collected from an anonymous blood donor in southern Kenya in 2000 which has Genbank accession number AF4587006, and strain SE7535 collected in 1994 in Sweden from an individual thought to have been infected in Uganda which has Genbank accession number AF069671.

Example 2

Consensus Sequence for Pol of HIV Clade A

The amino acid sequences of the Pol proteins of 36 non-recombinant HIV Clade A strains were analyzed. Table 2 lists the 36 strains used, and refers to each by its Genbank accession number. Table 2 also identifies the country and year of isolation of each of these 36 strains. 20 of the strains were from Kenya, 9 from Uganda, 6 from Tanzania, and 1 from Somalia. 19 of the strains were isolated between 2000 and 2002, 10 were isolated between 1997 and 1999, 4 were isolated between 1994 and 1996 and 3 were isolated before 1993.

The Pol protein sequences were aligned. There were no insertions or deletions. A 50% consensus sequence was derived. The consensus amino acid sequence is shown FIG. 3. In FIG. 3 the positions for which a 50% consensus was not attained are represented by an "X". There were 4 such positions out of 947 amino acid residues. For each of the 36 sequences used to generate the consensus sequence, the "distance" of that sequence from the consensus sequence was calculated using the Dayhoff PAM250 substitution matrix, which weights substitutions according to the degree of biochemical similarity. As shown in Table 2, the distance of each strain's sequence from the consensus sequence ranged from 1.5 to 4.8%.

TABLE 2

| | Distance from consensus | Country | Year |
|---|---|---|---|
| A_pol.cons | 0 | | |
| A_MSA4070_ | 0.01479 | KE | 2000 |
| A_SE7253SO | 0.01582 | SO | 1994 |
| A_SE8538TZ | 0.01898 | TZ | 1995 |
| A_KER2012- | 0.02329 | KE | 2000 |
| A_97TZ02_3 | 0.0235 | TZ | 1997 |
| A_KEQ23-17 | 0.02445 | KE | 1994 |
| A_KNH1211_ | 0.02449 | KE | 2000 |
| A_TZA341_3 | 0.0246 | TZ | 2001 |
| A_KSM4024_ | 0.02528 | KE | 2000 |
| A_97TZ03_3 | 0.02544 | TZ | 1997 |
| A_KNH1088_ | 0.02544 | KE | 1999 |
| A_MSA4076_ | 0.02564 | KE | 2000 |
| A_KNH1207_ | 0.0265 | KE | 2000 |
| A_NKU3005_ | 0.02661 | KE | 2000 |
| A_TZA173_3 | 0.02756 | TZ | 2001 |
| A_MSA4079_ | 0.02762 | KE | 2000 |
| A_KER2009_ | 0.02765 | KE | 2000 |
| A_TZA195_3 | 0.02881 | TZ | 2001 |
| A_KSM4021- | 0.02881 | KE | 1999 |
| A_SE7535UG | 0.02883 | UG | 1994 |
| A_MSA4069_ | 0.02886 | KE | 2000 |
| A_SE6594UG | 0.02889 | UG | 1993 |
| A_98UG5713 | 0.02975 | UG | 1998 |
| A_KNH1135_ | 0.0299 | KE | 1999 |
| A_92UG037_ | 0.02993 | UG | 1992 |
| A_KNH1209_ | 0.03202 | KE | 2000 |
| A_99UGG033 | 0.03291 | UG | 1999 |
| A_KER2008_ | 0.03294 | KE | 2000 |
| A_KSM4030- | 0.0343 | KE | 2000 |
| A_KNH1199_ | 0.03439 | KE | 2000 |
| A_99UGA070 | 0.03537 | UG | 1999 |
| A_MSA4072_ | 0.03625 | KE | 2000 |
| A_KNH1144_ | 0.03863 | KE | 2000 |
| A_98UG5713 | 0.04178 | UG | 1998 |
| A_UGU455_3 | 0.04294 | UG | 1985 |
| A_98UG5713 | 0.04808 | UG | 1998 |

Figure 4:
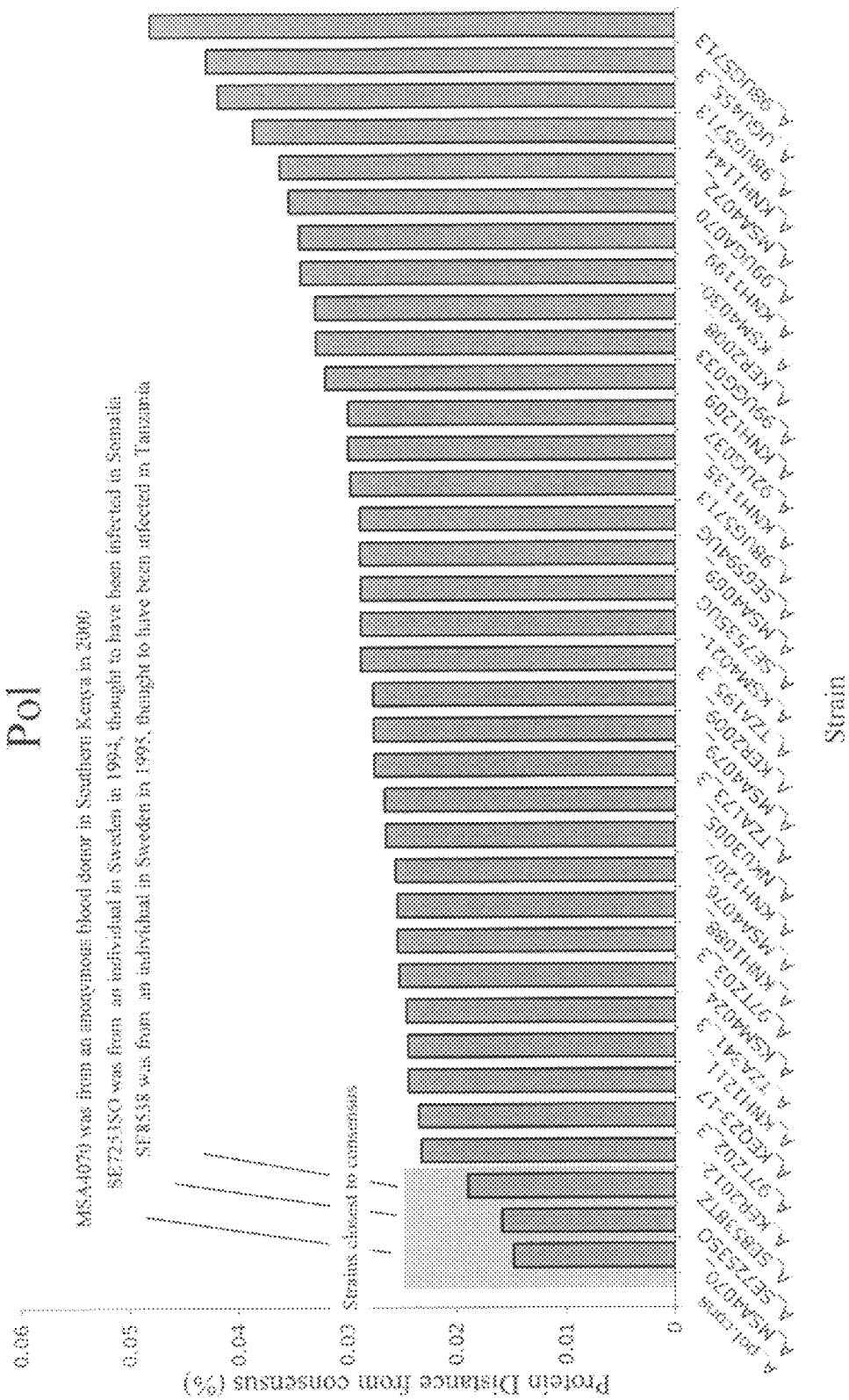

FIG. 4 illustrates the distance of each strain's amino acid sequence from the consensus amino acid sequence in graphical form, and identifies the three strains having sequences that are closest to the consensus sequences. These three strains are strain MSA4070 from an anonymous blood donor in Southern Kenya in 2000, strain SE7235SO which was collected in 1994 from an individual in Sweden thought to have been infected in Somalia, and strain SE8538 which was collected in 1995 from an individual in Sweden thought to have been infected in Tanzania.

Example 3

Consensus Sequence for Env of HIV Clade A

TABLE 3

| | Dist from A.cons | country | year |
|---|---|---|---|
| A.cons | 0 | | |
| A_KEQ23-17 | 0.06307 | KE | 1994 |
| A_TZA341_1 | 0.06413 | TZ | 2001 |
| A_KNH1088_ | 0.06524 | KE | 1999 |
| A_KNH1209_ | 0.0699 | KE | 2000 |
| A_KNH1144_ | 0.07088 | KE | 2000 |
| A_99UGA070 | 0.07365 | UG | 1999 |
| A_MSA4072_ | 0.07516 | KE | 2000 |
| A_KSM4021- | 0.0778 | KE | 1999 |
| A_97TZ02_1 | 0.07825 | TZ | 1997 |
| A_KNH1199_ | 0.07883 | KE | 2000 |
| A_MSA4079_ | 0.07944 | KE | 2000 |
| A_SE7535UG | 0.08375 | UG | 1994 |
| A_SE8538TZ | 0.08432 | TZ | 1995 |
| A_98UG5713 | 0.08462 | UG | 1998 |
| A_97TZ03_1 | 0.08541 | TZ | 1997 |
| A_MSA4070_ | 0.0874 | KE | 2000 |
| A_NKU3005_ | 0.0884 | KE | 2000 |
| A_TZA173_1 | 0.09046 | TZ | 2001 |
| A_KNH1207_ | 0.09106 | KE | 2000 |
| A_TZA195_1 | 0.09389 | TZ | 2001 |
| A_MSA4076_ | 0.09517 | KE | 2000 |
| A_92UG037_ | 0.098 | UG | 1992 |
| A_98UG5714 | 0.09816 | UG | 1998 |
| A_SE7253SO | 0.09886 | SO | 1994 |
| A_KER2012- | 0.09984 | KE | 2000 |
| A_98UG5713 | 0.10139 | UG | 1998 |
| A_SE6594UG | 0.10195 | UG | 1993 |
| A_SE8891UG | 0.10225 | UG | 1995 |
| A_UGU455_1 | 0.10314 | UG | 1985 |
| A_KER2009_ | 0.10338 | KE | 2000 |
| A_KNH1211_ | 0.11319 | KE | 2000 |
| A_SE8131UG | 0.11321 | UG | 1995 |
| A_MSA4069_ | 0.11507 | KE | 2000 |
| A_99UGG033 | 0.11653 | UG | 1999 |
| A_KNH1135_ | 0.11713 | KE | 1999 |
| A_KER2008_ | 0.12689 | KE | 2000 |

The amino acid sequences of the Env proteins of 36 non-recombinant HIV Clade A strains were analyzed. Table 3 lists the 36 strains used, and refers to each by its Genbank accession number. Table 3 also identifies the country and year of isolation of each of these 36 strains. 18 of the strains were from Kenya, 11 from Uganda, 6 from Tanzania, and 1 from Somalia. 17 of the strains were isolated between 2000 and 2002, 10 were isolated between 1997 and 1999, 6 were isolated between 1994 and 1996 and 3 were isolated before 1993.

The Env protein sequences were aligned with spaces added to preserve alignment in regions with insertions or deletions. There were many regions with extensive heterogeneity in the length of insertions/deletions. A 50% consensus sequence was derived. The consensus amino acid sequence is shown FIG. 5. In FIG. 5 the spaces that were added to preserve alignment in regions with insertions or deletions are represented by dashes, and the positions for which a 50% consensus was not attained are represented by an "X". There were many amino acid positions for which a 50% consensus was not attained.

For each of the 36 sequences used to generate the consensus sequence, the "distance" of that sequence from the consensus sequence was calculated using the Dayhoff PAM250 substitution matrix, which weights substitutions according to the degree of biochemical similarity. As shown in Table 3, the distance of each strain's sequence from the consensus sequence ranged from 6.3 to 12.7%.

Figure 6:
FIG. 6 is a graph illustrating the "distance" of the Env protein sequences of circulating HIV-Clade A strains to that of the consensus HIV-1 Clade A Env protein sequence.

FIG. 6 illustrates the distance of each strain's amino acid sequence from the consensus amino acid sequence in graphical form, and identifies the three strains having sequences that are closest to the consensus sequences. These three strains were KEQ23 from a CSW in Kenya in 1994 (what is a CSW), TZA341 which was from an anonymous blood donor in Tanzania in 2002, and KNH1088 which was from an anonymous blood donor in Kenya in 1999.

Example 4

Consensus Sequence for Nef of HIV Clade A

The amino acid sequences of the Nef proteins of 38 non-recombinant HIV Clade A strains were analyzed. Table 4 lists the 38 strains used, and refers to each by its Genbank accession number. The country and year of isolation of each of these 38 strains are described in Tables 1-3 in the previous Examples. More than half of the strains were from Kenya, with a substantial portion coming from Uganda, and a few strains coming from Tanzania. About half of the strains were isolated between 2000 and 2002.

TABLE 4

|  | A.cons |
| --- | --- |
| A_MSA4070_ | 0.0318 |
| A_KNH1211_ | 0.04807 |
| A_97TZ03_1 | 0.0535 |
| A_99UGA070 | 0.05354 |
| A_SE8891UG | 0.05383 |
| A_KEQ23-17 | 0.06476 |
| A_98UG5713 | 0.07043 |
| A_NKU3005_ | 0.0709 |
| A_SE7535UG | 0.07117 |
| A_98UG5714 | 0.07613 |
| A_SE6594UG | 0.07634 |
| A_TZA341_1 | 0.0805 |
| A_MSA4069_ | 0.08097 |
| A_KNH1199_ | 0.08213 |
| A_97TZ02_1 | 0.08276 |
| A_KSM4030- | 0.08704 |
| A_KSM4021- | 0.08795 |
| A_MSA4076_ | 0.08873 |
| A_KNH1209_ | 0.0899 |
| A_KER2012- | 0.09224 |
| A_KNH1144_ | 0.09577 |
| A_KER2008_ | 0.09703 |
| A_MSA4072_ | 0.09892 |
| A_98UG5713 | 0.09892 |
| A_99UGG033 | 0.09967 |
| A_KNH1088_ | 0.10303 |
| A_92UG037_ | 0.10654 |
| A_SE8538TZ | 0.10996 |
| A_KER2009_ | 0.1102 |
| A_MSA4079_ | 0.11083 |
| A_KSM4024_ | 0.11126 |
| A_SE8131UG | 0.11326 |
| A_SE7253SO | 0.11453 |
| A_KNH1207_ | 0.11549 |
| A_TZA173_1 | 0.13766 |
| A_98UG5713 | 0.1399 |
| A_UGU455_1 | 0.15688 |

TABLE 4-continued

|  | A.cons |
| --- | --- |
| A_KNH1135_ | 0.16076 |
| A. cons | 0 |

The Nef protein sequences were aligned with spaces added to preserve alignment in regions with insertions or deletions. A 50% consensus sequence was derived. The consensus amino acid sequence is shown FIG. 7. In FIG. 7 the spaces that were added to preserve alignment in regions with insertions or deletions are represented by dashes, and the positions for which a 50% consensus was not attained are represented by an "X". There were six amino acid positions for which a 50% consensus was not attained.

For each of the 38 sequences used to generate the consensus sequence, the "distance" of that sequence from the consensus sequence was calculated using the Dayhoff PAM250 substitution matrix, which weights substitutions according to the degree of biochemical similarity. As shown in Table 4, the distance of each strain's sequence from the consensus sequence ranged from 3.2 to 16.1% with a mean distance of 9.3%.

Figure 8:
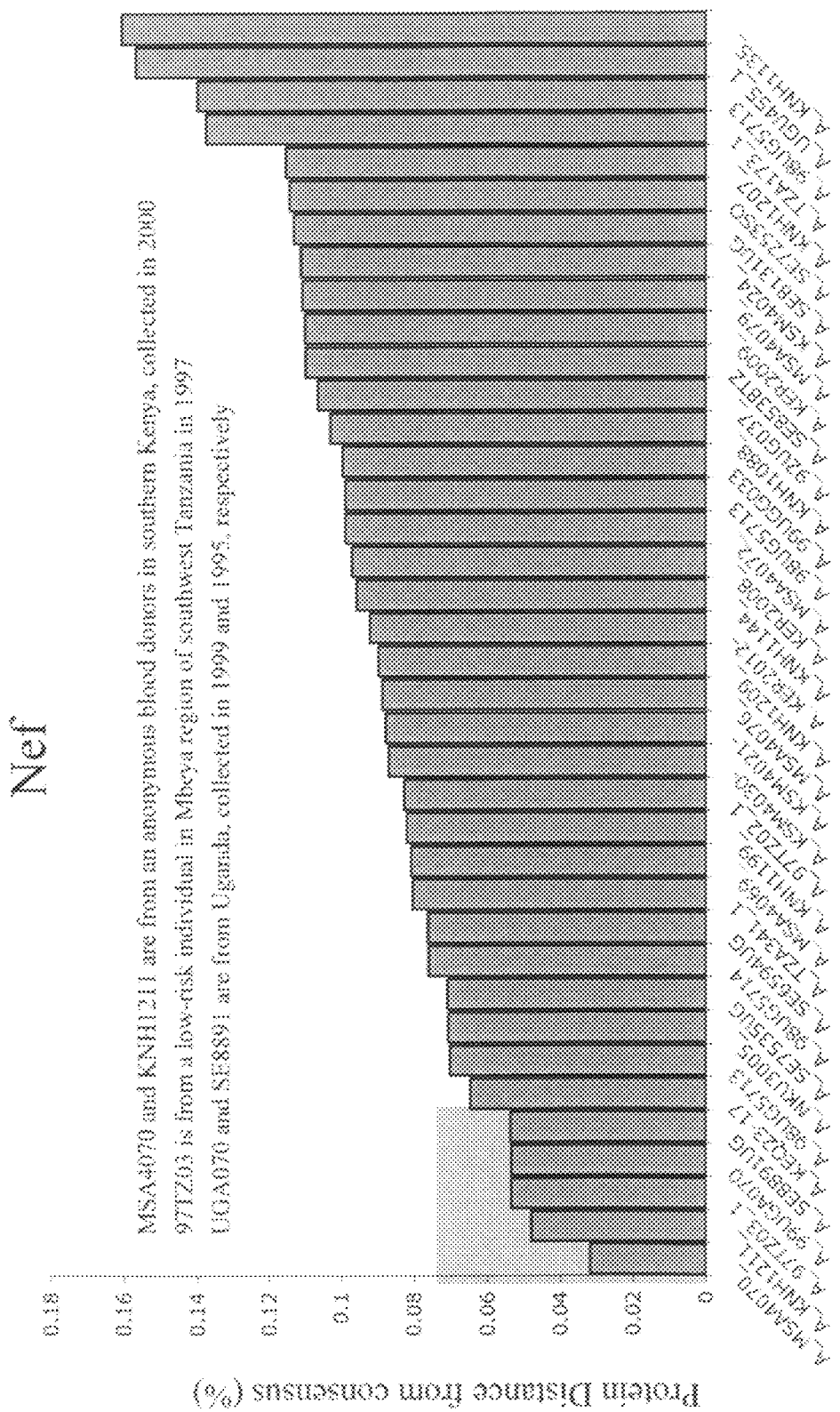
FIG. 8 is a graph illustrating the "distance" of the Nef protein sequences of circulating HIV-Clade A strains to that of the consensus HIV-1 Clade A Nef protein sequence.
Figure 9:
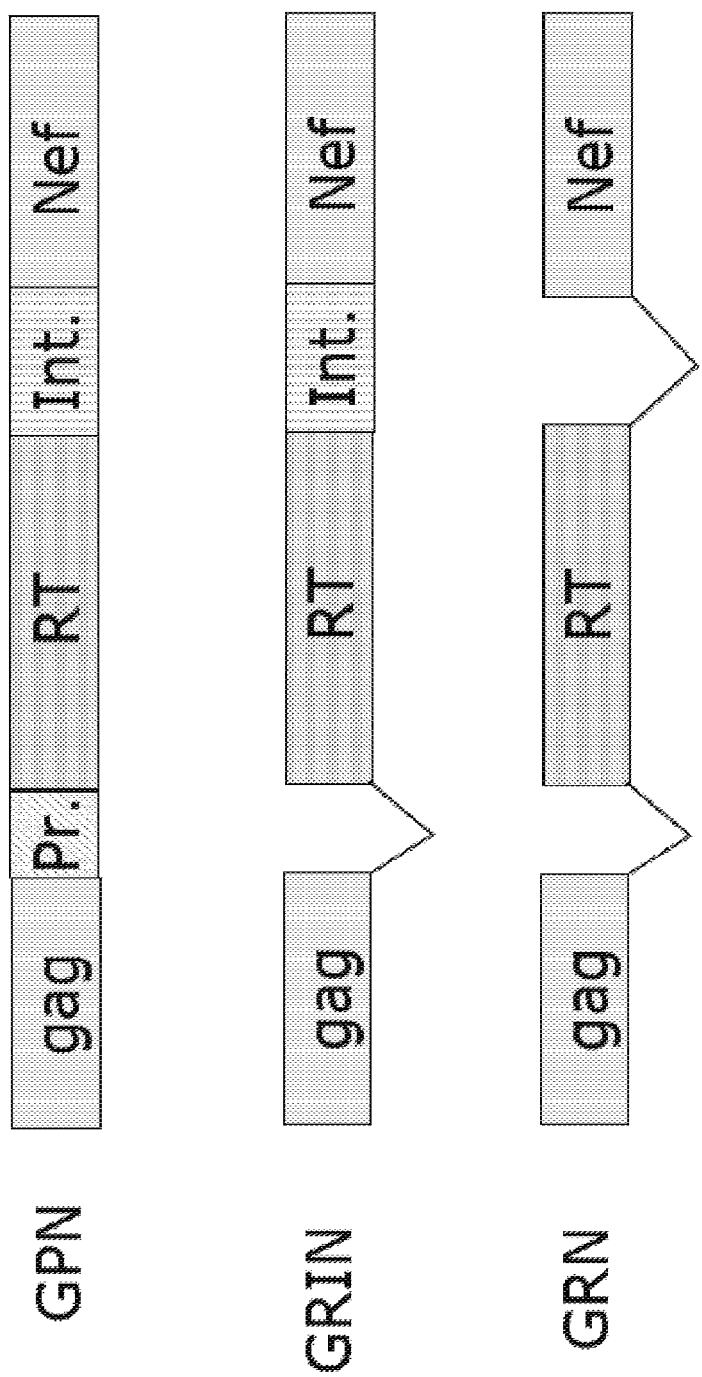
FIG. 9 is a schematic representation of the GRIN and GRN transgenes.

FIG. 8 illustrates the distance of each strain's amino acid sequence from the consensus amino acid sequence in graphical form, and identifies the five strains having sequences that are closest to the consensus sequences. These five strains were MSA4070 and KNH1211, both of which were from anonymous donors in southern Kenya and were collected in 2000, 97TZ03 from a low-risk individual in the Mbeya region of southwest Tanzania which was collected in 1997, and UGA070 and SE8891 both of which were from individuals in Uganda and were collected in 1999 and 1995, respectively.

Example 5

Strains of HIV Clade A Strains that are Closest to the HIV Clade A Consensus Sequences As described in Examples 1 to 4 above, and as summarized in Table 5, the strains of HIV Clade A having Gag, Pol, Env and Nef sequences that were most similar to the consensus sequences of each of these proteins were identified. In addition, the strains that were overall closest to the consensus sequence were identified by ranking each of the strains according to its closeness to the consensus sequence of a particular protein wherein the strain ranked number 1 was that whose sequence for that protein was closest to that of the consensus sequence, and then summing the rankings for each strain across all four of the proteins (i.e. Gag, Pol, Env, and Nef). The six strains that were overall closest to the consensus sequence across all four of the proteins studied are listed below in Table 6. It can be seen that strain 97TZ02 has a sequence which is overall closest to the consensus sequences of each of the Gag, Pol, Env and Nef genes.

TABLE 5

| Gag | Pol | Env | Nef |
| --- | --- | --- | --- |
| 97TZ02 | MSA4070 | KEQ23 | MSA4070 |
| TZA173 | SE7245SO | TZA341 | KNH1211 |
| KNH1144 | SE8538 | KNH1088 | 97TZ03 |
| SE7535UG |  |  | 99UGA070 |
|  |  |  | SE8891UG |

TABLE 6

|  | gag | pol | env | nef | sum |
|---|---|---|---|---|---|
| A_97TZ02_1 | 1 | 5 | 9 | 15 | 30 |
| A_KEQ23-17 | 18 | 6 | 1 | 6 | 31 |
| A_MSA4070_ | 16 | 1 | 16 | 1 | 34 |
| A_TZA341_1 | 12 | 8 | 2 | 12 | 34 |
| A_SE7535UG | 4 | 20 | 12 | 9 | 45 |
| A_KNH1211_ | 5 | 7 | 31 | 2 | 45 |

Example 6

Construction of GRIN, GRN, and Env Transgenes

Transgene constructs were made using HIV Clade A protein sequences derived from the most recently identified circulating HIV-1 field isolates that were the closest match to the HIV Clade A consensus sequence for each such protein. This strategy was developed in order to maximize the biological relevance of the HIV Clade A sequences used. It should be understood that other sequences, i.e. sequences other than the specific sequences described in this example, can also be used in accordance with the invention. If other sequences are used it is preferred that the sequences are selected such that they are derived from recent field isolates and have sequences that are close to the HIV Clade A consensus sequences described herein, or to HIV Clade A consensus sequences that may be generated in the future.

Constructs referred to as GRIN and GRN were made. The GRIN construct contained HIV Clade A sequences encoding the Gag, Pol (RT and Integrase) and Nef proteins. The GRN transgene contained sequences encoding the Gag, RT and Nef proteins. The GRIN and GRN constructs are represented schematically in FIG. 9. The GRIN and GRN transgenes were made using the Gag protein sequence from strain TZA173 having Genbank accession number AY253305, the Pol (comprising both RT and Int sequences) sequence from strain MSA4070 having Genbank accession number AF457081, and the Nef sequence from strain MSA4070 having Genbank accession number AF457081. These sequences were selected because they were from the most recently identified circulating HIV-1 field isolates that had the closest match to the consensus sequence for each of Gag, Pol, and Nef, respectively. These sequences are illustrated in FIGS. 10, 11, and 12, respectively.

An Env construct was also made containing the Env coding sequence from the most recently identified circulating HIV-1 field isolate that had the closest match to the consensus Env sequence, i.e. the Env protein sequence from strain TZA341 having Genbank accession number AY253314. This sequence is illustrated in FIG. 13.

All sequences were then codon optimized for human expression by GeneArt (Germany). The optimized gene sequences allow high level and stable protein expression in humans or other mammalian cells. Further details of the codon optimization process are provided in Example 8. The transgenes were also engineered to incorporate specific mutations or arranged in a specific order to abrogate the normal function of the gene products in vivo. The details of these mutations, and the biological effects of each, are described in Example 7 below.

For the GRIN and GRN transgenes, the coding sequences for each of the Gag, Pol (RT & Int) or RT, and Nef proteins were joined in-frame such that each of the transgene constructs (i.e. either GRIN or GRN) encoded a single fusion protein. Blast searches were performed to ensure that no neoepitopes were formed at the junctions. Although not used in the present example, it should be noted that it is also possible to insert spacer sequences between the sequences coding for the individual components of the final fusion protein to allow optimal protein domain folding, for example a spacer region may be added between Gag and Pol to allow the protein domains to fold in a more native conformation. Also, unique restriction sites were added at the 5" and 3' ends of each sequence in order to facilitate the joining together of each sequence (for example, the joining of the 5" end of Nef to the 3' end of Pol, etc.).

For use in vivo the GRIN, GRN and Env transgenes were inserted into either the Ad5, Ad35, Ad11, C6, or C7 adenovirus vectors. In order to facilitate cloning into theses vectors unique restriction sites were added at the 5" and 3' ends of the GRIN, GRN, or Env constructs. FIGS. 14A-14C provides the sequence of GRIN as inserted into the Ad35 vector, and shows the restriction sites used to clone the GRIN sequence into the Ad35 vector (underlined and in bold typeface). The sequence shown also includes the CMV promoter sequence upstream of the GRIN sequence. FIGS. 15A-15B provides the sequence of Env as inserted into the Ad35 vector, and shows the restriction sites used to clone the Env sequence into the Ad35 vector (underlined and in bold typeface). The sequence shown also includes the CMV promoter sequence upstream of the Env sequence.

Standard recombinant DNA and cloning techniques were used to generate all of the above constructs. Such techniques are well known to those of skill in the art. See for example, "Molecular Cloning: A Laboratory Manual", second edition (Sambrook et al. 1989).

Example 7

Mutations to Abrogate Normal In Vivo Function of HIV Clade A Proteins

Table 7 summarizes the mutations engineered into the GRIN and GRN sequences to abrogate the in vivo function of their gene products. These mutations were made using standard recombinant DNA techniques. Such techniques are well known to those of skill in the art.

TABLE 7

| Design | Gene | Mutation/Rationale |
|---|---|---|
| Mutation | gag | Gly2 → Ala: Removes myristylation site preventing VLP formation. |
| Mutation | gag | To avoid slippage at the natural frame shift sequence, the DNA sequence was mutated in a manner that leaves the conserved amino acid sequence (NFLG) intact and allows only the full-length GagPol protein product to be translated. |
| Mutation | RT | Asp185 → Ala & Asp186 → Ala: Inactivates active enzyme residues. |
| Mutations | Integrase (IN) | Asp 64 → Ala, Asp116 → Ala & Glu 152 → Ala: Inactivates active enzyme residues. |
| No change | Nef | Fusion of nef N-terminus to IN C-terminus prevents myristylation and membrane targeting abrogating nef function. |

Gag protein is expressed as a 55-kDa polyprotein precursor ($Pr55^{gag}$), and is cleaved by the HIV-1 viral protease. Four major viral proteins result from the cleavage; Matrix (MA), Capsid (CA), Nucleocapsid (NC), and p6; as well as two spacer polypeptides p2 and p1, which represent sequences between CA and NC and between NC and p6, respectively.

MA plays a key role in several steps in virus replication, including the critical mediation of viral particle assembly and budding from the cell plasma membrane through the formation of virus-like particles (VLPs) (See Gheysen, D., E. Jacobs, F. de Foresta, D. Thiriart, M. Francotte, D. Thines, and M. De Wilde. (1989). Assembly and release of HIV-1 precursor pr55gag virus-like particles from recombinant baculovirus-infected cells. Cell 59:103-112).

Both Pr55$^{gag}$ and the MA (p17) are myristylated, i.e. amide bond formation to myristic acid. See Veronese di Marzo, F., Copeland, T. D., Oroszlan, S., Gallo, R. C. & Sarngadharan, M. G. (1988). J. Virol. 62, 795-801. See also section on Nef within Example 7 for a full description of myristylation process. Different HIV-1 isolates demonstrate that the myristyl-acceptor is the N-terminal glycine residue (Gly2). See Bryant & Ratner. (1990). Myristoylation-dependent replication and assembly of human immunodeficiency virus 1. Proc. Nadl. Acad. Sci. USA; 87: 523-527.

Bryant and Ratner (1990) demonstrated that substitution of Gly2 with Ala eliminated virus replication of an HIV-1 clone. The Pr55$^{gag}$, deficient of the myristyl-acceptor glycine, accumulated in infected Hela cells and was not processed into mature virion capsid. It was concluded that myristylation of the Gly2 is required for stable plasma membrane association and subsequent assembly of virions. Other groups have similarly demonstrated the importance of the mystriylation of Gly2 in the MA. See Gottlinger H G, Sodroski J G, Haseltine W A. (1989). Role of capsid precursor processing and myristoylation in morphogenesis and infectivity of human immunodeficiency virus type 1. Proc Natl Acad Sci USA; 86:5781-5785, and Paul Spearman, Jaang-Jiun Wang, Nancy Vander Heyden and Lee Ratner. (1994). Identification of Human Immunodeficiency Virus Type 1 Gag Protein Domains Essential to Membrane Binding and Particle Assembly. J. Virol; 68 (5): 3232-3242.

If the myristyl-acceptor N-terminal glycine (Gly2) in MA is mutated, membrane binding is abrogated and particle assembly is prevented. Thus, Clade A Gag is engineered to change Gly2→Ala. This results in the loss of the Gag biological function.

Reverse transcriptase (RT) is a viral enzyme essential for replication. RT converts incoming viral RNA into dsDNA, catalyzed by the RNA- and DNA-dependent polymerase and RNase H activities of the enzyme. RT is a heterodimer composed of p66 and p51 subunit proteins. See Alfredo Jacobo-Molina et al. (1993). Crystal structure of human immunodeficiency virus type 1 reverse transcriptase complexed with double-stranded DNA at 3.0 A resolution shows bent DNA. Proc. Natl. Acad. Sci. USA; 90: 6320-6324. p66 has two domains, the polymerase and RNase H. p51 has the same polymerase domain.

The catalytically essential Asp-110, Asp-185, and Asp-186 residues are located in the highly conserved DNA polymerase active site. These three residues, termed the "the catalytic triad" are thought to bind the divalent cations necessary for catalysis function. See Alfredo Jacobo-Molina et al. (1993). Crystal structure of human immunodeficiency virus type 1 reverse transcriptase complexed with double-stranded DNA at 3.0 A resolution shows bent DNA. Proc. Natl. Acad. Sci. USA; 90: 6320-6324.

The mutation of the aspartic acids at residues 185 and 186 into either asparagine or glutamate have been demonstrated to result in mutant proteins which were catalytically inactive. See Lowe D M, Parmar V, Kemp S D, Larder B A. (1991). Mutational analysis of two conserved sequence motifs in HIV-1 reverse transcriptase. FEBS Lett.; 6; 282 (2):231-4.

Mutation of Asp185→Ala & Asp186→Ala in the Clade A RT will inactivate the RT polymerase enzyme by disrupting the "catalytic triad". This will eliminate the biological function of the Clade A RT.

Proviral cDNA generated by RT is integrated into the host cell genome through the action of the viral Integrase (Int) enzyme. Int contains a DNA recombinase domain that catalyzes two distinct endonucleolytic reactions. The first reaction, 3' processing, removes dinucleotides from each end of the cDNA producing two-nucleotide 5' extensions at both ends. In the second reaction, Int non-specifically cleaves the host cell DNA and joins the free 3' groups of the cDNA termini to the 5' groups of the cleaved host cell DNA. Cellular enzymes repair gaps resulting in a fully integrated viral genome into the host cell DNA. See Coffin J M. Retroviridae and their Replication. Chapter 27. p645-708 & Wong-Staal F. Human Immunodeficiency Viruses and Their Replication. Chapter 28. p709-723. In Fields, B N. & Knipe D M. 2nd Edition Fundamental Virology. Raven Press. See also Engelman A, Mizuuchi K, Craigie R. (1991). HIV-1 DNA integration: mechanism of viral DNA cleavage and DNA strand transfer. Cell; 67 (6):1211-1221. The catalytic domain, residues 50 to 212, contain a triad of residues Asp-64, Asp-116, and Glu-152 (termed the D,D-35-E motif) that compromises the enzyme active site. See Esposito, D., and R. Craigie. (1999). HTV integrase structure and function. Adv. Virus Res. 52:319-333. See also Khan, E., J. P. G. Mack, R. A. Katz, J. Kulkosky, and A. M. Skalka. (1991). Retroviral integrase domains: DNA binding and the recognition of LTR sequences. Nucleic Acids Res. 19:851-860.

Through a variety of techniques, groups have demonstrated the abrogation of endonuclease and/or integration function of IN through site directed mutation of Asp-64, Asp-116, and Glu-152 residues in the D,D-35-E motif See Drelich M, Wilhelm R, Mous J. (1992). Identification of amino acid residues critical for endonuclease and integration activities of HIV-1 IN protein in vitro. Virology; 188(2):459-468. See also LaFemina R L, Schneider C L, Robbins H L, Callahan P L, LeGrow K, Roth E, Schleif W A, Emini E A. (1992). Requirement of active human immunodeficiency virus type 1 integrase enzyme for productive infection of human T-lymphoid cells. J Virol; 66 (12):7414-7419. See also Leavitt A D, Shiue L, Varmus H E. (1993). Site-directed mutagenesis of HIV-1 integrase demonstrates differential effects on integrase functions in vitro. J Biol Chem; 268 (3):2113-2119.

Mutation of Asp-64→Ala, Asp-116→Ala, and Glu-152→Ala in the Clade A Int will inactivate the Int active enzyme by disrupting the critical D,D-35-E motif. This will eliminate the biological function of Clade A Int.

The Negative factor (Nef) protein (27-kDa) is the earliest viral protein to accumulate in the newly infected cell. See Haseltine, W. (1991). Molecular biology of the human immunodeficiency virus type 1. FASEB. Vol 5.2349-2360. Through myristylation, Nef is able to localize on the cytosol side of the cell membrane. See Yu G, Felsted R L. (1992). Effect of myristoylation on p27 nef subcellular distribution and suppression of HIV-LTR transcription. Virology. 187 (1):46-55. See also Kaminchik, J., N. Bashan, A. Itach, N. Sarver, M. Gorecki, and A. Panet. (1991). Genetic characterization of human immunodeficiency virus type 1 nef gene products translated in vitro and expressed in mammalian cells. J. Virol. 65:583-588. Myristylation of proteins is a co-translational event and involves the transfer of myristate from myristyl-Coenzyme A to the amino-terminal motif MGXXX of proteins by the enzyme N-myristyl transferase (NMT). See Towler, D. A., S. P. Adams, S. R. Eubanks, D. S. Towery, E.

Jackson-Machelski, L. Glaser & J. I. Gordon (1987). Purification and characterization of yeast myristoyl CoA:protein N-myristoyltransferase. Proc Natl Acad Sci USA 84:2708-2712. The lead methionine of the polypeptide is cleaved by the methionine amino peptidase during translation and NMT recognizes the newly generated terminal amino group of glycine of the emerging peptide after approximately twenty residues are free of the ribosome. NMT transfers myristate to the glycine residue (the myristyl-acceptor) and myristylation is completed. Replacement of the penultimate glycine myristyl-acceptor with any other amino acid residue inhibits myristylation. See Towler, D. A., S. R. Eubanks, D. S. Towery, S. P. Adams & L. Glaser (1987). Amino-terminal processing of proteins by N-myristoylation. Substrate specificity of N-myristoyl transferase. J Biol Chem 262:1030-1036.

Nef is a multifunctional protein able to modulate a number of surface molecules of the infected cell, such as CD4 (see Garcia, J. V., and A. D. Miller. (1991). Serine phosphorylation-independent downregulation of cell-surface CD4 by nef. Nature 350:508-511; and Mariani R and Skowronski J. (1993). CD4 down-regulation by nef alleles isolated from human immunodeficiency virus type 1-infected individuals Proc. Natl. Acad. Sci. USA. Vol. 90, pp. 5549-5553; and Aiken C, Konner J, Landau N R, Lenburg M E, Trono D (1994). Nef induces CD4 endocytosis: requirement for a critical dileucine motif in the membrane-proximal CD4 cytoplasmic domain. Cell. 11; 76(5):853-64), CD28 (see Swigut, T., N. Shohdy, and J. Skowronski. (2001). Mechanism for down-regulation of CD28 by Nef. EMBO J. 20:1593-1604), MHC-I (see Schwartz, O., V. Marechal, S. Le Gall, F. Lemonnier, and J. M. Heard. (1996). Endocytosis of major histocompatibility complex class 1 molecules is induced by the HIV-1 Nef protein. Nat. Med. 2:338-342), the macrophage-expressed MHC 1b protein HFE (see Drakesmith H, Chen N, Ledermann H, Screaton G, Townsend A, Xu X N. (2005). HIV-1 Nef down-regulates the hemochromatosis protein HFE, manipulating cellular iron homeostasis. Proc Natl Acad Sci USA. 102 (31):11017-22), MHC-II (see Stumptner-Cuvelette, P., S. Morchoisne, M. Dugast, S. Le Gall, G. Raposo, O, Schwartz, and P. Benaroch. (2001). HIV-1 Nef impairs MHC class II antigen presentation and surface expression. Proc. Natl. Acad. Sci. USA 98:12144-12149), as well as disrupt signal transduction pathways (see Tolstrup, M., L. Ostergaard, A. L. Laursen, S. F. Pedersen, and M. Duch. (2004). HIV/SIV escape from immune surveillance: focus on Nef. Curr. HIV Res. 2:141-151) via association with multiple kinases and other cell surface proteins at the cell membrane. The mechanisms of these actions and the nef motifs involved remain to be fully elucidated.

Specifically, a Nef mutant with deletion of the 19 N-terminal amino acids, including the N-terminus myristylation signal eliminated CD4 and MHC-1 down-regulation, while maintaining most CTL, T-helper and B-cell epitopes (see Peng B, Robert-Guroff M (2001). Deletion of N-terminal myristoylation site of HIV Nef abrogates both MHC-1 and CD4 down-regulation. Immunol Lett. 78 (3):195-200). Other groups have demonstrated that mutation of the Nef amino-terminal glycine (Gly2) into alanine prevents myristylation (see Liang, X. et al. (2002). Development of HIV-1 Nef vaccine components: immunogenicity study of Nef mutants lacking myristylation and dileucine motif in mice. Vaccine 20: 3413-3421, and Kaminchik, J. et al. (1991). Genetic Characterization of Human Immunodeficiency Virus Type 1 nef Gene Products Translated in vitro and Expressed in Mammalian Cells. J. of Virol. 65 (2): 583-588).

Since the amino-terminal motif MGXXX of the Clade A Nef is embedded within the GRIN fusion protein, there is no nascent methionine to be cleaved by the methionine amino peptidase during translation. Thus, no newly generated amino-terminal group of glycine occurs and NMT is unable to execute myristylation. In conclusion, the inability of Nef in GRIN to undergo myristylation abrogates the biological function of Nef.

Example 8

Codon Optimization for GRIN (GagPolNef) and Env

The codon usage for each of GRIN and Env was adapted to the codon bias of human genes. The nucleotide and amino acid sequence of the codon optimized GRIN sequence is provided in FIGS. 16A-16J. The nucleotide and amino acid sequence of the codon optimized Env sequence is provided in FIGS. 17A-17D.

Regions of very high (greater than 80%) or very low (less than 30%) GC content were avoided where possible. During the optimization process the following cis-acting motifs were avoided: internal TATA boxes, chi-sites, ribosomal entry sites, AT-rich or GC-rich sequence stretches, ARE, INS, or CRS sequence elements, repeat sequences, RNA secondary structures, cryptic splice donor and acceptor sites, branch points, and HindIII, NcoI, BglII and BclI restriction sites except as indicated in the sequences provided in FIGS. 16 and 17. Also, a Kozak sequence was introduced upstream of the starting ATG for each of GRIN and Env to increase translation initiation, and two stop codons were added to each of GRIN and Env to ensure efficient termination. Restrictions sites to facilitate subcloning were also added, as indicated in FIGS. 16 and 17.

Example 9

Non-Human Primate Study

A non-human primate (Chinese rhesus macaques) study was conducted with the primary objective to assess the immunogenicity of GRIN and ENV in a human adenovirus type 35 (Ad35) vector delivery system. Animals were given increasing doses of Ad35-GRIN/ENV ($10^9$, $10^{10}$ and $10^{11}$ virus particles [vp]; intramuscular route) and received two immunizations at month 0 and month 6 (with 8 animals per group for the first immunization and 4 animals per group for the second immunization). At various timepoints (from week 0 through to week 50), animals were bled and immunogenicity measured by ELISpot for IFN-gamma (see FIGS. 23A and 23B for the $10^{10}$ and $10^{11}$ vp dosages, respectively).

A dose response was observed (data for $10^9$ vp not shown), both in ELISPot intensity and frequency of responders following the prime (data not shown). Responses were seen to all vaccine antigen components of GRIN/ENV and IFNγ ELISPOT responses were boosted after the second immunization at month 6.

The invention is further described by the following numbered paragraphs:

1. A consensus nucleotide sequence for HIV-1 Clade A antigens, wherein the sequence comprises nucleotide sequences encoding HIV-1 Clade A Gag, Pol (RT and Int), and Nef ("GRIN), HIV-1 Clade A Gag, RT and Nef ("GRN") or HIV-1 Clade A Env.

2. A consensus nucleotide sequence according to paragraph 1 wherein the encoded Gag protein has the amino acid sequence of FIG. 1.

3. A consensus nucleotide sequence according to paragraph 1 wherein the encoded Pol protein has the amino acid sequence of FIG. 3.

4. A consensus nucleotide sequence according to paragraph 1 wherein the encoded Env protein has the amino acid sequence of FIG. 5.

5. A consensus nucleotide sequence according to paragraph 1 wherein the encoded Nef protein has the amino acid sequence of FIG. 7.

6. A method of identifying an HIV-1 Clade A antigen from a circulating strain or field isolate of HIV-1 that has an amino acid sequence that is similar to the consensus amino acid sequence for that HIV-1 Clade A antigen, comprising comparing the amino acid sequences of antigens from circulating strains or field isolates of HIV-1 to the consensus amino acid sequence for that protein, and selecting an antigen from the circulating strains or field isolates of HIV-1 that has a small protein distance from the consensus sequence.

7. An HIV-1 Clade A antigen identified using the method of paragraph 6.

8. An method of producing a transgenic HIV-1 Clade A antigen comprising selecting an HIV-1 Clade A antigen using the method of paragraph 6 and mutating the nucleotide sequence that encodes the antigen wherein the mutation abrogates the function of that antigen.

9. A method of generating an immune response against HIV-1 comprising administering to a subject a composition comprising a nucleotide sequence or antigen according to any of the previous paragraphs.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A protein comprising the amino acid sequence of SEQ ID NO: 4.

2. A method of generating an immune response against HIV-1 comprising administering to a subject a composition comprising the protein of claim 1.

* * * * *